US011669858B2

(12) United States Patent
Knight et al.

(10) Patent No.: US 11,669,858 B2
(45) **Date of Patent: *Jun. 6, 2023**

(54) ANALYSIS OF CONTROLLED AND AUTOMATIC ATTENTION FOR INTRODUCTION OF STIMULUS MATERIAL

(71) Applicant: Nielsen Consumer LLC, New York, NY (US)

(72) Inventors: Robert T. Knight, Berkeley, CA (US); Ramachandran Gurumoorthy, Berkeley, CA (US); Anantha Pradeep, Berkeley, CA (US)

(73) Assignee: Nielsen Consumer LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/516,349

(22) Filed: Nov. 1, 2021

(65) Prior Publication Data

US 2022/0058687 A1 Feb. 24, 2022

Related U.S. Application Data

(63) Continuation of application No. 16/360,282, filed on Mar. 21, 2019, now Pat. No. 11,170,400, which is a (Continued)

(51) Int. Cl.
*A61B 5/16* (2006.01)
*G06Q 30/0242* (2023.01)
(Continued)

(52) U.S. Cl.
CPC ......... *G06Q 30/0244* (2013.01); *A61B 5/377* (2021.01); *G06Q 30/0269* (2013.01); *A61B 5/163* (2017.08)

(58) Field of Classification Search
CPC ........... A61B 5/16; A61B 5/163; A61B 5/377; G06Q 30/0244; G06Q 30/0269;
(Continued)

(56) References Cited

U.S. PATENT DOCUMENTS

| | | | |
|---|---|---|---|
| 2,549,836 | A | 4/1951 | Mcintyre |
| 3,490,439 | A | 1/1970 | Rolston |

(Continued)

FOREIGN PATENT DOCUMENTS

| | | |
|---|---|---|
| EP | 1087618 | 3/2001 |
| EP | 1609418 | 12/2005 |

(Continued)

OTHER PUBLICATIONS

Final Rejection, issued by the United States Patent and Trademark Office in connection with U.S. Appl. No. 12/056,211, dated Jul. 8, 2011, 16 pages.

(Continued)

*Primary Examiner* — Eric J Messersmith
(74) *Attorney, Agent, or Firm* — Hanley, Flight & Zimmerman, LLC

(57) ABSTRACT

An example system disclosed herein includes an analyzer to determine a first priming characteristic of media at a first location based on first neuro-response data and determine a second priming characteristic of the media at the second location based on second neuro-response data. The example system includes a selector to select a third location in the media after the first location or a fourth location in the media after the second location as a candidate location for introduction of advertising material based on the first priming characteristic and the second priming characteristic. The selector is to select the third location when the first priming characteristic indicates increased receptivity to the advertising material at the first location relative to the second (Continued)

Stimulus Material Placement And Personalization
Receive Personalized Stimulus Material 701
Identify Candidate Locations For Introduction Of Stimulus Material 703
Select Candidate Locations Using Candidate Location Characteristics 705
Insert Stimulus Material Into Video Game 707
Evaluate Neuro-Response Data With Stimulus Material Inserted 709
Update Candidate Location Characteristics 711
End priming characteristic and select the fourth location when the second priming characteristic indicates increased receptivity to the advertising material at the second location relative to the first priming characteristic.

20 Claims, 8 Drawing Sheets

Related U.S. Application Data continuation of application No. 16/037,666, filed on Jul. 17, 2018, now Pat. No. 10,269,036, which is a continuation of application No. 15/299,752, filed on Oct. 21, 2016, now Pat. No. 10,068,248, which is a continuation of application No. 12/608,660, filed on Oct. 29, 2009, now Pat. No. 9,560,984.

(51) Int. Cl.
*G06Q 30/0251* (2023.01)
*A61B 5/377* (2021.01)

(58) Field of Classification Search
CPC G09G 3/3225; G09G 3/3233; H01L 27/1222; H01L 27/124; H01L 27/1248
See application file for complete search history.

(56) References Cited

U.S. PATENT DOCUMENTS 3,572,322 A 3/1971 Wade
3,735,753 A 5/1973 Pisarski
3,880,144 A 4/1975 Coursin et al.
3,901,215 A 8/1975 John
3,998,213 A 12/1976 Price
4,075,657 A 2/1978 Weinblatt
4,145,122 A 3/1979 Rinard et al.
4,149,716 A 4/1979 Scudder
4,201,224 A 5/1980 John
4,279,258 A 7/1981 John
4,411,273 A 10/1983 John
4,417,592 A 11/1983 John
4,537,198 A 8/1985 Corbett
4,557,270 A 12/1985 John
4,610,259 A 9/1986 Cohen et al.
4,613,951 A 9/1986 Chu
4,626,904 A 12/1986 Lurie
4,632,122 A 12/1986 Johansson et al.
4,683,892 A 8/1987 Johansson et al.
4,686,999 A 8/1987 Snyder et al.
4,695,879 A 9/1987 Weinblatt
4,736,751 A 4/1988 Gevins et al.
4,800,888 A 1/1989 Itil et al.
4,802,484 A 2/1989 Friedman et al.
4,846,190 A 7/1989 John
4,859,050 A 8/1989 Borah et al.
4,870,579 A 9/1989 Hey
4,885,687 A 12/1989 Carey
4,894,777 A 1/1990 Negishi et al.
4,913,160 A 4/1990 John
4,955,388 A 9/1990 Silberstein
4,967,038 A 10/1990 Gevins et al.
4,973,149 A 11/1990 Hutchinson
4,987,903 A 1/1991 Keppel et al.
5,003,986 A 4/1991 Finitzo et al.
5,010,891 A 4/1991 Chamoun
5,038,782 A 8/1991 Gevins et al.
5,052,401 A 10/1991 Sherwin
5,083,571 A 1/1992 Prichep
RE34,015 E 8/1992 Duffy
5,137,027 A 8/1992 Rosenfeld
5,213,338 A 5/1993 Brotz
5,226,177 A 7/1993 Nickerson
5,243,517 A 9/1993 Schmidt et al.
5,273,037 A 12/1993 Itil et al.
5,291,888 A 3/1994 Tucker
5,293,867 A 3/1994 Oommen
5,295,491 A 3/1994 Gevins
5,331,544 A 7/1994 Lu et al.
5,339,826 A 8/1994 Schmidt et al.
5,345,281 A 9/1994 Taboada et al.
5,357,957 A 10/1994 Itil et al.
5,363,858 A 11/1994 Farwell
5,392,788 A 2/1995 Hudspeth
5,406,956 A 4/1995 Farwell
5,410,609 A 4/1995 Kado et al.
5,436,830 A 7/1995 Zaltman
5,447,166 A 9/1995 Gevins
5,450,855 A 9/1995 Rosenfeld
5,474,082 A 12/1995 Junker
5,479,934 A 1/1996 Imran
5,513,649 A 5/1996 Gevins et al.
5,518,007 A 5/1996 Becker
5,537,618 A 7/1996 Boulton et al.
5,550,928 A 8/1996 Lu et al.
5,617,855 A 4/1997 Waletzky et al.
5,655,534 A 8/1997 Ilmoniemi
5,676,138 A 10/1997 Zawilinski
5,676,148 A 10/1997 Koo et al.
5,687,322 A 11/1997 Deaton et al.
5,720,619 A 2/1998 Fisslinger
5,724,987 A 3/1998 Gevins et al.
5,726,701 A 3/1998 Needham
5,729,205 A 3/1998 Kwon
5,736,986 A 4/1998 Sever, Jr.
5,740,035 A 4/1998 Cohen et al.
5,762,611 A 6/1998 Lewis et al.
5,771,897 A 6/1998 Zufrin
5,774,591 A 6/1998 Black et al.
5,787,187 A 7/1998 Bouchard et al.
5,800,351 A 9/1998 Mann
5,802,208 A 9/1998 Podilchuk et al.
5,802,220 A 9/1998 Black et al.
5,812,642 A 9/1998 Leroy
5,817,029 A 10/1998 Gevins et al.
5,842,199 A 11/1998 Miller et al.
5,848,399 A 12/1998 Burke
5,892,566 A 4/1999 Bullwinkel
5,945,863 A 8/1999 Coy
5,961,332 A 10/1999 Joao
5,974,262 A 10/1999 Fuller et al.
5,983,129 A * 11/1999 Cowan .................... A63F 13/10 600/545
5,995,868 A 11/1999 Dorfmeister et al.
6,001,065 A 12/1999 DeVito
6,016,475 A 1/2000 Miller et al.
6,021,346 A 2/2000 Ryu et al.
6,032,129 A 2/2000 Greef et al.
6,052,619 A 4/2000 John
6,088,040 A 7/2000 Oda et al.
6,099,319 A 8/2000 Zaltman et al.
6,120,440 A 9/2000 Goknar
6,128,521 A 10/2000 Marro et al.
6,154,669 A 11/2000 Hunter et al.
6,155,927 A 12/2000 Levasseur et al.
6,161,030 A 12/2000 Levendowski et al.
6,170,018 B1 1/2001 Voll et al.
6,171,239 B1 1/2001 Humphrey
6,173,260 B1 1/2001 Slaney
6,175,753 B1 1/2001 Menkes et al.
6,182,113 B1 1/2001 Narayanaswami
6,190,314 B1 2/2001 Ark et al.
6,212,502 B1 4/2001 Ball et al.
6,228,038 B1 5/2001 Claessens
6,236,885 B1 5/2001 Hunter et al.
6,236,975 B1 5/2001 Boe et al.
6,254,536 B1 7/2001 DeVito
6,280,198 B1 8/2001 Calhoun et al.
6,286,005 B1 9/2001 Cannon
6,289,234 B1 9/2001 Mueller
6,292,688 B1 9/2001 Patton
6,299,308 B1 10/2001 Voronka et al.
6,301,492 B1 10/2001 Zonenshayn

(56) References Cited

U.S. PATENT DOCUMENTS 6,301,493 B1 10/2001 Marro et al.
6,315,569 B1 11/2001 Zaltman
6,330,470 B1 12/2001 Tucker et al.
6,334,778 B1 1/2002 Brown
6,358,201 B1 3/2002 Childre et al.
6,370,513 B1 4/2002 Kolawa et al.
6,374,143 B1 4/2002 Berrang et al.
6,381,481 B1 4/2002 Levendowski et al.
6,398,643 B1 6/2002 Knowles et al.
6,422,999 B1 7/2002 Hill
6,434,419 B1 8/2002 Gevins et al.
6,435,878 B1 8/2002 Reynolds et al.
6,453,194 B1 9/2002 Hill
6,453,241 B1 9/2002 Bassett, Jr. et al.
6,487,444 B2 11/2002 Mimura
6,488,617 B1 12/2002 Katz
6,510,333 B1 1/2003 Licata et al.
6,510,340 B1 1/2003 Jordan
6,520,905 B1 2/2003 Surve et al.
6,545,685 B1 4/2003 Dorbie
6,575,902 B1 6/2003 Burton
6,577,329 B1 6/2003 Flickner et al.
6,585,521 B1 7/2003 Obrador
6,594,521 B2 7/2003 Tucker
6,598,006 B1 7/2003 Honda et al.
6,609,024 B1 8/2003 Ryu et al.
6,648,822 B2 11/2003 Hamamoto et al.
6,652,283 B1 11/2003 Van Schaack et al.
6,654,626 B2 11/2003 Devlin et al.
6,662,052 B1 12/2003 Sarwal et al.
6,665,560 B2 12/2003 Becker et al.
6,678,685 B2 1/2004 McGill et al.
6,688,890 B2 2/2004 von Buegner
6,708,051 B1 3/2004 Durousseau
6,712,468 B1 3/2004 Edwards
6,754,524 B2 6/2004 Johnson, Jr.
6,757,556 B2 6/2004 Gopinathan et al.
6,788,882 B1 9/2004 Geer et al.
6,792,304 B1 9/2004 Silberstein
6,842,877 B2 1/2005 Robarts et al.
6,850,252 B1 2/2005 Hoffberg
6,852,875 B2 2/2005 Prakash
6,888,457 B2 5/2005 Wilkinson et al.
6,904,408 B1 6/2005 McCarthy et al.
6,950,698 B2 9/2005 Sarkela et al.
6,958,710 B2 10/2005 Zhang et al.
6,973,342 B1 12/2005 Swanson
6,993,380 B1 1/2006 Modarres
7,020,508 B2 3/2006 Stivoric et al.
7,043,056 B2 5/2006 Edwards et al.
7,047,550 B1 5/2006 Yasukawa et al.
7,113,916 B1 9/2006 Hill
7,120,880 B1 10/2006 Dryer et al.
7,130,673 B2 10/2006 Tolvanen-Laakso et al.
7,150,715 B2 12/2006 Collura et al.
7,164,967 B2 1/2007 Etienne-Cummings et al.
7,177,675 B2 2/2007 Suffin et al.
7,222,071 B2 5/2007 Neuhauser et al.
7,246,081 B2 7/2007 Hill
7,249,708 B2 7/2007 McConnell et al.
7,272,982 B2 9/2007 Neuhauser et al.
7,286,871 B2 10/2007 Cohen
7,340,060 B2 3/2008 Tomkins et al.
7,359,894 B1 4/2008 Liebman et al.
7,391,835 B1 6/2008 Gross et al.
7,394,385 B2 7/2008 Franco, Jr. et al.
7,408,460 B2 8/2008 Crystal et al.
7,420,464 B2 9/2008 Fitzgerald et al.
7,443,292 B2 10/2008 Jensen et al.
7,460,827 B2 12/2008 Schuster et al.
7,463,143 B2 12/2008 Forr et al.
7,463,144 B2 12/2008 Crystal et al.
7,471,987 B2 12/2008 Crystal et al.
7,483,835 B2 1/2009 Neuhauser et al.
7,483,844 B2 1/2009 Takakura et al.
7,496,400 B2 2/2009 Hoskonen et al.
7,548,774 B2 6/2009 Kurtz et al.
7,551,952 B2 6/2009 Gevins et al.
7,592,908 B2 9/2009 Zhang et al.
7,614,066 B2 11/2009 Urdang et al.
7,623,823 B2 11/2009 Zito et al.
7,630,757 B2 12/2009 Dorfmeister et al.
7,636,456 B2 12/2009 Collins et al.
7,641,341 B2 1/2010 Weinblatt
7,650,793 B2 1/2010 Jensen et al.
7,658,327 B2 2/2010 Tuchman et al.
7,689,272 B2 3/2010 Farwell
7,697,979 B2 4/2010 Martinerie et al.
7,698,238 B2 4/2010 Barletta et al.
7,720,351 B2 5/2010 Levitan
7,729,755 B2 6/2010 Laken
7,765,564 B2 7/2010 Deng
7,774,052 B2 8/2010 Burton et al.
7,797,186 B2 9/2010 Dybus
7,809,420 B2 10/2010 Hannula et al.
7,840,248 B2 11/2010 Fuchs et al.
7,840,250 B2 11/2010 Tucker
7,844,484 B2 11/2010 Arnett et al.
7,865,394 B1 1/2011 Calloway et al.
7,892,764 B2 2/2011 Xiong et al.
7,895,075 B2 2/2011 Gettys et al.
7,895,625 B1 2/2011 Bryan et al.
7,908,133 B2 3/2011 Neuhauser
7,917,366 B1 3/2011 Levanon et al.
7,930,199 B1 4/2011 Hill
7,962,315 B2 6/2011 Jensen et al.
7,974,889 B2 7/2011 Raimbeault
7,988,557 B2 8/2011 Soderlund
8,014,847 B2 9/2011 Shastri et al.
8,027,518 B2 9/2011 Baker et al.
8,055,722 B2 11/2011 Hille
8,060,795 B2 11/2011 Bakekolo et al.
8,065,203 B1 11/2011 Chien et al.
8,069,125 B2 11/2011 Jung et al.
8,073,707 B2 12/2011 Teller et al.
8,079,054 B1 * 12/2011 Dhawan .............. H04N 21/812
705/14.6
8,082,215 B2 12/2011 Jung et al.
8,086,563 B2 12/2011 Jung et al.
8,098,152 B2 1/2012 Zhang et al.
8,099,315 B2 1/2012 Amento et al.
8,103,328 B2 1/2012 Turner et al.
8,126,220 B2 2/2012 Greig
8,135,606 B2 3/2012 Dupree
8,151,298 B2 4/2012 Begeja et al.
8,165,916 B2 4/2012 Hoffberg et al.
8,196,168 B1 6/2012 Bryan et al.
8,200,775 B2 6/2012 Moore
8,209,224 B2 6/2012 Pradeep et al.
8,219,438 B1 7/2012 Moon et al.
8,229,469 B2 7/2012 Zhang et al.
8,235,725 B1 8/2012 Hill
8,255,267 B2 8/2012 Breiter
8,270,814 B2 9/2012 Pradeep et al.
8,296,172 B2 10/2012 Marci et al.
8,300,526 B2 10/2012 Saito et al.
8,326,002 B2 12/2012 Hill
8,327,395 B2 12/2012 Lee et al.
8,332,883 B2 12/2012 Lee et al.
8,335,715 B2 12/2012 Pradeep et al.
8,381,244 B2 2/2013 King et al.
8,386,312 B2 2/2013 Pradeep et al.
8,386,313 B2 2/2013 Pradeep et al.
8,388,165 B2 3/2013 Zhang
8,392,250 B2 3/2013 Pradeep et al.
8,392,251 B2 3/2013 Pradeep et al.
8,392,253 B2 3/2013 Pradeep et al.
8,392,254 B2 3/2013 Pradeep et al.
8,392,255 B2 3/2013 Pradeep et al.
8,396,744 B2 3/2013 Pradeep et al.
8,473,345 B2 6/2013 Pradeep et al.
8,484,081 B2 7/2013 Pradeep et al.
8,484,801 B2 7/2013 Li et al.
8,494,610 B2 7/2013 Pradeep et al.

(56) References Cited

U.S. PATENT DOCUMENTS 8,494,905 B2 7/2013 Pradeep et al.
8,533,042 B2 9/2013 Pradeep et al.
8,548,852 B2 10/2013 Pradeep et al.
8,561,095 B2 10/2013 Dimitrova et al.
8,600,100 B2 12/2013 Hill
8,635,105 B2 1/2014 Pradeep et al.
8,655,428 B2 2/2014 Pradeep et al.
8,655,437 B2 2/2014 Pradeep et al.
8,709,054 B2 * 4/2014 Lowry ................ A61B 17/808 606/295
8,762,202 B2 6/2014 Pradeep et al.
8,764,652 B2 7/2014 Lee et al.
8,788,372 B2 7/2014 Kettner et al.
8,793,715 B1 7/2014 Weitzenfeld et al.
9,021,515 B2 4/2015 Lee et al.
9,336,535 B2 5/2016 Pradeep et al.
9,560,984 B2 2/2017 Pradeep et al.
9,886,981 B2 2/2018 Pradeep et al.
9,894,399 B2 2/2018 Lee et al.
10,068,248 B2 9/2018 Knight et al.
10,127,572 B2 11/2018 Pradeep et al.
10,140,628 B2 11/2018 Pradeep et al.
10,173,095 B2 1/2019 Gomberg et al.
10,189,294 B2 1/2019 Raymond et al.
10,269,036 B2 4/2019 Knight et al.
10,580,031 B2 3/2020 Pradeep et al.
10,679,241 B2 6/2020 Pradeep et al.
10,733,625 B2 8/2020 Pradeep et al.
10,937,051 B2 3/2021 Pradeep et al.
11,170,400 B2 11/2021 Knight et al.
2001/0013009 A1 8/2001 Greening et al.
2001/0020236 A1 9/2001 Cannon
2001/0029468 A1 10/2001 Yamaguchi et al.
2001/0032140 A1 10/2001 Hoffman
2001/0056225 A1 12/2001 DeVito
2002/0053076 A1 5/2002 Landesmann
2002/0055857 A1 5/2002 Mault
2002/0056087 A1 5/2002 Berezowski et al.
2002/0056124 A1 5/2002 Hay
2002/0059577 A1 5/2002 Lu et al.
2002/0065826 A1 5/2002 Bell et al.
2002/0072952 A1 6/2002 Hamzy et al.
2002/0077534 A1 6/2002 DuRousseau
2002/0082902 A1 6/2002 Ando et al.
2002/0103429 A1 8/2002 deCharms
2002/0111796 A1 8/2002 Nemoto
2002/0116042 A1 8/2002 Boling
2002/0143627 A1 10/2002 Barsade et al.
2002/0155878 A1 10/2002 Lert, Jr. et al.
2002/0156842 A1 10/2002 Signes et al.
2002/0169665 A1 11/2002 Hughes et al.
2002/0178440 A1 11/2002 Agnihotri et al.
2002/0188216 A1 12/2002 Kayyali et al.
2002/0188217 A1 12/2002 Farwell
2002/0193670 A1 12/2002 Garfield et al.
2003/0013981 A1 1/2003 Gevins et al.
2003/0036955 A1 2/2003 Tanaka et al.
2003/0037333 A1 2/2003 Ghashghai et al.
2003/0044050 A1 3/2003 Clark et al.
2003/0059750 A1 3/2003 Bindler et al.
2003/0063222 A1 4/2003 Creed et al.
2003/0065524 A1 4/2003 Giacchetti et al.
2003/0073921 A1 4/2003 Sohmer et al.
2003/0081834 A1 5/2003 Philomin et al.
2003/0093792 A1 5/2003 Labeeb et al.
2003/0100998 A2 5/2003 Brunner et al.
2003/0104865 A1 6/2003 Itkis et al.
2003/0118975 A1 6/2003 Stamm et al.
2003/0131351 A1 7/2003 Shapira
2003/0149344 A1 8/2003 Nizan
2003/0165270 A1 9/2003 Endrikhovski et al.
2003/0177488 A1 9/2003 Smith et al.
2003/0204412 A1 10/2003 Brier
2003/0208754 A1 11/2003 Sridhar et al.
2003/0233278 A1 12/2003 Marshall
2004/0001616 A1 1/2004 Gutta et al.
2004/0005143 A1 1/2004 Tsuru et al.
2004/0013398 A1 1/2004 Miura et al.
2004/0015608 A1 1/2004 Ellis et al.
2004/0055448 A1 3/2004 Byon
2004/0068431 A1 4/2004 Smith et al.
2004/0073129 A1 4/2004 Caldwell et al.
2004/0088289 A1 5/2004 Xu et al.
2004/0092809 A1 5/2004 DeCharms
2004/0098298 A1 5/2004 Yin
2004/0101212 A1 5/2004 Fedorovskaya et al.
2004/0133081 A1 7/2004 Teller et al.
2004/0187167 A1 9/2004 Maguire et al.
2004/0193068 A1 9/2004 Burton et al.
2004/0210159 A1 10/2004 Kibar
2004/0219184 A1 11/2004 Brown et al.
2004/0220483 A1 11/2004 Yeo et al.
2004/0236623 A1 11/2004 Gopalakrishnan
2005/0010475 A1 1/2005 Perkowski et al.
2005/0041951 A1 2/2005 Inoue et al.
2005/0043646 A1 2/2005 Viirre et al.
2005/0060312 A1 3/2005 Curtiss et al.
2005/0062637 A1 3/2005 El Zabadani et al.
2005/0071462 A1 3/2005 Bodin et al.
2005/0071865 A1 3/2005 Martins
2005/0076359 A1 4/2005 Pierson et al.
2005/0079474 A1 4/2005 Lowe
2005/0097594 A1 5/2005 O'Donnell et al.
2005/0107716 A1 5/2005 Eaton et al.
2005/0108092 A1 5/2005 Campbell et al.
2005/0113649 A1 5/2005 Bergantino
2005/0132401 A1 6/2005 Boccon-Gibod et al.
2005/0143629 A1 6/2005 Farwell
2005/0149964 A1 7/2005 Thomas et al.
2005/0154290 A1 7/2005 Langleben
2005/0165766 A1 7/2005 Szabo
2005/0177058 A1 8/2005 Sobell
2005/0197590 A1 9/2005 Osorio et al.
2005/0203798 A1 9/2005 Jensen et al.
2005/0216071 A1 9/2005 Devlin et al.
2005/0216243 A1 9/2005 Graham et al.
2005/0223237 A1 10/2005 Barletta et al.
2005/0227233 A1 10/2005 Buxton et al.
2005/0240956 A1 10/2005 Smith et al.
2005/0246002 A1 11/2005 Martinez
2005/0256905 A1 11/2005 Gruhl et al.
2005/0261980 A1 11/2005 Hadi
2005/0267798 A1 12/2005 Panara
2005/0272017 A1 12/2005 Neuhauser et al.
2005/0273017 A1 12/2005 Gordon
2005/0273802 A1 12/2005 Crystal et al.
2005/0288954 A1 12/2005 McCarthy et al.
2005/0289582 A1 12/2005 Tavares et al.
2006/0003732 A1 1/2006 Neuhauser et al.
2006/0009702 A1 1/2006 Iwaki et al.
2006/0010470 A1 1/2006 Kurosaki et al.
2006/0035707 A1 2/2006 Nguyen et al.
2006/0041548 A1 2/2006 Parsons et al.
2006/0042483 A1 3/2006 Work et al.
2006/0053110 A1 3/2006 McDonald et al.
2006/0069663 A1 3/2006 Adar et al.
2006/0093998 A1 5/2006 Vertegaal
2006/0094934 A1 5/2006 Shirai et al.
2006/0111044 A1 5/2006 Keller
2006/0111644 A1 5/2006 Guttag et al.
2006/0129458 A1 6/2006 Maggio
2006/0149337 A1 7/2006 John
2006/0167376 A1 7/2006 Viirre et al.
2006/0168613 A1 7/2006 Wood et al.
2006/0168630 A1 7/2006 Davies
2006/0176289 A1 8/2006 Horn
2006/0189886 A1 8/2006 Jones et al.
2006/0190822 A1 8/2006 Basson et al.
2006/0218046 A1 9/2006 Carfi et al.
2006/0256133 A1 11/2006 Rosenberg
2006/0257834 A1 11/2006 Lee et al.
2006/0259360 A1 11/2006 Flinn et al.
2006/0259371 A1 11/2006 Perrier et al.
2006/0293921 A1 12/2006 McCarthy et al.

(56) References Cited

U.S. PATENT DOCUMENTS

2007/0005752 A1 1/2007 Chawla et al.
2007/0016096 A1 1/2007 McNabb
2007/0038516 A1 2/2007 Apple et al.
2007/0048707 A1 3/2007 Caamano et al.
2007/0050256 A1 3/2007 Walker et al.
2007/0055169 A1 3/2007 Lee et al.
2007/0060830 A1 3/2007 Le et al.
2007/0060831 A1 3/2007 Le et al.
2007/0066874 A1 3/2007 Cook
2007/0066915 A1 3/2007 Frei et al.
2007/0066916 A1 3/2007 Lemos
2007/0067007 A1 3/2007 Schulman et al.
2007/0067305 A1 3/2007 Ives
2007/0078700 A1 4/2007 Lenzmann et al.
2007/0078706 A1 4/2007 Datta et al.
2007/0079331 A1 4/2007 Datta et al.
2007/0101360 A1 5/2007 Gutta et al.
2007/0106170 A1 5/2007 Dunseath et al.
2007/0112460 A1 5/2007 Kiselik
2007/0135727 A1 6/2007 Virtanen et al.
2007/0135728 A1 6/2007 Snyder et al.
2007/0136753 A1 6/2007 Bovenschulte et al.
2007/0150281 A1 6/2007 Hoff
2007/0150916 A1 6/2007 Begole et al.
2007/0209047 A1 9/2007 Hallberg et al.
2007/0214471 A1 9/2007 Rosenberg
2007/0225585 A1 9/2007 Washbon et al.
2007/0225674 A1 9/2007 Molnar et al.
2007/0226760 A1 9/2007 Neuhauser et al.
2007/0235716 A1 10/2007 Delic et al.
2007/0238945 A1 10/2007 Delic et al.
2007/0244977 A1 10/2007 Atkins
2007/0250846 A1 10/2007 Swix et al.
2007/0250901 A1 10/2007 McIntire et al.
2007/0265507 A1 11/2007 de Lemos
2007/0282566 A1 12/2007 Whitlow et al.
2007/0294132 A1 12/2007 Zhang et al.
2007/0294705 A1 12/2007 Gopalakrishnan et al.
2007/0294706 A1 12/2007 Neuhauser et al.
2008/0001600 A1 1/2008 deCharms
2008/0004940 A1 1/2008 Rolleston Phillips
2008/0010110 A1 1/2008 Neuhauser et al.
2008/0017883 A1 1/2008 Sarid et al.
2008/0024725 A1 1/2008 Todd
2008/0027345 A1 1/2008 Kumada et al.
2008/0040740 A1 2/2008 Plotnick et al.
2008/0043013 A1 2/2008 Gruttadauria et al.
2008/0059997 A1 3/2008 Plotnick et al.
2008/0065468 A1 3/2008 Berg et al.
2008/0065721 A1 3/2008 Cragun
2008/0081961 A1 4/2008 Westbrook et al.
2008/0082019 A1 4/2008 Ludving et al.
2008/0086356 A1 4/2008 Glassman et al.
2008/0091463 A1 4/2008 Shakamuri
2008/0091512 A1 4/2008 Marci et al.
2008/0097854 A1 4/2008 Young
2008/0109840 A1 5/2008 Walter et al.
2008/0125110 A1 5/2008 Ritter
2008/0133724 A1 6/2008 Clark
2008/0147448 A1 6/2008 McLaughlin et al.
2008/0147742 A1 6/2008 Allen
2008/0152300 A1 6/2008 Knee et al.
2008/0162182 A1 7/2008 Cazares et al.
2008/0177197 A1 7/2008 Lee et al.
2008/0195471 A1 8/2008 Dube et al.
2008/0204273 A1 8/2008 Crystal et al.
2008/0208072 A1 8/2008 Fadem et al.
2008/0214902 A1 9/2008 Lee et al.
2008/0218472 A1 9/2008 Breen et al.
2008/0221400 A1 9/2008 Lee et al.
2008/0221472 A1 9/2008 Lee et al.
2008/0221969 A1 9/2008 Lee et al.
2008/0222670 A1 9/2008 Lee et al.
2008/0222671 A1 9/2008 Lee et al.
2008/0228077 A1 9/2008 Wilk et al.
2008/0249865 A1 10/2008 Angell et al.
2008/0255949 A1 10/2008 Genco et al.
2008/0263458 A1 10/2008 Altberg et al.
2008/0295126 A1 11/2008 Lee et al.
2008/0306398 A1 12/2008 Uchiyama et al.
2009/0018996 A1 1/2009 Hunt et al.
2009/0024049 A1 1/2009 Pradeep et al.
2009/0024447 A1 1/2009 Pradeep et al.
2009/0024448 A1 1/2009 Pradeep et al.
2009/0024449 A1 1/2009 Pradeep et al.
2009/0024475 A1 1/2009 Pradeep et al.
2009/0024747 A1 1/2009 Moses et al.
2009/0025023 A1 1/2009 Pradeep et al.
2009/0025024 A1 1/2009 Beser et al.
2009/0030287 A1 1/2009 Pradeep et al.
2009/0030303 A1 1/2009 Pradeep et al.
2009/0030717 A1 1/2009 Pradeep et al.
2009/0030762 A1 1/2009 Lee et al.
2009/0030780 A1 1/2009 York et al.
2009/0030930 A1 1/2009 Pradeep et al.
2009/0036755 A1 2/2009 Pradeep et al.
2009/0036756 A1 2/2009 Pradeep et al.
2009/0037575 A1 2/2009 Crystal et al.
2009/0060240 A1 3/2009 Coughlan et al.
2009/0062629 A1 3/2009 Pradeep et al.
2009/0062679 A1 3/2009 Tan et al.
2009/0062680 A1 3/2009 Sandford
2009/0062681 A1 3/2009 Pradeep et al.
2009/0063255 A1 3/2009 Pradeep et al.
2009/0063256 A1 3/2009 Pradeep et al.
2009/0069652 A1 3/2009 Lee et al.
2009/0070798 A1 3/2009 Lee et al.
2009/0082643 A1 3/2009 Pradeep et al.
2009/0082689 A1 3/2009 Guttag et al.
2009/0082692 A1 3/2009 Hale et al.
2009/0083129 A1 3/2009 Pradeep et al.
2009/0088610 A1 4/2009 Lee et al.
2009/0089830 A1 4/2009 Chandratillake et al.
2009/0094286 A1 4/2009 Lee et al.
2009/0094627 A1 4/2009 Lee et al.
2009/0094628 A1 4/2009 Lee et al.
2009/0094629 A1 4/2009 Lee et al.
2009/0097689 A1 4/2009 Prest et al.
2009/0098524 A1 4/2009 Walton
2009/0099873 A1 4/2009 Kurple
2009/0112077 A1 4/2009 Nguyen et al.
2009/0112117 A1 4/2009 Rewari
2009/0119154 A1 5/2009 Jung et al.
2009/0131764 A1 5/2009 Lee et al.
2009/0132441 A1 5/2009 Muller et al.
2009/0133047 A1 5/2009 Lee et al.
2009/0138356 A1 5/2009 Pomplun
2009/0144780 A1 6/2009 Toebes et al.
2009/0150919 A1 6/2009 Lee et al.
2009/0150920 A1 6/2009 Jones
2009/0153328 A1 6/2009 Otani et al.
2009/0156907 A1 6/2009 Jung et al.
2009/0156955 A1 6/2009 Jung et al.
2009/0158308 A1 6/2009 Weitzenfeld et al.
2009/0163777 A1 6/2009 Jung et al.
2009/0164132 A1 6/2009 Jung et al.
2009/0171164 A1 7/2009 Jung et al.
2009/0187467 A1 7/2009 Fang et al.
2009/0195392 A1 8/2009 Zalewski
2009/0214060 A1 8/2009 Chuang et al.
2009/0216611 A1 8/2009 Leonard et al.
2009/0221928 A1 9/2009 Einav et al.
2009/0248484 A1 10/2009 Surendran et al.
2009/0248496 A1 10/2009 Hueter et al.
2009/0248594 A1 10/2009 Castleman et al.
2009/0249223 A1 10/2009 Barsook et al.
2009/0253996 A1 10/2009 Lee et al.
2009/0259137 A1 10/2009 Delic et al.
2009/0259509 A1 10/2009 Landvater
2009/0271294 A1 10/2009 Hadi
2009/0287108 A1 11/2009 Levy
2009/0292587 A1 11/2009 Fitzgerald
2009/0300672 A1 12/2009 Van Gulik
2009/0305006 A1 12/2009 Steffen

(56) References Cited

U.S. PATENT DOCUMENTS

2009/0318773 A1 12/2009 Jung et al.
2009/0318826 A1 12/2009 Green et al.
2009/0327068 A1 12/2009 Pradeep et al.
2009/0328089 A1 12/2009 Pradeep et al.
2009/0328122 A1 12/2009 Amento et al.
2010/0004977 A1 1/2010 Marci et al.
2010/0022821 A1 1/2010 Dubi et al.
2010/0030578 A1 2/2010 Siddique et al.
2010/0041962 A1 2/2010 Causevic et al.
2010/0042012 A1 2/2010 Alhussiny
2010/0060300 A1 3/2010 Muller et al.
2010/0063881 A1 3/2010 Ghosh et al.
2010/0094702 A1* 4/2010 Silberstein ......... G06Q 30/0245 705/14.43
2010/0121716 A1 5/2010 Golan
2010/0125219 A1 5/2010 Harris et al.
2010/0145176 A1 6/2010 Himes
2010/0145215 A1 6/2010 Pradeep et al.
2010/0145217 A1 6/2010 Otto et al.
2010/0153175 A1 6/2010 Pearson et al.
2010/0169153 A1 7/2010 Hwacinski et al.
2010/0169162 A1 7/2010 Anderson et al.
2010/0179881 A1 7/2010 Wiederstein
2010/0180029 A1 7/2010 Fourman
2010/0183279 A1 7/2010 Pradeep et al.
2010/0186031 A1 7/2010 Pradeep et al.
2010/0186032 A1 7/2010 Pradeep et al.
2010/0198042 A1 8/2010 Popescu et al.
2010/0211439 A1 8/2010 Marci et al.
2010/0214318 A1 8/2010 Pradeep et al.
2010/0215289 A1 8/2010 Pradeep et al.
2010/0218208 A1 8/2010 Holden
2010/0223094 A1 9/2010 Cumming et al.
2010/0228604 A1 9/2010 Desai et al.
2010/0228614 A1 9/2010 Zhang et al.
2010/0234752 A1 9/2010 Sullivan et al.
2010/0241580 A1 9/2010 Schleier-Smith
2010/0249538 A1 9/2010 Pradeep et al.
2010/0249636 A1 9/2010 Pradeep et al.
2010/0250325 A1 9/2010 Pradeep et al.
2010/0250347 A1 9/2010 Rainier et al.
2010/0250458 A1 9/2010 Ho
2010/0257052 A1 10/2010 Zito et al.
2010/0263005 A1 10/2010 White
2010/0268540 A1 10/2010 Arshi et al.
2010/0268573 A1 10/2010 Jain et al.
2010/0268720 A1 10/2010 Spivack et al.
2010/0269127 A1 10/2010 Krug
2010/0274152 A1 10/2010 McPeck et al.
2010/0274153 A1 10/2010 Tucker et al.
2010/0287152 A1 11/2010 Hauser
2010/0292998 A1 11/2010 Bodlaender et al.
2010/0306030 A1 12/2010 Mawani
2010/0306120 A1 12/2010 Ciptawilangga
2010/0317988 A1 12/2010 Terada et al.
2010/0318507 A1 12/2010 Grant et al.
2010/0325660 A1 12/2010 Holden
2010/0331661 A1 12/2010 Nakagawa
2010/0332319 A1 12/2010 Etchegoyen
2010/0332331 A1 12/2010 Etchegoyen
2011/0004089 A1 1/2011 Chou
2011/0015503 A1 1/2011 Joffe et al.
2011/0020778 A1 1/2011 Forbes
2011/0022459 A1 1/2011 Milanese et al.
2011/0022965 A1 1/2011 Lawrence et al.
2011/0040155 A1 2/2011 Guzak et al.
2011/0040202 A1 2/2011 Luo et al.
2011/0043759 A1 2/2011 Bushinsky
2011/0046473 A1 2/2011 Pradeep et al.
2011/0046502 A1 2/2011 Pradeep et al.
2011/0046503 A1 2/2011 Pradeep et al.
2011/0046504 A1 2/2011 Pradeep et al.
2011/0047035 A1 2/2011 Gidwani et al.
2011/0047121 A1 2/2011 Pradeep et al.
2011/0059422 A1 3/2011 Masaoka
2011/0071874 A1 3/2011 Schneersohn et al.
2011/0076942 A1 3/2011 Taveau et al.
2011/0084795 A1 4/2011 Fukuyori
2011/0085700 A1 4/2011 Lee
2011/0098593 A1 4/2011 Low et al.
2011/0105937 A1 5/2011 Pradeep et al.
2011/0106621 A1 5/2011 Pradeep et al.
2011/0106750 A1 5/2011 Pradeep et al.
2011/0119124 A1 5/2011 Pradeep et al.
2011/0119129 A1 5/2011 Pradeep et al.
2011/0119130 A1 5/2011 Agan et al.
2011/0131274 A1 6/2011 Hille
2011/0144519 A1 6/2011 Causevic
2011/0153390 A1 6/2011 Harris
2011/0153391 A1 6/2011 Tenbrock
2011/0208515 A1 8/2011 Neuhauser
2011/0224569 A1 9/2011 Isenhart et al.
2011/0237923 A1 9/2011 Picht et al.
2011/0237971 A1 9/2011 Pradeep et al.
2011/0248729 A2 10/2011 Mueller et al.
2011/0257502 A1 10/2011 Lee
2011/0257937 A1 10/2011 Lee
2011/0270620 A1 11/2011 Pradeep et al.
2011/0276504 A1 11/2011 Pradeep et al.
2011/0282231 A1 11/2011 Pradeep et al.
2011/0282232 A1 11/2011 Pradeep et al.
2011/0282749 A1 11/2011 Pradeep et al.
2011/0298706 A1 12/2011 Mann
2011/0319975 A1 12/2011 Ho et al.
2012/0002848 A1 1/2012 Hill
2012/0004899 A1 1/2012 Arshi
2012/0022391 A1 1/2012 Leuthardt
2012/0036004 A1 2/2012 Pradeep et al.
2012/0036005 A1 2/2012 Pradeep et al.
2012/0046993 A1 2/2012 Hill
2012/0054018 A1 3/2012 Pradeep et al.
2012/0072289 A1 3/2012 Pradeep et al.
2012/0083668 A1 4/2012 Pradeep et al.
2012/0084139 A1 4/2012 Pradeep et al.
2012/0108995 A1 5/2012 Pradeep et al.
2012/0114305 A1 5/2012 Holden
2012/0130800 A1 5/2012 Pradeep et al.
2012/0173701 A1 7/2012 Tenbrock
2012/0203363 A1 8/2012 Mckenna et al.
2012/0203559 A1 8/2012 Mckenna et al.
2012/0239407 A1 9/2012 Lynch et al.
2012/0245978 A1 9/2012 Jain et al.
2012/0284112 A1 11/2012 Pradeep et al.
2012/0284332 A1 11/2012 Pradeep et al.
2012/0290409 A1 11/2012 Pradeep et al.
2013/0022948 A1 1/2013 Angell et al.
2013/0024272 A1 1/2013 Pradeep et al.
2013/0046577 A1 2/2013 Marci et al.
2013/0094722 A1 4/2013 Hill
2013/0097715 A1 4/2013 Fourman
2013/0124365 A1 5/2013 Pradeep
2013/0124623 A1 5/2013 Munter
2013/0152506 A1 6/2013 Pradeep
2013/0166373 A1 6/2013 Pradeep et al.
2013/0185140 A1 7/2013 Pradeep et al.
2013/0185141 A1 7/2013 Pradeep et al.
2013/0185142 A1 7/2013 Pradeep et al.
2013/0185144 A1 7/2013 Pradeep et al.
2013/0185145 A1 7/2013 Pradeep et al.
2013/0268279 A1 10/2013 Srinivasan et al.
2013/0304540 A1 11/2013 Pradeep et al.
2013/0332259 A1 12/2013 Pradeep et al.
2014/0162225 A1 6/2014 Hill
2014/0244345 A1 8/2014 Sollis et al.
2017/0039591 A1 2/2017 Knight et al.
2018/0247332 A1 8/2018 Pradeep et al.
2018/0341977 A1 11/2018 Knight et al.
2019/0005532 A1 1/2019 Pradeep et al.
2019/0034958 A1 1/2019 Pradeep et al.
2019/0034959 A1 1/2019 Pradeep et al.
2019/0139078 A1 5/2019 Pradeep et al.
2019/0156352 A1 5/2019 Pradeep et al.
2019/0220888 A1 7/2019 Knight et al.
2020/0005339 A1 1/2020 Pradeep et al.

(56) References Cited

U.S. PATENT DOCUMENTS

| | | | |
|---|---|---|---|
| 2020/0163571 | A1 | 5/2020 | Pradeep et al. |
| 2020/0211033 | A1 | 7/2020 | Pradeep et al. |
| 2020/0234329 | A1 | 7/2020 | Pradeep et al. |
| 2020/0258116 | A1 | 8/2020 | Pradeep et al. |
| 2020/0364741 | A1 | 11/2020 | Pradeep et al. |

FOREIGN PATENT DOCUMENTS

| | | |
|---|---|---|
| GB | 1374658 | 11/1974 |
| GB | 2221759 | 2/1990 |
| JP | 2001147944 | 5/2001 |
| JP | 2005051654 | 2/2005 |
| JP | 2005160805 | 6/2005 |
| JP | 2006006355 | 1/2006 |
| JP | 2006227994 | 8/2006 |
| JP | 2006305334 | 11/2006 |
| JP | 2007310454 | 11/2007 |
| KR | 200422399 | 7/2006 |
| WO | 95-018565 | 7/1995 |
| WO | 1997017774 | 5/1997 |
| WO | 1997040745 | 11/1997 |
| WO | 1997041673 | 11/1997 |
| WO | 02100241 | 12/2002 |
| WO | 02102238 | 12/2002 |
| WO | 2004049225 | 6/2004 |
| WO | 2006009771 | 1/2006 |
| WO | 2008030831 | 3/2008 |
| WO | 2008055078 | 5/2008 |
| WO | 2008064431 | 6/2008 |
| WO | 2008072739 | 6/2008 |
| WO | 2008077178 | 7/2008 |
| WO | 2008109694 | 9/2008 |
| WO | 2008109699 | 9/2008 |
| WO | 2008121651 | 10/2008 |
| WO | 2008137579 | 11/2008 |
| WO | 2008137581 | 11/2008 |
| WO | 2008141340 | 11/2008 |
| WO | 2008154410 | 12/2008 |
| WO | 2009018374 | 2/2009 |
| WO | 2009052833 | 4/2009 |
| WO | 2011055291 | 5/2011 |
| WO | 2011056679 | 5/2011 |

OTHER PUBLICATIONS

Office Action, issued by the United States Patent and Trademark Office in connection with U.S. Appl. No. 12/056,211, dated Jan. 7, 2011, 19 pages.
Office Action issued by the United States Patent and Trademark Office in connection with U.S. Appl. No. 12/056,221, dated Apr. 15, 2011, 24 pages.
Final Rejection, issued by the United States Patent and Trademark Office in connection with U.S. Appl. No. 12/113,863, dated Jun. 9, 2011, 12 pages.
Office Action, issued by the United States Patent and Trademark Office in connection with U.S. Appl. No. 12/113,863, dated Dec. 27, 2010, 15 pages.
Final Rejection, issued by the United States Patent and Trademark Office in connection with U.S. Appl. No. 12/113,870, dated Apr. 21, 2011, 10 pages.
Office Action, issued by the United States Patent and Trademark Office in connection with U.S. Appl. No. 12/113,870, dated Dec. 3, 2010, 12 pages.
Office Action, issued by the United States Patent and Trademark Office in connection with U.S. Appl. No. 12/122,240, dated Jun. 10, 2011, 12 pages.
Final Rejection, issued by the United States Patent and Trademark Office in connection with U.S. Appl. No. 12/122,262, dated May 26, 2011, 15 pages.
Office Action, issued by the United States Patent and Trademark Office in connection with U.S. Appl. No. 12/122,262, dated Dec. 9, 2010, 13 pages.
Final Rejection, issued by the United States Patent and Trademark Office in connection with U.S. Appl. No. 12/135,066, dated Jan. 21, 2011, 16 pages.
Office Action, issued by the United States Patent and Trademark Office in connection with U.S. Appl. No. 12/135,066, dated Oct. 28, 2010, 14 pages.
Notice of Panel Decision from Pre-Appeal Brief Review, issued by the United States Patent and Trademark Office in connection with U.S. Appl. No. 12/135,066, dated May 31, 2011, 2 pages.
Office Action, issued by the United States Patent and Trademark Office in connection with U.S. Appl. No. 12/135,074, dated Dec. 23, 2010, 14 pages.
Final Rejection, issued by the United States Patent and Trademark Office in connection with U.S. Appl. No. 12/135,074, dated Jun. 9, 2011, 10 pages.
Final Rejection, issued by the United States Patent and Trademark Office in connection with U.S. Appl. No. 12/182,874, dated Jul. 7, 2011, 14 pages.
Office Action, issued by the United States Patent and Trademark Office in connection with U.S. Appl. No. 12/182,874, dated Dec. 27, 2010, 17 pages.
Office Action, issued by the United States Patent and Trademark Office in connection with U.S. Appl. No. 12/199,557, dated Dec. 27, 2010, 14 pages.
Final Rejection, issued by the United States Patent and Trademark Office in connection with U.S. Appl. No. 12/199,557, dated Jun. 9, 2011, 12 pages.
Final Rejection, issued by the United States Patent and Trademark Office in connection with U.S. Appl. No. 12/199,583, dated Jun. 21, 2011, 14 pages.
Office Action, issued by the United States Patent and Trademark Office in connection with U.S. Appl. No. 12/199,583, dated Dec. 27, 2010, 17 pages.
Final Rejection, issued by the United States Patent and Trademark Office in connection with U.S. Appl. No. 12/199,596, dated Jun. 14, 2011, 13 pages.
Office Action, issued by the United States Patent and Trademark Office in connection with U.S. Appl. No. 12/199,596, dated Dec. 27, 2010, 17 pages.
Final Rejection, issued by the United States Patent and Trademark Office in connection with U.S. Appl. No. 12/200,813, dated Jul. 6, 2011, 13 pages.
Office Action, issued by the United States Patent and Trademark Office in connection with U.S. Appl. No. 12/200,813, dated Dec. 27, 2010, 14 pages.
Office Action, issued by the United States Patent and Trademark Office in connection with U.S. Appl. No. 12/234,372, dated Jun. 7, 2011, 10 pages.
Final Rejection, issued by the United States Patent and Trademark Office in connection with U.S. Appl. No. 12/135,069, dated Feb. 17, 2011, 32 pages.
Office Action, issued by the United States Patent and Trademark Office in connection with U.S. Appl. No. 12/135,069, dated Oct. 29, 2010, 21 pages.
Office Action, issued by the United States Patent and Trademark Office in connection with U.S. Appl. No. 12/357,315, dated May 4, 2011, 9 pages.
Office Action, issued by the United States Patent and Trademark Office in connection with U.S. Appl. No. 12/410,380, dated Jun. 7, 2011, 9 pages.
Office Action, issued by the United States Patent and Trademark Office in connection with U.S. Appl. No. 12/413,297, dated Jul. 18, 2011, 9 pages.
Office Action, issued by the United States Patent and Trademark Office in connection with U.S. Appl. No. 12/608,685, dated Jul. 12, 2011, 15 pages.
Office Action, issued by the United States Patent and Trademark Office in connection with U.S. Appl. No. 12/056,190, dated Aug. 10, 2011, 28 pages.
Office Action, issued by the United States Patent and Trademark Office in connection with U.S. Appl. No. 12/357,322, dated Aug. 23, 2011, 12 pages.

(56) References Cited

OTHER PUBLICATIONS

Office Action, issued by the United States Patent and Trademark Office in connection with U.S. Appl. No. 12/135,069, dated Aug. 26, 2011, 33 pages.
Restriction Requirement, issued by the United States Patent and Trademark Office in connection with U.S. Appl. No. 12/122,253, dated Sep. 2, 2011, 7 pages.
Office Action, issued by the United States Patent and Trademark Office in connection with U.S. Appl. No. 12/410,372, dated Sep. 12, 2011, 12 pages.
Restriction Requirement, issued by the United States Patent and Trademark Office in connection with U.S. Appl. No. 12/182,851, dated Sep. 12, 2011, 7 pages.
Office Action, issued by the United States Patent and Trademark Office in connection with U.S. Appl. No. 12/135,066, dated Sep. 29, 2011, 37 pages.
Restriction Requirement, issued by the United States Patent and Trademark Office in connection with U.S. Appl. No. 12/056,225, dated Oct. 3, 2011, 6 pages.
Office Action, issued by the United States Patent and Trademark Office in connection with U.S. Appl. No. 12/234,388, dated Oct. 12, 2011, 27 pages.
Office Action, issued by the United States Patent and Trademark Office in connection with U.S. Appl. No. 12/234,372, dated Oct. 13, 2011, 22 pages.
Office Action, issued by the United States Patent and Trademark Office in connection with U.S. Appl. No. 12/410,380, dated Oct. 19, 2011, 21 pages.
Office Action, issued by the United States Patent and Trademark Office in connection with U.S. Appl. No. 12/357,315, dated Oct. 26, 2011, 41 pages.
Office Action, issued by the United States Patent and Trademark Office in connection with U.S. Appl. No. 12/122,240, dated Oct. 27, 2011, 39 pages.
Final Rejection, issued by the United States Patent and Trademark Office in connection with U.S. Appl. No. 12/056,221, dated Nov. 28, 2011, 44 pages.
Office Action, issued by the United States Patent and Trademark Office in connection with U.S. Appl. No. 12/608,660, dated Dec. 7, 2011, 8 pages.
Office Action, issued by the United States Patent and Trademark Office in connection with U.S. Appl. No. 12/113,863, dated Dec. 22, 2011, 17 pages.
Office Action, issued by the United States Patent and Trademark Office in connection with U.S. Appl. No. 12/122,262, dated Dec. 22, 2011, 17 pages.
Office Action, issued by the United States Patent and Trademark Office in connection with U.S. Appl. No. 12/135,074, dated Dec. 22, 2011, 16 pages.
Office Action, issued by the United States Patent and Trademark Office in connection with U.S. Appl. No. 12/199,557, dated Dec. 22, 2011, 17 pages.
Office Action, issued by the United States Patent and Trademark Office in connection with U.S. Appl. No. 12/199,596, dated Dec. 22, 2011, 15 pages.
Office Action, issued by the United States Patent and Trademark Office in connection with U.S. Appl. No. 12/200,813, dated Dec. 22, 2011, 18 pages.
Office Action, issued by the United States Patent and Trademark Office in connection with U.S. Appl. No. 12/199,583, dated Dec. 29, 2011, 18 pages.
Final Rejection, issued by the United States Patent and Trademark Office in connection with U.S. Appl. No. 12/410,372, dated Jan. 3, 2012, 10 pages.
Final Rejection, issued by the United States Patent and Trademark Office in connection with U.S. Appl. No. 12/413,297, dated Jan. 4, 2012, 10 pages.
Office Action, issued by the United States Patent and Trademark Office in connection with U.S. Appl. No. 12/544,921, dated Jan. 9, 2012, 13 pages.
Office Action, issued by the United States Patent and Trademark Office in connection with U.S. Appl. No. 12/357,302, dated Jan. 17, 2012, 11 pages.
Office Action, issued by the United States Patent and Trademark Office in connection with U.S. Appl. No. 12/056,225, dated Jan. 20, 2012, 12 pages.
Final Rejection, issued by the United States Patent and Trademark Office in connection with U.S. Appl. No. 12/135,066, dated Jan. 24, 2012, 12 pages.
Office Action, issued by the United States Patent and Trademark Office in connection with U.S. Appl. No. 12/546,586, dated Feb. 1, 2012, 17 pages.
Restriction Requirement, issued by the United States Patent and Trademark Office in connection with U.S. Appl. No. 12/544,958, dated Feb. 10, 2012, 6 pages.
Final Rejection, issued by the United States Patent and Trademark Office in connection with U.S. Appl. No. 12/135,069, dated Feb. 14, 2012, 36 pages.
Final Rejection, issued by the United States Patent and Trademark Office in connection with U.S. Appl. No. 12/357,322, dated Feb. 14, 2012, 14 pages.
Office Action, issued by the United States Patent and Trademark Office in connection with U.S. Appl. No. 12/056,211, dated Feb. 16, 2012, 16 pages.
Final Rejection, issued by the United States Patent and Trademark Office in connection with U.S. Appl. No. 12/056,190, dated Feb. 17, 2012, 22 pages.
Office Action, issued by the United States Patent and Trademark Office in connection with U.S. Appl. No. 12/122,253, dated Feb. 17, 2012, 20 pages.
Office Action, issued by the United States Patent and Trademark Office in connection with U.S. Appl. No. 12/182,874, dated Feb. 17, 2012, 15 pages.
Office Action, issued by the United States Patent and Trademark Office in connection with U.S. Appl. No. 12/868,531, dated Mar. 1, 2012, 7 pages.
Office Action, issued by the United States Patent and Trademark Office in connection with U.S. Appl. No. 12/182,851, dated Mar. 14, 2012, 17 pages.
Office Action, issued by the United States Patent and Trademark Office in connection with U.S. Appl. No. 12/608,685, dated Mar. 29, 2012, 17 pages.
Office Action, issued by the United States Patent and Trademark Office in connection with U.S. Appl. No. 12/846,242, dated Mar. 29, 2012, 16 pages.
Office Action, issued by the United States Patent and Trademark Office in connection with U.S. Appl. No. 12/234,388, dated Apr. 6, 2012, 6 pages.
Office Action, issued by the United States Patent and Trademark Office in connection with U.S. Appl. No. 12/357,315, dated Apr. 9, 2012, 17 pages.
Office Action, issued by the United States Patent and Trademark Office in connection with U.S. Appl. No. 12/544,958, dated May 2, 2012, 15 pages.
Notice of Allowance, issued by the United States Patent and Trademark Office in connection with U.S. Appl. No. 12/357,302, dated May 7, 2012, 11 pages.
Notice of Allowance, issued by the United States Patent and Trademark Office in connection with U.S. Appl. No. 12/868,531, dated May 8, 2012, 11 pages.
Notice of Allowance, issued by the United States Patent and Trademark Office in connection with U.S. Appl. No. 12/608,696, dated May 15, 2012, 6 pages.
Restriction Requirement, issued by the United States Patent and Trademark Office in connection with U.S. Appl. No. 12/545,455, dated Jun. 13, 2012, 5 pages.
Office Action, issued by the United States Patent and Trademark Office in connection with U.S. Appl. No. 12/056,225, dated Jun. 15, 2012, 9 pages.
Office Action, issued by the United States Patent and Trademark Office in connection with U.S. Appl. No. 12/544,934, dated Jun. 18, 2012, 11 pages.

(56) References Cited

OTHER PUBLICATIONS

Office Action, issued by the United States Patent and Trademark Office in connection with U.S. Appl. No. 12/135,066, dated Jun. 21, 2012, 10 pages.
Final Rejection, issued by the United States Patent and Trademark Office in connection with U.S. Appl. No. 12/608,660, dated Jul. 10, 2012, 14 pages.
Final Rejection, issued by the United States Patent and Trademark Office in connection with U.S. Appl. No. 12/608,685, dated Jul. 30, 2012, 15 pages.
Examiner's Answer, issued by the United States Patent and Trademark Office in connection with U.S. Appl. No. 12/410,372, dated Aug. 3, 2012, 8 pages.
Examiner's Answer, issued by the United States Patent and Trademark Office in connection with U.S. Appl. No. 12/410,380, dated Jun. 8, 2012, 12 pages.
Examiner's Answer, issued by the United States Patent and Trademark Office in connection with U.S. Appl. No. 12/234,372, dated May 23, 2012, 11 pages.
Advisory Action, issued by the United States Patent and Trademark Office in connection with U.S. Appl. No. 12/234,388, dated Aug. 28, 2012, 3 pages.
Office Action, issued by the United States Patent and Trademark Office in connection with U.S. Appl. No. 12/545,455, dated Aug. 29, 2012, 11 pages.
Office Action, issued by the United States Patent and Trademark Office in connection with U.S. Appl. No. 12/778,828, dated Aug. 30, 2012, 9 pages.
Office Action, issued by the United States Patent and Trademark Office in connection with U.S. Appl. No. 12/778,810, dated Aug. 31, 2012, 12 pages.
Notice of Allowance, issued by the United States Patent and Trademark Office in connection with U.S. Appl. No. 12/056,190, dated Sep. 17, 2012, 11 pages.
Notice of Allowance, issued by the United States Patent and Trademark Office in connection with U.S. Appl. No. 12/122,262, dated Sep. 17, 2012, 11 pages.
Final Rejection, issued by the United States Patent and Trademark Office in connection with U.S. Appl. No. 12/122,253, dated Sep. 17, 2012, 17 pages.
Examiner's Answer, issued by the United States Patent and Trademark Office in connection with U.S. Appl. No. 12/413,297, dated Sep. 18, 2012, 18 pages.
Final Rejection, issued by the United States Patent and Trademark Office in connection with U.S. Appl. No. 12/546,586, dated Sep. 18, 2012, 17 pages.
Notice of Allowance, issued by the United States Patent and Trademark Office in connection with U.S. Appl. No. 12/056,211, dated Sep. 19, 2012, 10 pages.
Notice of Allowance, issued by the United States Patent and Trademark Office in connection with U.S. Appl. No. 12/135,074, dated Sep. 19, 2012, 10 pages.
Notice of Allowance, issued by the United States Patent and Trademark Office in connection with U.S. Appl. No. 12/853,213, dated Sep. 7, 2012, 9 pages.
Notice of Allowance, issued by the United States Patent and Trademark Office in connection with U.S. Appl. No. 12/199,583, dated Sep. 26, 2012, 14 pages.
Notice of Allowance, issued by the United States Patent and Trademark Office in connection with U.S. Appl. No. 12/199,596, dated Sep. 27, 2012, 14 pages.
Notice of Allowance, issued by the United States Patent and Trademark Office in connection with U.S. Appl. No. 12/199,557, dated Sep. 28, 2012, 12 pages.
Notice of Allowance, issued by the United States Patent and Trademark Office in connection with U.S. Appl. No. 12/113,863, dated Oct. 1, 2012, 12 pages.
Office Action, issued by the United States Patent and Trademark Office in connection with U.S. Appl. No. 13/444,149, dated Oct. 4, 2012, 9 pages.
Final Office Action, issued by the United States Patent and Trademark Office in connection with U.S. Appl. No. 12/182,851, dated Oct. 4, 2012, 14 pages.
Office Action, issued by the United States Patent and Trademark Office in connection with U.S. Appl. No. 12/234,388, dated Oct. 5, 2012, 6 pages.
Notice of Allowance, issued by the United States Patent and Trademark Office in connection with U.S. Appl. No. 12/853,197, dated Oct. 16, 2012, 5 pages.
Notice of Allowance, issued by the United States Patent and Trademark Office in connection with U.S. Appl. No. 12/868,531, dated Oct. 22, 2012, 5 pages.
Final Office Action, issued by the United States Patent and Trademark Office in connection with U.S. Appl. No. 12/846,242, dated Nov. 29, 2012, 14 pages.
Notice of Allowance, issued by the United States Patent and Trademark Office in connection with U.S. Appl. No. 12/200,813, dated Oct. 30, 2012, 5 pages.
Notice of Allowance, issued by the United States Patent and Trademark Office in connection with U.S. Appl. No. 12/056,190, dated Nov. 2, 2012, 5 pages.
Restriction Requirement, issued by the United States Patent and Trademark Office in connection with U.S. Appl. No. 12/056,225, dated Nov. 2, 2012, 5 pages.
Final Office Action, issued by the United States Patent and Trademark Office in connection with U.S. Appl. No. 12/135,066, dated Nov. 13, 2012, 9 pages.
Notice of Allowance, issued by the United States Patent and Trademark Office in connection with U.S. Appl. No. 12/113,863, dated Nov. 16, 2012, 5 pages.
Notice of Allowance, issued by the United States Patent and Trademark Office in connection with U.S. Appl. No. 12/056,211, dated Nov. 21, 2012, 5 pages.
Notice of Allowance, issued by the United States Patent and Trademark Office in connection with U.S. Appl. No. 12/868,531, dated Nov. 23, 2012, 5 pages.
Office Action, issued by the United States Patent and Trademark Office in connection with U.S. Appl. No. 12/913,102, dated Dec. 7, 2012, 7 pages.
Final Office Action, issued by the United States Patent and Trademark Office in connection with U.S. Appl. No. 12/544,958, dated Dec. 10, 2012, 16 pages.
Notice of Allowance, issued by the United States Patent and Trademark Office in connection with U.S. Appl. No. 12/853,197, dated Dec. 20, 2012, 5 pages.
Notice of Allowance, issued by the United States Patent and Trademark Office in connection with U.S. Appl. No. 12/056,190, dated Dec. 21, 2012, 14 pages.
Notice of Allowance, issued by the United States Patent and Trademark Office in connection with U.S. Appl. No. 12/056,211, dated Dec. 21, 2012, 10 pages.
Notice of Allowance, issued by the United States Patent and Trademark Office in connection with U.S. Appl. No. 12/122,262, dated Dec. 21, 2012, 19 pages.
Notice of Allowance, issued by the United States Patent and Trademark Office in connection with U.S. Appl. No. 12/135,074, dated Dec. 21, 2012, 12 pages.
Notice of Allowance, issued by the United States Patent and Trademark Office in connection with U.S. Appl. No. 12/199,557, dated Dec. 21, 2012, 14 pages.
Notice of Allowance, issued by the United States Patent and Trademark Office in connection with U.S. Appl. No. 12/199,596, dated Dec. 21, 2012, 17 pages.
Notice of Allowance, issued by the United States Patent and Trademark Office in connection with U.S. Appl. No. 12/200,813, dated Dec. 21, 2012, 9 pages.
Notice of Allowance, issued by the United States Patent and Trademark Office in connection with U.S. Appl. No. 12/853,213, dated Dec. 21, 2012, 10 pages.
Notice of Allowance, issued by the United States Patent and Trademark Office in connection with U.S. Appl. No. 12/868,531, dated Dec. 26, 2012, 2 pages.

(56) References Cited

OTHER PUBLICATIONS

Notice of Allowance, issued by the United States Patent and Trademark Office in connection with U.S. Appl. No. 12/113,863, dated Dec. 31, 2012, 5 pages.
Notice of Allowance, issued by the United States Patent and Trademark Office in connection with U.S. Appl. No. 12/199,583, dated Dec. 31, 2012, 10 pages.
Final Office Action, issued by the United States Patent and Trademark Office in connection with U.S. Appl. No. 12/182,874, dated Jan. 4, 2013, 17 pages.
Notice of Allowance, issued by the United States Patent and Trademark Office in connection with U.S. Appl. No. 12/199,583, dated Jan. 11, 2013, 11 pages.
Final Office Action, issued by the United States Patent and Trademark Office in connection with U.S. Appl. No. 12/056,225, dated Jan. 11, 2013, 11 pages.
Recertified IDS and Interview Summary, issued by the United States Patent and Trademark Office in connection with U.S. Appl. No. 12/853,197, dated Jan. 16, 2013, 6 pages.
Notice of Allowance, issued by the United States Patent and Trademark Office in connection with U.S. Appl. No. 12/199,557, dated Jan. 29, 2013, 17 pages.
Notice of Allowance, issued by the United States Patent and Trademark Office in connection with U.S. Appl. No. 12/853,197, dated Jan. 29, 2013, 11 pages.
Notice of Allowance, issued by the United States Patent and Trademark Office in connection with U.S. Appl. No. 12/056,190, dated Jan. 31, 2013, 5 pages.
Notice of Allowance, issued by the United States Patent and Trademark Office in connection with U.S. Appl. No. 12/113,863, dated Jan. 31, 2013, 5 pages.
Notice of Allowance, issued by the United States Patent and Trademark Office in connection with U.S. Appl. No. 12/135,074, dated Jan. 31, 2013, 10 pages.
Notice of Allowance, issued by the United States Patent and Trademark Office in connection with U.S. Appl. No. 12/199,583, dated Feb. 1, 2013, 11 pages.
Notice of Allowance, issued by the United States Patent and Trademark Office in connection with U.S. Appl. No. 12/200,813, dated Feb. 1, 2013, 5pages.
Notice of Allowance, issued by the United States Patent and Trademark Office in connection with U.S. Appl. No. 12/056,211, dated Feb. 4, 2013, 5 pages.
Notice of Allowance, issued by the United States Patent and Trademark Office in connection with U.S. Appl. No. 12/122,262, dated Feb. 5, 2013, 15 pages.
Notice of Allowance, issued by the United States Patent and Trademark Office in connection with U.S. Appl. No. 12/868,531, dated Feb. 5, 2013, 8 pages.
Notice of Allowance, issued by the United States Patent and Trademark Office in connection with U.S. Appl. No. 12/853,213, dated Feb. 5, 2013, 10 pages.
Notice of Allowance, issued by the United States Patent and Trademark Office in connection with U.S. Appl. No. 12/234,388, dated Feb. 15, 2013, 9 pages.
Notice of Allowance, issued by the United States Patent and Trademark Office in connection with U.S. Appl. No. 12/056,190, dated Feb. 14, 2013, 5 pages.
Notice of Allowance, issued by the United States Patent and Trademark Office in connection with U.S. Appl. No. 12/200,813, dated Sep. 20, 2012, 11 pages.
Notice of Allowance, issued by the United States Patent and Trademark Office in connection with U.S. Appl. No. 12/182,874, dated Apr. 16, 2013, 10 pages.
Notice of Allowance, issued by the United States Patent and Trademark Office in connection with U.S. Appl. No. 12/182,874, dated Apr. 22, 2013, 11 pages.
International Preliminary Report on Patentability, issued by the International Bureau of WIPO in connection with International Application No. PCT/US08/058264, dated Sep. 29, 2009, 1 page.
International Search Report, issued by the International Searching Authority in connection with International Application No. PCT/US08/058264, dated Aug. 1, 2008, 2 pages.
Written Opinion, issued by the International Searching Authority in connection with International Application No. PCT/US08/058264, dated Aug. 1, 2008, 5 pages.
International Preliminary Report on Patentability, issued by the International Bureau of WIPO in connection with International Application No. PCT/US08/062273, dated Nov. 3, 2009, 1 page.
International Search Report, issued by the International Searching Authority in connection with International Application No. PCT/US08/062273, dated Sep. 5, 2008, 2 pages.
Written Opinion, issued by the International Searching Authority in connection with International Application No. PCT/US08/062273, dated Sep. 5, 2008, 4 pages.
International Search Report, issued by the International Searching Authority in connection with International Application No. PCT/US08/062275, dated Sep. 22, 2008, 2 pages.
Written Opinion, issued by the International Searching Authority in connection with International Application No. PCT/US08/062275, dated Sep. 22, 2008, 6 pages.
International Preliminary Report on Patentability, issued by the International Bureau of WIPO in connection with International Application No. PCT/US08/063984, dated Nov. 17, 2009, 1 page.
International Search Report, issued by the International Searching Authority in connection with International Application No. PCT/US08/063984, dated Sep. 29, 2008, 3 pages.
Written Opinion, issued by the International Searching Authority in connection with International Application No. PCT/US08/063984, dated Sep. 29, 2008, 4 pages.
International Preliminary Report on Patentability, issued by the International Bureau of WIPO in connection with International Application No. PCT/US08/063989, dated Nov. 17, 2009, 1 page.
International Search Report, issued by the International Searching Authority in connection with International Application No. PCT/US08/063989, dated Jul. 17, 2008, 2 pages.
Written Opinion, issued by the International Searching Authority in connection with International Application No. PCT/US08/063989, dated Jul. 17, 2008, 4 pages.
International Preliminary Report on Patentability, issued by the International Bureau of WIPO in connection with International Application No. PCT/US08/066166, dated Dec. 7, 2009, 1 page.
International Search Report, issued by the International Searching Authority in connection with International Application No. PCT/US08/066166, dated Aug. 25, 2008, 2 pages.
Written Opinion, issued by the International Searching Authority in connection with International Application No. PCT/US08/066166, dated Aug. 25, 2008, 6 pages.
International Preliminary Report on Patentability, issued by the International Bureau of WIPO in connection with International Application No. PCT/US08/071639, dated Feb. 2, 2010, 1 page.
Written Opinion, issued by the International Searching Authority in connection with International Application No. PCT/US08/071639, dated Oct. 22, 2008, 4 pages.
International Preliminary Report on Patentability, issued by the International Bureau of WIPO in connection with International Application No. PCT/US08/074467, dated Mar. 2, 2010, 1 page.
International Search Report, issued by the International Searching Authority in connection with International Application No. PCT/US08/074467, dated Nov. 17, 2008, 2 pages.
Written Opinion, issued by the International Searching Authority in connection with International Application No. PCT/US08/074467, dated Nov. 17, 2008, 4 pages.
International Preliminary Report of Patentability, issued by the International Bureau in connection with International Application No. PCT/US10/021535, dated Jul. 26, 2011, 1 page.
International Search Report, issued by the International Searching Authority in connection with International Application No. PCT/US10/021535, dated Mar. 23, 2010, 3 pages.
Written Opinion, issued by the International Searching Authority in connection with International Application No. PCT/US10/021535, dated Mar. 23, 2010, 4 pages.

(56) References Cited

OTHER PUBLICATIONS

International Preliminary Report of Patentability, issued by the International Bureau in connection with International Application No. PCT/US09/065368, dated Jun. 23, 2011, 2 pages.
International Search Report, issued by the International Searching Authority in connection with International Application No. PCT/US09/065368, dated Jan. 21, 2010, 3 pages.
Written Opinion, issued by the International Searching Authority in connection with International Application No. PCT/US09/065368, dated Jan. 21, 2010, 7 pages.
International Preliminary Report on Patentability, issued by the International Bureau of WIPO in connection with International Application No. PCT/US08/062275, dated Nov. 3, 2009, 1 page.
International Search Report, issued by the International Searching Authority in connection with International Application No. PCT/US08/071639, dated Oct. 22, 2008, 3 pages.
Extended European Search Report, issued by the European Patent Office in connection with European Application No. 08744383.4-2221/2130146, dated Jul. 27, 2011, 6 pages.
Extended European Search Report, issued by the European Patent Office in connection with European Application No. 10173095.0-2221, dated Dec. 17, 2010, 3 pages.
Extended European Search Report, issued by the European Patent Office in connection with European Application No. 10189294.1-2221, dated Mar. 21, 2011, 7 pages.
First Office Action, issued by the State Intellectual Property Office of P.R. China in connection with Patent Application No. 200880104982.1, dated Jan. 25, 2011, 15 pages (includes English translation).
English Translation of First Office Action, issued by the State Intellectual Property Office of P.R. China in connection with Patent Application No. 2008801015007, dated May 25, 2011, 8 pages.
English Translation of First Office Action, issued by the State Intellectual Property Office of P.R. China in connection with Patent Application No. 200880019166.0, dated Jul. 22, 2011, 16 pages.
English Translation of Decision of Rejection, issued by the State Intellectual Property Office of P.R. China in connection with Patent Application No. 200880104982.1, dated Sep. 23, 2011, 10 pages.
Extended European Search Report, issued by the European Patent Office in connection with European Application No. 11006934.1-2221, dated Oct. 25, 2011, 5 pages.
English Translation of First Office Action, issued by the State Intellectual Property Office of P.R. China in connection with Patent Application No. 20080017883.X, dated Nov. 30, 2011, 16 pages.
English Translation of Office Action, issued by the Israel Patent Office in connection with Patent Application No. 203176, dated Feb. 21, 2012, 2 pages.
English Translation of Office Action, issued by the Israel Patent Office in connection with Patent Application No. 203177, dated Mar. 1, 2012, 2 pages.
English Translation of Second Office Action, issued by the State Intellectual Property Office of P.R. China in connection with Patent Application No. 200880101500.7, dated Apr. 5, 2012, 5 pages.
English Translation of Second Office Action, issued by the State Intellectual Property Office of P.R. China in connection with Patent Application No. 200880019166.0, dated Jun. 5, 2012, 8 pages.
English Translation of Second Office Action, issued by the State Intellectual Property Office of P.R. China in connection with Patent Application No. 200880104982.1, dated Jun. 29, 2012, 5 pages.
English Translation of Second Office Action, issued by the State Intellectual Property Office of P.R. China in connection with Patent Application No. 200880017883.X, dated Aug. 10, 2012, 9 pages.
English Translation of Office Action, issued by the Israel Patent Office in connection with Patent Application No. 203176, dated Sep. 27, 2012, 1 pages.
English Translation of Office Action, issued by the Israel Patent Office in connection with Patent Application No. 203177, dated Sep. 27, 2012, 1 page.
Office Action, issued by the Japanese Patent Office in connection with Patent Application No. 2010-501190, dated Oct. 2, 2012, 10 pages. (includes English translation).
English Translation of Office Action, issued by the Japanese Patent Office in connection with Patent Application No. 2010-506646, dated Oct. 23, 2012, 3 pages.
English Translation of Third Office Action, issued by the State Intellectual Property Office of P.R. China in connection with Patent Application No. 200880101500.7, dated Nov. 21, 2012, 5 pages.
English Translation of Office Action, issued by the Israeli Patent Office in connection with Patent Application No. 201187, dated Nov. 27, 2012, 2 pages.
Extended European Search Report, issued by the European Patent Office in connection with European Application No. 08796890.5-2319/2170161, dated Dec. 7, 2012, 9 pages.
Notification to Grant Patent Right for Invention, issued by the State Intellectual Property Office of P.R. China in connection with Patent Application No. 200880104982.1, dated Jan. 14, 2013, 4 pages. (includes English translation).
Extended European Search Report, issued by the European Patent Office in connection with European Application No. 08770372.4-1265/2152155, dated Feb. 6, 2013, 7 pages.
English Translation of Third Office Action, issued by the State Intellectual Property Office of P.R. China in connection with Patent Application No. 200880017883.X, dated Mar. 18, 2013, 8 pages.
English translation of Notification to Grant Patent Right for Invention, issued by the State Intellectual Property Office of P.R. China in connection with Patent Application No. 200880101500.7, dated Apr. 3, 2013, 2 pages.
Aaker et al., "Warmth in Advertising: Measurement, Impact, and Sequence Effects," Journal of Consumer Research, vol. 12, No. 4, pp. 365-381, (Mar. 1986), 18 pages.
Allen et al., "A Method for Removing Imaging Artifact from Continuous EEG Recorded during Functional MRI," Neuroimage, vol. 12, 230-239, (Aug. 2000), 12 pages.
Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.
Ambler et al., "Ads on the Brain: A Neuro-Imaging Comparison of Cognitive and Affective Advertising Stimuli," London Business School, Centre for Marketing Working Paper, No. 00-902, (Mar. 2000), 23 pages.
Bagozzi et al., "The Role of Emotions in Marketing," Journal of the Academy of Marketing Science, vol. 27, No. 2, pp. 184-206, Academy of Marketing Science (1999), 23 pages.
Barcelo, et al., "Prefrontal modulation of visual processing in humans," Nature Neuroscience, vol. 3, No. 4, Nature America, http//neurosci.nature.com, (Apr. 2000), 5 pages.
Barreto et al., "Physiologic Instrumentation for Real-time Monitoring of Affective State of Computer Users," WSEAS International Conference on Instrumentation, Measurement, Control, Circuits and Systems (IMCCAS), (2004), 6 pages.
Belch et al., "Psychophysiological and cognitive Responses to Sex in Advertising," Advances in Consumer Research, vol. 9, pp. 424-427, (1982), 6 pages.
Bimler et al., "Categorical perception of facial expressions of emotion: Evidence from multidimensional scaling," Cognition and Emotion, vol. 15(5), pp. 633-658 (Sep. 2001), 26 pages.
Blakeslee, "If You Have a 'Buy Button' in Your Brain, What Pushes It?" The New York Times, www.nytimes.com, (Oct. 19, 2004), 3 pages.
Braeutigam, "Neuroeconomics—From neural systems to economic behavior," Brain Research Bulletin, vol. 67, pp. 355-360, Elsevier, (2005), 6 pages.
Buschman, et al., "Top-Down versus Bottom-Up Control of Attention in the Prefrontal and posterior Parietal Cortices," Science, vol. 315, www.sciencemag.org/cgi/content/full/315/5820/1860, American Association for the Advancement of Science, (2007), 4 pages.
Buschman, et al., "Serial, Covert Shifts of Attention during Visual Search Are Reflected by the Frontal Eye Fields and Correlated with Population Oscillations," Neuron, vol. 63, pp. 386-396, Elsevier, (Aug. 13, 2009), 11 pages.
Canolty, et al., "High Gamma Power Is Phase-Locked to Theta Oscillations in Human Neocortex," Science, vol. 313, www.sciencemag.org, (Sep. 15, 2006), 3 pages.

(56) References Cited

OTHER PUBLICATIONS

Cheng, et al. "Gender Differences in the Mu Rhythm of the Human Mirror-Neuron System," PLos One, vol. 3, Issue 5, www.plosone.org, (May 2008), 7 pages.
Clemons, "Resonance Marketing in the Age of the Truly Informed Consumer: Creating Profits through Differentiation and Delight," Wharton Information Strategy & Economics Blog 2, available at http://opim.wharton.upenn.edu/.about.clemons/blogs/resonanceblog.pdf, (Mar. 28, 2007), 8 pages.
Clifford, "Billboards That Look Back," The New York Times, NYTimes.com, available at http://www.nytimes.com/2008/05/31/business/media/31billboard.html, (May 31, 2008), 4 pages.
Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.
Davidson, et al., "The functional neuroanatomy of emotion and affective style," Trends in Cognitive Sciences, vol. 3, No. 1, (Jan. 1999), 11 pages.
De Gelder et al., "Categorical Perception of Facial Expressions: Categories and their Internal Structure," Cognition and Emotion, vol. 11(1), pp. 1-23 (1997), 23 pages.
D'Esposito, "From cognitive to neural models of working memory," Phil. Trans. R. Soc. B, doi: 10.1098/rstb.2007.2086, (Mar. 30, 2007), 12 pages.
Desmet, "Measuring Emotions: Development and Application of an Instrument to Measure Emotional Responses to Products," to be published in Funology: From Usability to Enjoyment, pp. 1-13, Kluwer Academic Publishers, (Blythe et al., eds., 2004), 13 pages.
Dien, et al., "Application of Repeated Measures ANOVA to High-Density ERP Datasets: A Review and Tutorial," in Event-Related Potentials: A Methods Handbook pp. 57-82, (Todd C. Handy, ed., 2005), 14 pages.
Edgar, et al., "Digital Filters in ERP Research," in Event-Related Potentials: A Methods Handbook pp. 85-113, (Todd C. Handy, ed., 2005), 15 pages.
EEG Protocols, "Protocols for EEG Recording," retrieved from the Internet on Aug. 23, 2011, http://www.q-metrx.com/EEGrecordingProtocols.pdf, (Nov. 13, 2007), 3 pages.
Engel et al., "Dynamic Predictions: Oscillations and Synchrony in Top-down Processing," Nature Reviews: Neuroscience, vol. 2, pp. 704-716, Macmillian Magazines Ltd., (Oct. 2001), 13 pages.
Filler, "MR Neurography and Diffusion Tensor Imaging: Origins, History & Clinical Impact of the first 50,000 Cases With an Assessment of Efficacy and Utility in a Prospective 5,000 Patent Study Group," Institute for Nerve Medicine, (Nov. 7, 2008), 56 pages.
Fogelson, et al., "Prefrontal cortex is critical for contextual processing: evidence from brain lesions," Brain: A Journal of Neurology, vol. 132, pp. 3002-3010, doi:10.1093/brain/awp230, (Aug. 27, 2009), 9 pages.
Friedman, et al., "Event-Related Potential (ERP) Studies of Memory Encoding and Retrieval: A Selective Review," Microscopy Research and Technique 51:6-22, Wiley-Liss, Inc. (2000), 23 pages.
Fries, "A mechanism for cognitive dynamics. neuronal communication through neuronal coherence," Trends in Cognitive Sciences, vol. 9, No. 10, pp. 474-480, Elsevier B.V. www.sciencedirect.com, (Oct. 2005), 7 pages.
Gaillard, "Problems and Paradigms in ERP Research," Biological Psychology, Elsevier Science Publisher B.V. (1988), 10 pages.
Gargiulo et al., "A Mobile EEG System With Dry Electrodes," (Nov. 2008), 4 pages.
Gazzaley et al., "Top-down Enhancement and Suppression of Magnitude and Speed of Neural Activity," Journal of Cognitive Neuroscience, vol. 17, No. 3, pp. 507-517, Massachusetts Institute of Technology, (2005), 11 pages.
Griss et al., "Characterization of micromachined spiked biopotential electrodes", Biomedical Engineering, IEEE Transactions (Jun. 2002), 8 pages.
Haq, "This Is Your Brain on Advertising," BusinessWeek, Market Research, (Oct. 8, 2007), 4 pages.
Hartikainen et al., Manuscript Draft of "Emotionally arousing stimuli compete with attention to left hemispace," NeuroReport, (Sep. 8, 2007), 26 pages.
Hazlett, et al., "Emotional Response to Television Commercials: Facial EMG vs. Self-Report," Journal of Advertising Research, (Apr. 1999), 17 pages.
Herrmann, et al., "Mechamsms of human attention: event-related potentials and oscillations," Neuroscience and Biobehavioral Reviews, pp. 465-476, Elsevier Science Ltd., www.elsvevier.com/locate/neubiorev, (2001), 12 pages.
Hopf, et al., "Neural Sources of Focused Attention in Visual Search," Cerebral Cortex, 10:1233-1241, Oxford University Press, (Dec. 2000), 9 pages.
Jung et al., "Analysis and Visualization of Single-Trial Event-Related Potentials," Human Brain Mapping vol. 14, 166-185 (2001), 20 pages.
Kay et al., "Identifying natural images from human brain activity," Nature, vol. 452, pp. 352-356, Nature Publishing Group, (Mar. 20, 2008), 5 pages.
Keren, et al., "Saccadic spike potentials in gamma-band EEG: Characterization, detection and suppression,". NeuroImage, http://dx.doi:10.1016/j.neuroimage.2009.10.057, (Oct. 2009), 16 pages.
Kishiyama, et al., "Novelty Enhancements in Memory Are Dependent on Lateral Prefrontal Cortex," The Journal of Neuroscience, pp. 8114-8118, Society for Neuroscience (Jun. 24, 2009), 5 pages.
Kishiyama, et al., "Socioeconomic Disparities Affect Prefrontal Function in Children," Journal of Cognitive Neuroscience pp. 1106-1115, Massachusetts Institute of Technology, (2008), 10 pages.
Klimesch, "EEG alpha and theta oscillations reflect cognitive and memory performance a review and analysis," Brain Research Reviews, vol. 29, 169-195, (1999), 27 pages.
Knight, "Contribution of human hippocampal region to novelty detection," Nature, vol. 383, www.nature.com, (Sep. 19, 1996), 4 pages.
Knight, "Consciousness Unchained: Ethical Issues and the Vegetative and minimally Conscious State," The American Journal of Bioethics, 8:9, 1-2, http://dx.doi.org/10.1080/15265160802414524, (Sep. 1, 2008), 3 pages.
Knight, et al., "Prefrontal cortex regulates inhibition and excitation in distributed neural networks," Acta Psychologica vol. 101, pp. 159-178, Elsevier (1999), 20 pages.
Knight, "Decreased Response to Novel Stimuli after Prefrontal Lesions in Man," Electroencephalography and Clinical Neurophysiology, vol. 59, pp. 9-20, Elsevier Scientific Publishers Ireland, Ltd., (1984), 12 pages.
Krakow et al., "Methodology: EEG-correlated fMRI," Functional Imaging in the Epilepsies, (Lippincott Williams & Wilkins, 2000), 17 pages.
Krugman, "Brain Wave Measures of Media Involvement," Journal of Advertising Research vol. 11, 3-9 (Feb. 1971), 7 pages.
Lachaux et al., "Measuring Phase Synchrony in Brain Signals," Human Brain Mapping 8 (1999), 194-208, 15 pages.
Lee et al., "What is 'neuromarketing'? A discussion and agenda for future research," International Journal of Psychophysiology, vol. 63, pp. 199-204, Elsevier (2006), 6 pages.
Lekakos, "Personalized Advertising Services Through Hybrid Recommendation Methods: The Case of Digital Interactive Television," Department of Informatics, Cyprus University, (2004), 11 pages.
Lewis et al., "Market Researchers make Increasing use of Brain Imaging," ACNR, vol. 5, No. 3, pp. 36-37, (Jul./Aug. 2005), 2 pages.
Luck, et al., "The speed of visual attention in schizophrenia: Electrophysiological and behavioral evidence," Schizophrenia Research, pp. 174-195, Elsevier B.V. www.sciencedirect.com, (2006), 22 pages.
Lui et al., "Marketing Strategies in Virtual Worlds," The Data Base for Advances in Information Systems, vol. 38, No. 4, pp. 77-80, (Nov. 2007), 4 pages.
Makeig, et al., "Mining event-related brain dynamics," Trends in Cognitive Sciences, vol. 8, No. 5, (May 2004), www.sciencedirect.com, 7 pages.

(56) References Cited

OTHER PUBLICATIONS

Makeig, et al., "Dynamic Brain Sources of Visual Evoked Responses," Science, vol. 295, www.sciencemag.org, (Jan. 25, 2002), 5 pages.
The Mathworks, Inc., "MATLAB Data Analysis: Version 7," p. 4-19 (2005), 3 pages.
Merriam-Webster Online Dictionary definition for "tangible," available at http://www.merriam-webster.com/dictionary/tangible, 1 page.
Merriam Webster Online Dictionary, Definition of Virtual Reality, available at http://www.merriam-webster.com/dictionary/virtual%20reality, 2 pages.
Miltner, et al., "Coherence of gamma-band EEG activity as a basis for associative learning," Nature, vol. 397, www.nature.com, (Feb. 4, 1999), 3 pages.
Mosby's Dictionary of Medicine, Nursing, & Health Professions, 2009, Mosby, Inc., Definition of Alpha Wave, 1 page.
Mosby's Dictionary of Medicine, Nursing, & Health Professions, 2009, Mosby, Inc., Definition of Beta Wave, 1 page.
Neurofocus—Neuroscientific Analysis for Audience Engagement, accessed on Jan. 8, 2010, at http://web.archive.org/web/20080621114525/www.neurofocus.com /BrandImage.htm, (2008), 2 pages.
Newell et al., "Categorical perception of familiar objects," Cognition, vol. 85, Issue 2, pp. 113-143 (Sep. 2002), 31 pages.
Nielsen, "Neuroinformatics in Functional Neuroimaging," Informatics and Mathematical Modeling, Technical University of Denmark, (Aug. 30, 2002), 241 pages.
Oberman et al., "EEG evidence for mirror neuron activity during the observation of human and robot actions: Toward an analysis of the human qualities of interactive robots," Neurocomputing 70 (2007) 2194-2203, 10 pages.
Osborne, "Embedded Watermarking for image Verification in Telemedicine," Thesis submitted for the degree of Doctor of Philosophy, Electrical and Electronic Engineering, University of Adelaide (2005), 219 pages.
Padgett et al., "Categorical Perception in Facial Emotion Classification," In Proceedings of the 18th Annual Conference of the Cognitive Science Society, pp. 249-253 (1996), 5 pages.
Page et al., "Cognitive Neuroscience, Marketing and Research," Congress 2006—Foresight—The Predictive Power of Research Conference Papers, ESOMAR Publications, (Sep. 17, 2006), 25 pages.
Paller, et al., "Validating neural correlates of familiarity," Trends in Cognitive Sciences, vol. 11, No. 6, www.sciencedirect.com, (May 2, 2007), 8 pages.
Palva et al., "Phase Synchrony Among Neuronal Oscillations in the Human Cortex," Journal of Neuroscience 25 (2005), 3962-3972, 11 pages.
Picton, et al., "Guidelines for using human event-related potentials to study cognition: Recording standards and publication criteria," Psychophysiology, pp. 127-152, Society for Psychophysiological Research, (2000), 26 pages.
Rizzolatti et al., "The Mirror-Neuron System," Annu. Rev. Neurosci., vol. 27, pp. 169-192, (Mar. 5, 2004), 30 pages.
Ruchkin et al., "Modality-specific processing streams in verbal working memory: evidence from spatio-temporal patterns of brain activity," Cognitive Brain Research, vol. 6, pp. 95-113, Elsevier, (1997), 19 pages.
Rugg, et al., "Event-related potentials and recognition memory," Trends in Cognitive Sciences, vol. 11, No. 6, www.sciencedirect.com, (May 3, 2007), 7 pages.
Rugg, et al., "The ERP and cognitive psychology: conceptual issues," (Sep. 1996), 7 pages.
"User monitoring," Sapien Systems, available at http://web.archive.org/web/20030818043339/http:/www.sapiensystems.com/eye-tracking.html, (Aug. 18, 2003), 1 page.
Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.
Spencer, "Averaging, Detection, and Classification of Single-Trial ERPs," in Event-Related Potentials: A Methods Handbook, pp. 209-227, (Todd C. Handy, ed., 2005), 10 pages.
Arousal in Sport, in Encyclopedia of Applied Psychology, vol. 1, p. 159, retrieved from Google Books, (Spielberger, ed., Elsevier Academic Press, 2004), 1 page.
Srinivasan, "High-Resolution EEG: Theory and Practice," in Event-Related Potentials: A Methods Handbook, pp. 167-188, (Todd C. Handy, ed., 2005), 12 pages.
Sullivan et al., "A brain-machine interface using dry-contact, low-noise EEG sensors," In Proceedings of the 2008 IEEE International Symposium on Circuits and Systems, (May 18, 2008), 4 pages.
Sutherland, "Neuromarketing: What's it all about?" Retrieved from Max Sutherland's Weblog on Aug. 23, 2011, http://www.sutherlandsurvey.com/Column_pages/Neuromarketing_whats_it_all_-about.htm, (Mar. 2007), 5 pages.
Swick, et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.
Taheri, et al., "A dry electrode for EEG recording," Electroencephalography and clinical Neurophysiology, pp. 376-383, Elsevier Science Ireland Ltd. (1994), 8 pages.
Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.
Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.
"Functional magnetic resonance imaging," retrieved online from Wikipedia, the Free Encyclopedia on Aug. 23, 2011, at http://en.wikipedia.org/w/index.php?title=Functional_magnetic_resonance_i-maging&oldid=319601772, (Oct. 13, 2009), 8 pages.
Woldorf, "Distortion of ERP averages due to overlap from temporally adjacent ERPs: Analysis and correction," Psychophysiology, Society for Psychophysiological Research, Cambridge University Press (1993), 22 pages.
Woodman, et al., "Serial Deployment of Attention During Visual Search," Journal of Experimental Psychology: Human Perception and Performance, vol. 29, No. 1, pp. 121-138, American Physiological Association (2003), 18 pages.
Yamaguchi, et al., "Rapid-Prefrontal-Hippocampal Habituation to Novel Events," The Journal of Neuroscience, pp. 5356-5363, Society for Neuroscience, (Apr. 29, 2004), 8 pp.
Yap et al., "TIMER: Tensor Image Morphing for Elastic Registration," NeuroImage, vol. 47, (May 3, 2009), 15 pages.
Yuval-Greenberg, et al., "Transient Induced Gamma-Bands Response in EEG as a Manifestation of Miniature Saccades," Neuron, vol. 58, pp. 429-441, Elsevier Inc. (May 8, 2008), 13 pages.
Ziegenfuss, "Neuromarketing: Advertising Ethical & Medical Technology," The Brownstone Journal, vol. XII, Boston University, pp. 69-73, (May 2005), 9 pages.
Zyga, "A Baseball Cap That Can Read Your Mind," PhysOrg.com, located at www.physorg.com/news130152277.html, (May 16, 2008), 11 pages.
Non-Final Office Action, issued by the United States Patent and Trademark Office in connection with U.S. Appl. No. 12/546,586, dated Apr. 25, 2013, 34 pages.
Non-Final Office Action, issued by the United States Patent and Trademark Office in connection with U.S. Appl. No. 13/444,149, dated May 2, 2013, 27 pages.
Notice of Allowance, issued by the United States Patent and Trademark Office in connection with U.S. Appl. No. 12/056,190, dated May 8, 2013, 4 pages.
Notice of Allowance, issued by the United States Patent and Trademark Office in connection with U.S. Appl. No. 12/056,211, dated May 8, 2013, 5 pages.
Notice of Allowance, issued by the United States Patent and Trademark Office in connection with U.S. Appl. No. 12/135,074, dated May 8, 2013, 5 pages.

(56) References Cited

OTHER PUBLICATIONS

Notice of Allowance, issued by the United States Patent and Trademark Office in connection with U.S. Appl. No. 12/199,596, dated May 8, 2013, 7 pages.
Notice of Allowance, issued by the United States Patent and Trademark Office in connection with U.S. Appl. No. 13/569,711, dated May 14, 2013, 6 pages.
Notice of Allowance, issued by the United States Patent and Trademark Office in connection with U.S. Appl. No. 12/182,874, dated May 17, 2013, 6 pages.
Final Office Action, issued by the United States Patent and Trademark Office in connection with U.S. Appl. No. 12/778,828, dated May 23, 2013, 25 pages.
Office Communication to Applicant, issued by the United States Patent and Trademark Office in connection with U.S. Appl. No. 12/234,388, dated May 24, 2013, 2 pages.
Non-Final Office Action, issued by the United States Patent and Trademark Office in connection with U.S. Appl. No. 12/884,034, dated May 28, 2013, 12 pages.
Notice of Allowance, issued by the United States Patent and Trademark Office in connection with U.S. Appl. No. 12/135,074, dated May 31, 2013, 5 pages.
Notice of Allowance, issued by the United States Patent and Trademark Office in connection with U.S. Appl. No. 12/056,211, dated Jun. 3, 2013, 5 pages.
Notice of Allowance, issued by the United States Patent and Trademark Office in connection with U.S. Appl. No. 12/199,596, dated Jun. 3, 2013, 5 pages.
Notice of Allowance, issued by the United States Patent and Trademark Office in connection with U.S. Appl. No. 12/199,596, dated Jun. 11, 2013, 7 pages.
Notice of Allowance, issued by the United States Patent and Trademark Office in connection with U.S. Appl. No. 12/545,455, dated Jun. 11, 2013, 9 pages.
Notice of Allowance, issued by the United States Patent and Trademark Office in connection with U.S. Appl. No. 12/056,190, dated Jun. 13, 2013, 5 pages.
Office Communication to Applicant, issued by the United States Patent and Trademark Office in connection with U.S. Appl. No. 12/234,388, dated Jun. 13, 2013, 2 pages.
Notice of Allowance, issued by the United States Patent and Trademark Office in connection with U.S. Appl. No. 12/135,074, dated Jun. 21, 2013, 5 pages.
Non-Final Office Action, issued by the United States Patent and Trademark Office in connection with U.S. Appl. No. 13/105,774, dated Jun. 26, 2013, 10 pages.
English Translation of Office Action, issued by the Israeli Patent Office in connection with Patent Application No. 203176, dated Apr. 23, 2013, 1 page.
English Translation of Notice Prior to Allowance, issued by the Israeli Patent Office in connection with Patent Application No. 203176, dated Jun. 30, 2013, 1 page.
Merriam-Webster Online Dictionary, Definition for "Resonance," available at http://www.merriam-webster.com/dictionary/resonance, 4 pages.
Enghoff, Sigurd, Thesis: "Moving ICA and Time-Frequency Analysis in Event-Related EEG Studies of Selective Attention," Technical University of Denmark, (Dec. 1999), 54 pages.
Zhang, P., "Will You Use Animation on Your Web Pages?" Doing Business on the Internet: Opportunities and Pitfalls, C. Romm and F. Sudweeks (eds.), Spring-Verlag (1999), 17 pages.
Notice of Allowance, issued by the United States Patent and Trademark Office in connection with U.S. Appl. No. 12/182,874, dated Jul. 29, 2013, 6 pages.
Office Action, issued by the United States Patent and Trademark Office in connection with U.S. Appl. No. 12/546,586, dated Sep. 12, 2013, 13 pages.
Notice of Allowance, issued by the United States Patent and Trademark Office in connection with U.S. Appl. No. 12/199,596, dated Sep. 13, 2013, 7 pages.
Office Action, issued by the United States Patent and Trademark Office in connection with U.S. Appl. No. 12/113,870, dated Sep. 17, 2013, 11 pages.
Notice of Allowance, issued by the United States Patent and Trademark Office in connection with U.S. Appl. No. 12/778,828, dated Oct. 8, 2013, 11 pages.
English Translation of Office Action, issued by the Japanese Patent Office in connection with Patent Application No. 2010-523112, dated Jul. 30, 2013, 2 pages.
Decision to Grant Patent, issued by the Japanese Patent Office in connection with Patent Application No. 2010-506646, dated Aug. 6, 2013, 4 pages, (includes English translation).
English Translation of Decision on Rejection, issued by the Chinese Patent Office in connection with Patent Application No. 200880017883.X, dated Aug. 5, 2013, 13 pages.
Final Office Action, issued by the United States Patent and Trademark Office in connection with U.S. Appl. No. 12/884,034, dated Oct. 23, 2013, 17 pages.
Notice of Allowance, issued by the United States Patent and Trademark Office in connection with U.S. Appl. No. 12/199,596, dated Nov. 6, 2013, 7 pages.
Final Office Action, issued by the United States Patent and Trademark Office in connection with U.S. Appl. No. 13/444,149, dated Nov. 19, 2013, 11 pages.
Non-Final Office Action, issued by the United States Patent and Trademark Office in connection with U.S. Appl. No. 12/122,253, dated Dec. 3, 2013, 16 pages.
Notice of Allowance, issued by the United States Patent and Trademark Office in connection with U.S. Appl. No. 12/199,596, dated Dec. 23, 2013, 7 pages.
Final Office Action, issued by the United States Patent and Trademark Office in connection with U.S. Appl. No. 13/105,774, dated Jan. 16, 2014, 11 pages.
English Translation of Office Action, issued by the Japanese Patent Office in connection with Patent Application No. 2010-520159, dated Oct. 1, 2013, 2 pages.
Extended European Search Report, issued by the European Patent Office in connection with European Application No. 08798799.6-1657/2180825, dated Nov. 4, 2013, 9 pages.
Coan et al., "Voluntary Facial Expression and Hemispheric Asymmetry Over the Frontal Cortex," Psycophysiology (Nov. 2001), 912-924, 14 pages.
Duchowski, "A Breadth-First Survey of Eye-tracking Applications," Behavior Research Methods, Instruments, and Computers (Nov. 2002), 455-470, 16 pages.
Heo et al., "Wait! Why is it Not Moving? Attractive and Distractive Ocular Responses to Web Ads," Paper presented to AEJMC, (Aug. 2001) Washington, DC, available at http://www.psu.edu/dept/medialab/researchpage/newabstracts/wait.html, 3 pages.
Rothschild et al., "Predicting Memory for Components of TV Commercials from EEG," Journal of Consumer Research (Mar. 1990), p. 472-478, 8 pages.
Beaver, John D., et al., "Individual Differences in Reward Drive Predict Neural Responses to Images of Food", J. of Neuroscience, (May 10, 2006), 5160-5166, 7 pages.
Tapert, Susan F., et al., "Neural Response to Alcohol Stimuli in Adolescents With Alcohol Use Disorder", Arch Gen Psychiatry (Jul. 2003), 727-735, 9 pages.
Shadlen, Michael N. et al., "A Computational Analysis of the Relationship between Neuronal and Behavioral Responses to Visual Motion", The Journal of Neuroscience, (Feb. 15, 1996) 1486-1510, 25 pages.
Office Action, issued by the United States Patent and Trademark Office in connection with U.S. Appl. No. 13/730,541, dated Jan. 30, 2014, 12 pages.
Office Action, issued by the United States Patent and Trademark Office in connection with U.S. Appl. No. 13/730,550, dated Jan. 31, 2014, 5 pages.
Office Action, issued by the United States Patent and Trademark Office in connection with U.S. Appl. No. 13/965,805, dated Feb. 3, 2014, 15 pages.

(56) References Cited

OTHER PUBLICATIONS

Notice of Allowance, issued by the United States Patent and Trademark Office in connection with U.S. Appl. No. 13/444,149, dated Feb. 3, 2014, 5 pages.
Office Action, issued by the United States Patent and Trademark Office in connection with U.S. Appl. No. 12/113,870, dated Feb. 4, 2014, 12 pages.
Office Action, issued by the United States Patent and Trademark Office in connection with U.S. Appl. No. 12/546,586, dated Feb. 6, 2014, 17 pages.
Office Action, issued by the United States Patent and Trademark Office in connection with U.S. Appl. No. 13/730,564, dated Feb. 10, 2014, 14 pages.
Office Action, issued by the United States Patent and Trademark Office in connection with U.S. Appl. No. 12/884,034, dated Feb. 10, 2014, 18 pages.
Mehta, A. et al., "Reconsidering Recall and Emotion in Advertising", Journal of Advertising Research, (Mar. 2006), 49-56, 9 pages.
Cheung, Kwok-Wai, et al., "Mining Customer Product Ratings for Personalized Marketing," Decision Support Systems 35 (2003) 231-243, 13 pages.
English Translation of Office Action, issued by the Israel Patent Office in connection with Patent Application No. 201187, dated Apr. 2, 2013, 2 pages.
Notice of Allowance, issued by the United States Patent and Trademark Office in connection with U.S. Appl. No. 13/730,550, dated May 27, 2014, 8 pages.
Office Action, issued by the United States Patent and Trademark Office in connection with U.S. Appl. No. 12/608,660, dated Jun. 2, 2014, 13 pages.
Office Action, issued by the United States Patent and Trademark Office in connection with U.S. Appl. No. 12/122,253, dated Jun. 5, 2014, 25 pages.
Final Office Action, issued by the United States Patent and Trademark Office in connection with U.S. Appl. No. 12/113,870, dated Jul. 1, 2014, 16 pages.
Decision to Grant Patent, issued by the Japanese Patent Office in connection with Patent Application No. 2010-523112, dated Apr. 8, 2014, 4 pages. (includes English translation).
Darrow, Chester, "Psychological and psychophysiological significance of the electroencephalogram," Psychological Review (May 1947) 157-168, 12 pages.
Stamm, John, "On the Relationship between Reaction Time to Light and Latency of Blocking the Alpha Rhythm,". Electroencephalography and Clinical Neurophysiology (Feb. 1952), 61-68, 8 pages.
Mizuki, Yashushi, et al., "Periodic Appearance of the Theta Rhythm in the Frontal Midline Area During Performance of a Mental Task,:" Electroencephalography and Clinical Neurophysiology (Aug. 1980), 345-351, 7 pages.
Decision to Grant Patent, issued by the Korean Patent Office in connection with Patent Application No. 10-2009-7022551, dated Aug. 13, 2014, 3 pages. (includes English translation).
Non-Final Office Action, issued by the United States Patent and Trademark Office in connection with U.S. Appl. No. 13/730,541, dated Jul. 23, 2014, 13 pages.
Non-Final Office Action, issued by the United States Patent and Trademark Office in connection with U.S. Appl. No. 13/965,805, dated Aug. 6, 2014, 18 pages.
Non-Final Office Action, issued by the United States Patent and Trademark Office in connection with U.S. Appl. No. 13/730,550, dated Aug. 14, 2014, 4 pages.
Non-Final Office Action, issued by the United States Patent and Trademark Office in connection with U.S. Appl. No. 13/730,564, dated Aug. 15, 2014, 15 pages.
Non-Final Office Action, issued by the United States Patent and Trademark Office in connection with U.S. Appl. No. 12/884,034, dated Aug. 21, 2014, 20 pages.
Non-Final Office Action, issued by the United States Patent and Trademark Office in connection with U.S. Appl. No. 12/608,685, dated Sep. 4, 2014, 16 pages.
Non-Final Office Action, issued by the United States Patent and Trademark Office in connection with U.S. Appl. No. 13/105,774, dated Sep. 18, 2014, 14 pages.
Final Office Action, issued by the United States Patent and Trademark Office in connection with U.S. Appl. No. 12/546,586, dated Sep. 29, 2014, 21 pages.
Ekman, P., Friesen, W., Measuring Facial Movement, Environmental Psychology and Nonverbal Behavior, 1 (1) (Fall 1976), pp. 56-75, 20 pages.
Ekman, P., Friesen, W.V., Facial Action Coding System: A Technique for Measurement of Facial Movement, Consulting Psychologists Press, Palo Alto, Calif. (1978).
Ekman, P., Friesen, W., Unmasking the Face—A Guide to Recognizing Emotions from Facial Clues, Prentice-Hall, Inc., Englewood Cliffs, N.J. (1979).
Ekman, P,. Friesen, W., Ancoli, S., Facial Signs of Emotional Experience, J. Personality & Social Psychology, 39(6) (Dec. 1980), pp. 1125-1134, 10 pages.
Izard, C. E., The Maximally Discriminative Facial Movement Coding System, (Rev. ed.), Instructional Resources Center, University of Delaware, Newark, Del. (1983).
Izard, C., Dougherty, L., Hembree, E., A System for Identifying Affect Expressions by Holistic Judgments (AFFEX), Instructional Resources Center, University of Delaware, Newark, Del. (1983).
Jia, X., Nixon, M.S., Extending the Feature Set for Automatic Face Recognition, International Conference on Image Processing and Its Applications (Apr. 7-9, 1992), 6 pages.
Lisetti, C., Nasoz, F., Using Noninvasive Wearable Computers to Recognize Human Emotions from Physiological Signals, EURASIP J. Applied Signal Processing, (Sep. 11, 2004), pp. 1672-1687, 16 pages.
Non-Final Office Action, issued by the United States Patent and Trademark Office in connection with U.S. Appl. No. 14/177,698, dated Oct. 24, 2014, 13 pages.
Advisory Action, issued by the United States Patent and Trademark Office in connection with U.S. Appl. No. 12/546,586, dated Dec. 22, 2014, 3 pages.
English Translation of Notification of Provisional Rejection, issued by the Korean Patent Office in connection with Patent Application No. 10-2010-7001406, dated Oct. 21, 2014, 1 page.
Non-Final Office Action, issued by the United States Patent and Trademark Office in connection with U.S. Appl. No. 13/730,550, dated Feb. 20, 2015, 12 pages.
Final Office Action, issued by the United States Patent and Trademark Office in connection with U.S. Appl. No. 12/608,660, dated Feb. 20, 2015, 52 pages.
Final Office Action, issued by the United States Patent and Trademark Office in connection with U.S. Appl. No. 13/965,805, dated Mar. 6, 2015, 18 pages.
Non-Final Office Action, issued by the United States Patent and Trademark Office in connection with U.S. Appl. No. 13/708,344, dated Apr. 9, 2015, 12 pages.
Final Office Action, issued by the United States Patent and Trademark Office in connection with U.S. Appl. No. 14/177,698, dated Apr. 24, 2015, 13 pages.
Final Office Action, issued by the United States Patent and Trademark Office in connection with U.S. Appl. No. 12/608,685, dated May 5, 2015, 7 pages.
Final Office Action, issued by the United States Patent and Trademark Office in connection with U.S. Appl. No. 13/105,774, dated May 14, 2015, 15 pages.
Final Office Action, issued by the United States Patent and Trademark Office in connection with U.S. Appl. No. 12/884,034, dated May 14, 2015, 22 pages.
Final Office Action, issued by the United States Patent and Trademark Office in connection with U.S. Appl. No. 13/730,564, dated May 22, 2015, 6 pages.
Final Office Action, issued by the United States Patent and Trademark Office in connection with U.S. Appl. No. 13/249,512, dated Jun. 30, 2015, 36 pages.
Notification of Provisional Rejection, issued by the Korean Patent Office in connection with Patent Application No. 10-2010-7001406, dated Jun. 24, 2015, 9 pages. (includes partial translation).

(56) References Cited

OTHER PUBLICATIONS

McClure, Samuel, et al., "Neural Correlates of Behavioral Preference for Culturally Familiar Drinks," Neuron (Oct. 14, 2004), 379-387, 9 pages.
English Translation of Office Action, issued by the Israel Patent Office in connection with Patent Application No. 201187, dated Jun. 22, 2015, 4 pages.
Examiner's Answer, issued by the United States Patent and Trademark Office in connection with U.S. Appl. No. 12/113,870, dated Jul. 30, 2015, 14 pages.
Examiner's Answer, issued by the United States Patent and Trademark Office in connection with U.S. Appl. No. 12/122,253, dated Aug. 4, 2015, 29 pages.
Non-Final Office Action, issued by the United States Patent and Trademark Office in connection with U.S. Appl. No. 14/177,698, dated Aug. 19, 2015, 12 pages.
Examiner's Answer, issued by the United States Patent and Trademark Office in connection with U.S. Appl. No. 12/546,586, dated Sep. 11, 2015, 7 pages.
Final Office Action, issued by the United States Patent and Trademark Office in connection with U.S. Appl. No. 13/730,550, dated Sep. 2, 2015, 6 pages.
Non-Final Office Action, issued by the United States Patent and Trademark Office in connection with U.S. Appl. No. 12/410,380, dated Sep. 10, 2015, 15 pages.
Advisory Action, issued by the United States Patent and Trademark Office in connection with U.S. Appl. No. 12/884,034, dated Sep. 16, 2015, 3 pages.
Non-Final Office Action, issued by the United States Patent and Trademark Office in connection with U.S. Appl. No. 13/705,525, dated Sep. 30, 2015, 12 pages.
Non-Final Office Action, issued by the United States Patent and Trademark Office in connection with U.S. Appl. No. 13/965,805, dated Sep. 30, 2015, 6 pages.
Final Office Action, issued by the United States Patent and Trademark Office in connection with U.S. Appl. No. 13/708,344, dated Nov. 20, 2015, 28 pages.
Translation of Reexamination Decision, issued by the Chinese Patent Office in connection with Patent Application No. 200880017883.X, dated Nov. 13, 2015, 1 page.
Non-Final Office Action, issued by the United States Patent and Trademark Office in connection with U.S. Appl. No. 12/608,685, dated Dec. 17, 2015, 14 pages.
Examiner's Answer, issued by the United States Patent and Trademark Office in connection with U.S. Appl. No. 13/730,541, dated Dec. 18, 2015, 7 pages.
Notice of Allowance, issued by the United States Patent and Trademark Office in connection with U.S. Appl. No. 14/177,698, dated Jan. 14, 2016, 36 pages.
Non-Final Office Action, issued by the United States Patent and Trademark Office in connection with U.S. Appl. No. 12/608,660, dated Jan. 22, 2016, 38 pages.
Final Office Action, issued by the United States Patent and Trademark Office in connection with U.S. Appl. No. 13/708,525, dated Feb. 3, 2016, 22 pages.
Non-Final Office Action, issued by the United States Patent and Trademark Office in connection with U.S. Appl. No. 12/410,372, dated Feb. 23, 2016, 24 pages.
English Translation of Notification of Provisional Rejection, issued by the Korean Patent Office in connection with Patent Application No. 10-2010-7001406, dated Jan. 26, 2016, 1 page.
English Translation of Notification to Grant Patent Right for Invention, issued by the State Intellectual Property Office of P.R. China in connection with Patent Application No. 200880017883.X, dated Feb. 3, 2016, 2 pages.
Final Office Action, issued by the United States Patent and Trademark Office in connection with U.S. Appl. No. 12/410,380, dated Mar. 22, 2016, 27 pages.
Final Office Action, issued by the United States Patent and Trademark Office in connection with U.S. Appl. No. 12/608,685, dated Mar. 30, 2016, 23 pages.
Advisory Action, issued by the United States Patent and Trademark Office in connection with U.S. Appl. No. 13/708,525, dated Apr. 6, 2016, 3 pages.
Examiner's Answer, issued by the United States Patent and Trademark Office in connection with U.S. Appl. No. 13/730,564, dated Apr. 8, 2016, 7 pages.
Final Office Action, issued by the United States Patent and Trademark Office in connection with U.S. Appl. No. 13/965,805, dated Apr. 21, 2016, 33 pages.
Final Office Action, issued by the United States Patent and Trademark Office in connection with U.S. Appl. No. 12/234,372, dated May 12, 2016, 61 pages.
Non-Final Office Action, issued by the United States Patent and Trademark Office in connection with U.S. Appl. No. 12/884,034, dated May 20, 2016, 69 pages.
Non-Final Office Action, issued by the United States Patent and Trademark Office in connection with U.S. Appl. No. 13/945,357, dated May 20, 2016, 22 pages.
M. Corbetta et al., "Control of Goal-Directed and Stimulus-Driven Attention in the Brain," Nature Reviews Neuroscience, vol. 3, pp. 201-215 (Mar. 2002), 15 pages.
Becker, "A Study of Web Usability for Older Adults Seeking Online Health Resources," ACM Transactions on Computer-Human Interaction, vol. 11, No. 4, pp. 387-406 (Dec. 2004), 20 pages.
Non-Final Office Action, issued by the United States Patent and Trademark Office in connection with U.S. Appl. No. 12/410,380, dated Jun. 17, 2016, 20 pages.
Notice of Allowance, issued by the United States Patent and Trademark Office in connection with U.S. Appl. No. 12/608,660, dated Jul. 29, 2016, 67 pages.
Examiner's Answer, issued by the United States Patent and Trademark Office in connection with U.S. Appl. No. 13/730,550, dated Jul. 27, 2016, 20 pages.
Advisory Action, issued by the United States Patent and Trademark Office in connection with U.S. Appl. No. 12/234,372, dated Aug. 8, 2016, 3 pages.
Non-Final Office Action, issued by the United States Patent and Trademark Office in connection with U.S. Appl. No. 12/413,297, dated Aug. 16, 2016, 5 pages.
Final Office Action, issued by the United States Patent and Trademark Office in connection with U.S. Appl. No. 12/410,372, dated Aug. 25, 2016, 61 pages.
Notification of Provisional Rejection, issued by the Korean Patent Office in connection with Patent Application No. 10-2010-7001406, dated Jul. 27, 2016, 4 pages. (includes partial translation).
Final Office Action, issued by the United States Patent and Trademark Office in connection with U.S. Appl. No. 13/945,357, dated Nov. 1, 2016, 22 pages.
Advisory Action, issued by the United States Patent and Trademark Office in connection with U.S. Appl. No. 12/410,372, dated Nov. 7, 2016, 3 pages.
Examiner's Answer, issued by the United States Patent and Trademark Office in connection with U.S. Appl. No. 12/234,372, dated Nov. 14, 2016, 18 pages.
Examiner's Answer, issued by the United States Patent and Trademark Office in connection with U.S. Appl. No. 12/608,685, dated Nov. 14, 2016, 10 pages.
Final Office Action, issued by the United States Patent and Trademark Office in connection with U.S. Appl. No. 12/884,034, dated Nov. 29, 2016, 27 pages.
European Patent Office, "Communication Pursuant to Article 94(3) EPC," in connection with European Application No. 08796890.5, dated Sep. 29, 2016, 4 pages.
Final Office Action, issued by the United States Patent and Trademark Office in connection with U.S. Appl. No. 12/410,380, dated Dec. 15, 2016, 31 pages.
Non-Final Office Action, issued by the United States Patent and Trademark Office in connection with U.S. Appl. No. 13/708,344, dated Jan. 26, 2017, 52 pages.

(56) References Cited

OTHER PUBLICATIONS

Examiner's Answer, issued by the United States Patent and Trademark Office in connection with U.S. Appl. No. 13/965,805, dated Jan. 31, 2017, 25 pages.
Final Office Action, issued by the United States Patent and Trademark Office in connection with U.S. Appl. No. 12/413,297, dated Feb. 9, 2017, 7 pages.
Advisory Action, issued by the United States Patent and Trademark Office in connection with U.S. Appl. No. 12/884,034, dated Mar. 2, 2017, 14 pages.
English Translation of Notice Prior to Allowance, issued by the Israeli Patent Office in connection with Patent Application No. 201187, dated Feb. 14, 2017, 1 page.
Decision on Appeal, issued by the United States Patent and Trademark Office in connection with U.S. Appl. No. 12/122,253, dated Mar. 31, 2017, 37 pages.
Non-Final Office Action, issued by the United States Patent and Trademark Office in connection with U.S. Appl. No. 13/708,525, dated Apr. 27, 2017, 45 pages.
Examiner's Answer, issued by the United States Patent and Trademark Office in connection with U.S. Appl. No. 12/410,372, dated May 25, 2017, 9 pages.
Decision on Appeal, issued by the United States Patent and Trademark Office in connection with U.S. Appl. No. 12/546,586, dated Jun. 5, 2017, 39 pages.
European Patent Office, "Communication Pursuant to Article 94(3) EPC," issued in connection with European Patent Application No. 08 744 383.4, dated Apr. 19, 2017, 6 pages.
Final Office Action, issued by the United States Patent and Trademark Office in connection with U.S. Appl. No. 13/708,344, dated Jun. 29, 2017, 38 pages.
Non-Final Office Action, issued by the United States Patent and Trademark Office in connection with U.S. Appl. No. 13/945,357, dated Jul. 6, 2017, 17 pages.
Decision on Appeal, issued by the United States Patent and Trademark Office in connection with U.S. Appl. No. 12/113,870, dated Jul. 13, 2017, 12 pages.
Final Office Action, issued by the United States Patent and Trademark Office in connection with U.S. Appl. No. 13/708,525, dated Aug. 14, 2017, 38 pages.
Examiner's Answer, issued by the United States Patent and Trademark Office in connection with U.S. Appl. No. 12/410,380, dated Aug. 18, 2017, 2017, 11 pages.
Non-Final Office Action, issued by the United States Patent and Trademark Office in connection with U.S. Appl. No. 12/546,586, dated Sep. 19, 2017, 43 pages.
Notice of Allowance, issued by the United States Patent and Trademark Office in connection with U.S. Appl. No. 12/113,870, dated Sep. 26, 2017, 51 pages.
Summons to Attend Oral Proceedings Pursuant to Rule 115(1) EPC, issued by the European Patent Office in connection with European Patent Application No. 08796890.5, dated Jul. 3, 2017, 3 pages.
English Translation of First Examination Report, issued by the Indian Patent Office in connection with Indian Patent Application No. 6145/CHENP/2009, dated Aug. 16, 2017, 6 pages.
Advisory Action, issued by the United States Patent and Trademark Office in connection with U.S. Appl. No. 13/708,344, dated Oct. 2, 2017, 5 pages.
Final Office Action, issued by the United States Patent and Trademark Office in connection with U.S. Appl. No. 13/945,357, dated Oct. 20, 2017, 16 pages.
Advisory Action, issued by the United States Patent and Trademark Office in connection with U.S. Appl. No. 13/708,525, dated Oct. 26, 2017, 4 pages.
Examiner's Answer, issued by the United States Patent and Trademark Office in connection with U.S. Appl. No. 12/413,297, dated Oct. 31, 2017, 2017, 68 pages.
Non-Final Office Action, issued by the United States Patent and Trademark Office in connection with U.S. Appl. No. 15/299,752, dated Nov. 3, 2017, 131 pages.
Non-Final Office Action, issued by the United States Patent and Trademark Office in connection with U.S. Appl. No. 12/884,034, dated Nov. 15, 2017, 49 pages.
Decision on Appeal, issued by the United States Patent and Trademark Office in connection with U.S. Appl. No. 13/730,541, dated Dec. 6, 2017, 14 pages.
Non-Final Office Action, issued by the United States Patent and Trademark Office in connection with U.S. Appl. No. 12/546,586, dated Dec. 28, 2017, 23 pages.
Decision on Appeal, issued by the United States Patent and Trademark Office in connection with U.S. Appl. No. 12/608,685, dated Jan. 29, 2018, 11 pages.
Ganel et al., "The Relationship Between fMRI Adapation and Repetition Priming," NeuroImage, Jul. 18, 2006, pp. 1434-1440, 9 pages.
Non-Final Office Action, issued by the United States Patent and Trademark Office in connection with U.S. Appl. No. 13/730,511, dated Jan. 30, 2014, 67 pages.
Non-Final Office Action, issued by the United States Patent and Trademark Office in connection with U.S. Appl. No. 13/730,511, dated Aug. 13, 2014, 8 pages.
Final Office Action, issued by the United States Patent and Trademark Office in connection with U.S. Appl. No. 13/730,511, dated May 6, 2015, 15 pages.
Examiner's Answer, issued by the United States Patent and Trademark Office in connection with U.S. Appl. No. 13/730,511, dated Feb. 18, 2016, 5 pages.
Decision on Appeal, issued by the United States Patent and Trademark Office in connection with U.S. Appl. No. 13/730,511, dated Mar. 1, 2018, 14 pages.
Notice of Allowance, issued by the United States Patent and Trademark Office in connection with U.S. Appl. No. 13/730,511, dated May 29, 2014, 8 pages.
Final Office Action, issued by the United States Patent and Trademark Office in connection with U.S. Appl. No. 13/730,541, dated Feb. 12, 2015, 6 pages.
Decision on Appeal, issued by the United States Patent and Trademark Office in connection with U.S. Appl. No. 12/410,380, dated Mar. 30, 2015, 6 pages.
Decision on Appeal, issued by the United States Patent and Trademark Office in connection with U.S. Appl. No. 12/234,372, dated Jun. 15, 2015, 5 pages.
Non-Final Office Action, issued by the United States Patent and Trademark Office in connection with U.S. Appl. No. 12/234,372, dated Sep. 23, 2015, 16 pages.
Decision on Appeal, issued by the United States Patent and Trademark Office in connection with U.S. Appl. No. 12/410,372, dated Sep. 22, 2015, 6 pages.
Decision on Appeal, issued by the United States Patent and Trademark Office in connection with U.S. Appl. No. 12/413,297 , dated Nov. 27, 2015, 5 pages.
Decision on Appeal, issued by the United States Patent and Trademark Office in connection with U.S. Appl. No. 13/730,564, dated Feb. 2, 2018, 10 pages.
Decision on Appeal, issued by the United States Patent and Trademark Office in connection with U.S. Appl. No. 13/730,550, dated Mar. 27, 2018, 13 pages.
Notice of Allowance, issued by the United States Patent and Trademark Office in connection with U.S. Appl. No. 15/299,752, dated Apr. 17, 2017, 21 pages.
Non-Final Office Action, issued by the United States Patent and Trademark Office in connection with U.S. Appl. No. 12/884,034, dated May 3, 2018, 46 pages.
Non-Final Office Action, issued by the United States Patent and Trademark Office in connection with U.S. Appl. No. 13/708,525, dated May 18, 2018, 31 pages.
Notice of Allowance, issued by the United States Patent and Trademark Office in connection with U.S. Appl. No. 13/730,541, dated Jun. 27, 2018, 62 pages.
Notice of Allowance, issued by the United States Patent and Trademark Office in connection with U.S. Appl. No. 13/730,564, dated Jun. 27, 2018, 69 pages.

(56) References Cited

OTHER PUBLICATIONS

Final Office Action, issued by the United States Patent and Trademark Office in connection with U.S. Appl. No. 12/546,586, dated Jun. 28, 2018, 22 pages.
Decision on Request for Rehearing, issued by the United States Patent and Trademark Office in connection with U.S. Appl. No. 12/608,685, dated Aug. 10, 2018, 8 pages.
Extended European Search Report, issued by the European Patent Office in connection with European Application No. 08747389.8-1952, dated Sep. 25, 2015, 6 pages.
English Translation of First Examination Report, issued by the Indian Patent Office in connection with Indian Patent Application No. 4438/KOLNP/2009, dated Sep. 25, 2017, 7 pages.
Communication Under Rule 71(3) EPC, issued by the European Patent Office in connection with European Application No. 08796890.5, dated Mar. 16, 2018, 43 pages.
English Translation of First Examination Report, issued by the Indian Patent Office in connection with Indian Patent Application No. 4441/KOLNP/2009, dated May 21, 2018, 5 pages.
Knutson et al., "Neural Predictors of Purchases," Neuron vol. 53 (Jan. 4, 2007), pp. 147-156, 10 pages.
Schaefer et al., "Neural Correlates of Culturally Familiar Brands of Car Manufacturers," NeuroImage, vol. 31. (2006), pp. 861-865, 5 pages.
Aharon et al., "Beautiful Faces Have Variable Reward Value: fMRI and Behavioral Evidence," Neuron, vol. 32 (2001), pp. 537-551, 15 pages.
Hall, Bruce F., "A New Model for Measuring Advertising Effectiveness," Journal of Advertising Research, Mar.-Apr. 2002, 10 pages.
Kamba et al., "The Krakatoa Chronicle—An Interactive, Personalized, Newspaper on the Web," available at: http://www.w3.org/Conferences/WWW4/Papers/93/ (last accessed Nov. 2, 2015), 15 pages.
Ehrenberg et al., "Understanding Brand Performance Measures: Using Dirichlet Benchmarks," 2004, Journal of Business Research, vol. 57, pp. 1307-1325, 19 pages.
Leeflang et al., "Building Models for Marketing Decisions," 2000, Springer Science + Business Media, pp. 192-235, 482-521, 86 pages.
Bhattacharya, "Is your brand's loyalty too much, too little, or just right?: Explaining deviations in loyalty from the Dirichlet norm," 1997, International Journal of Research in Marketing, vol. 14, pp. 421-435, 15 pages.
McCraty et al., "Impact of a Workplace Stress Reduction Program on Blood Pressure and Emotional Health in Hypertensive Employees", the Journal of Alternative and Complementary Medicine, vol. 9, No. 3, 2003, pp. 355-369, Mary Ann Liebert, Inc., 15 pages.
Nikolaeva et al., "The Moderating Role of Consumer and Product Characteristics on the Value of Customized On-Line Recommendations," 2006, International Journal of Electronic Commerce, vol. 11, No. 2, pp. 101-123, 24 pages.
Ehrenberg, "New Brands and the Existing Market," 1991, International Journal of Market Research, vol. 33, No. 4, 10 pages.
Foxall, "The Substitutability of Brands," 1999, Managerial and Decision Economics, vol. 20, pp. 241-257, 17 pages.
Pammer et al., "Forecasting the Penetration of a New Product—A Bayesian Approach," 2000, Journal of Business and Economic Statistics, vol. 18, No. 4, pp. 428-435, 8 pages.
Rungie et al., "Calculation of Theoretical Brand Performance Measures from the Parameters of the Dirichlet Model," 2004, Marketing Bulletin, Massey University, 15, Technical Note 2, pp. 1-19, 20 pages.
Uncles et al., "Patterns of Buyer Behavior: Regularities, Models, and Extensions," 1995, Marketing Science, vol. 14, No. 3, pp. G71-G78, 9 pages.
Boltz, "The cognitive processing of film and musical soundtracks," Haverford College, Haverford, Pennsylvania, 2004, 32 (7), 1194-1205, 12 pages.
Christie et al., "Autonomic specificity of discrete emotion and dimensions of affective space: a multivariate approach," International Journal of Psychophysiology, 51 (2004) 143-153, 11 pages.
Coombes et al., "Emotion and movement: Activation of defensive circuitry alters the magnitude of a sustained muscle contraction," University of Florida, USA, Neuroscience Letters 396 (2006) 192-196, 5 pages.
Cryer et al. "Pull the Plug on Stress," Harvard Business Review, Jul. 2003, 8 pages.
Demaree et al., "Predicting facial valence to negative stimuli from resting RSA: Not a function of active emotion regulation," Cognition and Emotion vol. 20, Issue 2, 2006, pp. 161-176, published on Sep. 9, 2010, http://www.tandfonline.com/doi/abs/10.1080/02699930500260427, 6 pages. (Abstract provided.).
Elkman et al., "Autonomic Nervous System Activity Distinguishes among Emotions," Science, New Series, vol. 221, No. 4616. (Sep. 16, 1983), pp. 1208-1210, http://links.jstor.org/sici?sici=0036-8075%28198309l6%293%3A221%3A4616%3C-1208%3AANSADA%3E2.0.CO%3B2-H, 5 pages.
Elton, "Measuring emotion at the symphony," The Boston Globe, Apr. 5, 2006, http://www.psych.mcgill.ca/labs/levitin/media/measuring_emotion_bos- ton.html, 3 pages.
Goldberg, "Getting wired could help predict emotions," The Boston Globe, Jun. 13, 2005, http://www.boston.com/yourlife/health/mental/articles/2005/06/13/getting_-wired_could_help_predict_emotions/?page=full, 4 pages.
Gomez et al., "Respiratory Responses Associated with Affective Processing of Film Stimuli," Biological Psychology, vol. 68, Issue 3, Mar. 2005, pp. 223-235, 2 pages. (Abstract provided.).
Hall, "Is cognitive processing the right dimension," World Advertising Research Center, Jan. 2003, 3 pages.
Hall, "On Measuring the Power of Communications," Journal of Advertising Research, 44, pp. 1-11,. doi:10.1017/S0021849904040139, (2004), 1 page. (Abstract provided.).
Hall, "Research and strategy: a fall from grace," ADMAP, Issue 443, pp. 18-20, 2003, 1 page. (Abstract provided).
Hubert et al., "Autonomic, neuroendocrine, and subjective responses to emotion-inducing film stimuli," Int J Psychophysiology, Aug. 1991, 2 pages. (Abstract provided.).
Levenson et al., "Emotion and Autonomic Nervous System Activity in the Minangkabau of West Sumatra,". Department of Psychology, University of California, Berkeley, Journal of Personality and Social Psychology, 1992, 2 pages. (Abstract provided.).
Marci et al., "The effect of emotional distance on psychophysiologic concordance and perceived empathy between patient and interviewer," Applied Psychophysiology and Biofeedback, Jun. 2006, vol. 31, issue 2, 31:115-129, 8 pages. (Abstract provided.).
McCraty et al., "Analysis of twenty-four hour heart rate variability in patients with panic disorder," Biological Psychology, vol. 56, Issue 2, Jun. 2001, pp. 131-150, 1 page. (Abstract provided.).
McCraty et al., "Electrophysiological Evidence of Intuition: Part 1. The Surprising Role of the Heart," The Journal of Alternative and Complementary Medicine, vol. 10, No. 1, 2004, pp. 133-143, Mary Ann Liebert, Inc., 12 pages.
McCraty et al., "Electrophysiological Evidence of Intuition: Part 2. A System-Wide Process?," The Journal of Alternative and Complementary Medicine, vol. 10, No. 2, 2004, pp. 325-336, Mary Ann Liebert, Inc., 12 pages.
McCraty et al., "The Effects of Different Types of Music on Mood, Tension, and Mental Clarity," Original Research, Alternative Therapies, Jan. 1998, vol. 4., No. 1, pp. 75-84, 10 pages.
McCraty et al., "The Effects of Emotions on Short-Term Power Spectrum Analysis of Heart Rate Variability," American Journal of Cardiology, vol. 76, No. 14, Nov. 15, 1995, pp. 1089-1093, 6 pages.
McCraty et al., "The Impact of a New Emotional Self-Management Program on Stress, Emotions, Heart Rate Variability, DHEA and Cortisol," Integrative Physiological and Behavioral Science, Apr.-Jun. 1998, vol. 33, No. 2, 151-170, 20 pages.
McCraty et al., "The Impact of an Emotional Self-Management Skills Course on Psychosocial Functioning and Autonomic Recovery to Stress in Middle School Children," Integrative Physiological and Behavioral Science, Oct.-Dec. 1999, vol. 34, No. 4, 246-268, 23 pages.

(56) References Cited

OTHER PUBLICATIONS

Melillo, "Inside the Consumer Mind; What Neuroscience Can Tell US About Marketing," Adweek, Public Citizen's Commercial Alert, Jan. 16, 2006, http://www.adweek.com/news/advertising/inside-consumer-mind-83549, 8 pages.
Miller et al., "Influence of Specific Emotional States on Autonomic Reactivity and Pulmonary Function in Asthmatic Children," Journal of the American Academy of Child & Adolescent Psychiatry, vol. 36, Issue 5, May 1997, pp. 669-677, 3 pages. (Abstract provided).
Murphy et al., "The Heart Reinnervates After Transplantation," Official Journal of the Society of Thoracic Surgeons and the Southern Thoracic Surgical Association, Jun. 2000, vol. 69, Issue 6, pp. 1769-1781, 13 pages.
Rosenberg, "Emotional R.O.I.," The Hub, May/Jun. 2006,pp. 24-25, 2 pages.
Tiller et al., "Cardiac Coherence: A New, Noninvasive Measure of Autonomic Nervous System Order," Alternative Therapies, Jan. 1996, vol. 2, No. 1, 14 pages.
Umetani et al. "Twenty-Four Hour Time Domain Heart Rate Variability and Heart Rate: Relations to Age and Gender Over Nine Decades," J Am Coll Cardiol, Mar. 1, 1998, pp. 593-601, 9 pages.
Von Leupoldt et al., "Emotions in a Body Plethysmograph," Journal of Psychophysiology (2004), 18, pp. 170-176, 1 page. (Abstract provided.).
Kallman, "Effect of Blank Time on Picture Recognition," The American Journal of Psychology, vol. 97, No. 3 (Autumn, 1984), pp. 399-406, 4 pages. (Abstract provided.).
Larose, Data Mining Methods and Models, Department of Mathematical Sciences, Central Connecticut State University, www.dbeBooks.com—An Ebook Library, published by John Wiley & Sons, Inc., 2006, 340 pages.
Han et al., Data Mining: Concepts and Techniques, 2.sup.nd Edition, Elsevier, 2006, 772 pages.
Liu et al., Web Data Mining: Exploring Hyperlinks, Contents, and Usage Data, Springer Science & Business Media, 2007, 532 pages.
Berry et al., Data Mining Techniques: for Marketing, Sales, and Customer Support, Wiley Publishing Inc., Jun. 1997, 464 pages.
Horovitz, "Watching Ads Is Real Science Research Companies Monitor Physiological Reactions to Commercials to Determine Their Effectiveness," Los Angeles Times, Sep. 1, 1991, 3 pages.
Sung et al., "Wearable feedback systems for rehabilitation," Journal of NeuroEngineering and Rehabilitation, Jun. 29, 2005, 12 pages.
Jaffe, Casting for Big Ideas, Adweek Magazine Series, Book 8, 2003, 256 page.
Hall, "Advertising as a Factor of Production," ADMAP, 2003, pp. 47-49, 1 page. (Abstract provided.).
Ranii "Adding Science to Gut Check," The News & Observer, D3 (Apr. 6, 2005), 1 page. (Abstract provided.).
Landau et al., "Different Effects of Voluntary and Involuntary Attention on EEG Activity in the Gamma Band," The Journal of Neuroscience, 27(44), Oct. 31, 2007, pp. 11986-11990, 5 pages.
Cohen, "Differentiated product demand analysis with a structured covariance probit: A Bayesian econometric approach," 2009, PhD dissertation, University of Connecticut, pp. 1-184, 197 pages.
Opitz, S. "Neuromarketing: An Introduction" Power Point Presentation (2008), available at http://www.powershow.com/view/94a7b-Yz1mN/Neuromarketing_powerpoint_ppt_p- resentation, (last accessed Oct. 14, 2015), 20 pages.
Jaimes et al., "Multimodal Human-Computer Interaction: A Survey," Computer Vision and Image Understanding, 108 (Oct.-Nov. 2007), pp. 116-134, 19 pages.
English Translation of Office Action, issued by the Israeli Patent Office in connection with Patent Application No. 201187, dated Apr. 23, 2014, 2 pages.
Axis Communications, "Improve your merchandising effectiveness. Get the full picture with. network video," (2008), available at http://www.axis.com/files/user _scenario slap _ret_merchandising_ 31107 en 0803 1o.pdf, 2 pages.
Brown, M., "Should My Advertising Stimulate an Emotional Response?" (2009), available at http://www.wpp.com/ .about./media/sharedwpp/readingroom/marketing/millward brown_emotional_ response.pdf, 6 pages.
Cassanello et al., "Neuronal Responses to Moving Targets in Monkey Frontal Eye Fields," Journal of Neurophysiology, (Sep. 2008), 1544-1556, 16 pages.
Advisory action, issued by the United States Patent and Trademark Office in connection with U.S. Appl. No. 12/608,660, dated Oct. 26, 2012, 3 pages.
Decision on Appeal, issued by the United States Patent and Trademark Office in connection with U.S. Appl. No. 13/965,805, dated Sep. 10, 2018, 11 pages.
Decision on Appeal, issued by the United States Patent and Trademark Office in connection with U.S. Appl. No. 12/234,372, dated Sep. 19, 2018, 8 pages.
Final Office Action, issued by the United States Patent and Trademark Office in connection with U.S. Appl. No. 13/708,525, dated Oct. 5, 2018, 31 pages.
Advisory Action, issued by the United States Patent and Trademark Office in connection with U.S. Appl. No. 12/546,586, dated Oct. 1, 2018, 17 pages.
Non-Final Office Action, issued by the United States Patent and Trademark Office in connection with U.S. Appl. No. 16/037,666, dated Oct. 4, 2018, 37 pages.
Notice of Allowance, issued by the United States Patent and Trademark Office in connection with U.S. Appl. No. 16/037,666, dated Dec. 6, 2018, 96 pages.
Summons to Attend Oral Proceedings Pursuant to Rule 115(1) EPC, issued by the European Patent Office in connection with European Patent Application No. 08744383.4, dated Dec. 11, 2018, 6 pages.
Decision on Appeal, issued by the United States Patent and Trademark Office in connection with U.S. Appl. No. 12/410,372, dated Dec. 28, 2018, 8 pages.
Decision on Request for Rehearing, issued by the United States Patent and Trademark Office in connection with U.S. Appl. No. 12/410,372, dated Mar. 27, 2019, 7 pages.
Decision on Appeal, issued by the United States Patent and Trademark Office in connection with U.S. Appl. No. 12/410,380, dated Jul. 8, 2019, 12 pages.
Decision on Appeal, issued by the United States Patent and Trademark Office in connection with U.S. Appl. No. 12/413,297, dated Sep. 24, 2019, 15 pages.
Non-Final Office Action, issued by the United States Patent and Trademark Office in connection with U.S. Appl. No. 15/967,939, dated Oct. 4, 2019, 5 pages.
Notice of Allowance, issued by the United States Patent and Trademark Office in connection with U.S. Appl. No. 15/989,987, dated Oct. 17, 2019, 8 pages.
Non-Final Office Action, issued by the United States Patent and Trademark Office in connection with U.S. Appl. No. 16/183,131, dated Nov. 18, 2019, 5 pages.
Notice of Allowance, issued by the United States Patent and Trademark Office in connection with U.S. Appl. No. 15/967,939, dated Jan. 29, 2020, 8 pages.
Non-Final Office Action, issued by the United States Patent and Trademark Office in connection with U.S. Appl. No. 12/546,586, dated Jan. 22, 2020, 12 pages.
Intimation of Grant and Recordal of Patent, issued by the Indian Patent Office in connection with Indian Patent Application No. 4438/KOLNP/2009, dated Jul. 3, 2019, 1 page.
Intimation of Grant and Recordal of Patent, issued by the Indian Patent Office in connection with Indian Patent Application No. 4441/KOLNP/2009, dated Sep. 3, 2019, 1 page.
Hearing Notice issued by the Indian Patent Office in connection with Indian Patent Application No. 6145/CHENP/2009, dated Mar. 12, 2020, 2 pages.
Notice of Allowance, issued by the United States Patent and Trademark Office in connection with U.S. Appl. No. 16/183,131, dated Mar. 24, 2020, 8 pages.
Non-Final Office Action, issued by the United States Patent and Trademark Office in connection with U.S. Appl. No. 16/151,044, dated Apr. 2, 2020, 5 pages.

(56) References Cited

OTHER PUBLICATIONS

Non-Final Office Action, issued by the United States Patent and Trademark Office in connection with U.S. Appl. No. 16/151,050, dated Apr. 6, 2020, 13 pages.
Final Office Action, issued by the United States Patent and Trademark Office in connection with U.S. Appl. No. 12/546,586, dated Jul. 24, 2020, 14 pages.
Non-Final Office Action, issued by the United States Patent and Trademark Office in connection with U.S. Appl. No. 16/193,930, dated Jul. 27, 2020, 12 pages.
Non-Final Office Action, issued by the United States Patent and Trademark Office in connection with U.S. Appl. No. 16/421,864, dated Aug. 13, 2020, 24 pages.
Final Office Action, issued by the United States Patent and Trademark Office in connection with U.S. Appl. No. 16/151,050, dated Oct. 7, 2020, 5 pages.
Notice of Allowance, issued by the United States Patent and Trademark Office in connection with U.S. Appl. No. 16/151,044, dated Oct. 9, 2020, 8 pages.
Non-Final Office Action, issued by the United States Patent and Trademark Office in connection with U.S. Appl. No. 16/790,160, dated Oct. 29, 2020, 5 pages.
Notice of Allowance, issued by the United States Patent and Trademark Office in connection with U.S. Appl. No. 16/193,930, dated Nov. 18, 2020, 8 pages.
Kim et al., "Design for an Interactive Television Advertising System," Proceedings for the 39th Hawaii International Conference on System Sciences (2006), 9 pages.
Notice of Allowance, issued by the United States Patent and Trademark Office in connection with U.S. Appl. No. 12/546,586, dated Dec. 9, 2020, 8 pages.
Notice of Allowance, issued by the United States Patent and Trademark Office in connection with U.S. Appl. No. 16/151,050, dated Jan. 22, 2021, 8 pages.
Final Office Action, issued by the United States Patent and Trademark Office in connection with U.S. Appl. No. 16/421,864, dated Jan. 25, 2021, 26 pages.
Notice of Allowance, issued by the United States Patent and Trademark Office in connection with U.S. Appl. No. 16/790,160, dated Feb. 22, 2021, 9 pages.
"One to One Interactive and Innerscope Research Release Preliminary Biomeasures Study Results," PR Newswire, Feb. 28, 2007, 4 pages.
Non-Final Office Action, issued by the United States Patent and Trademark Office in connection with U.S. Appl. No. 16/421,864, dated Apr. 22, 2021, 18 pages.
Non-Final Office Action, issued by the United States Patent and Trademark Office in connection with U.S. Appl. No. 16/692,511, dated Feb. 24, 2021, 12 pages.
Non-Final Office Action, issued by the United States Patent and Trademark Office in connection with U.S. Appl. No. 16/360,282, dated Mar. 18, 2021, 7 pages.
Notice of Allowance, issued by the United States Patent and Trademark Office in connection with U.S. Appl. No. 16/360,282, dated Jun. 24, 2021, 9 pages.

* cited by examiner

| Stimulus Attributes Data Model 201 | | | | | |
|---|---|---|---|---|---|
| Video Game 203 | Rating 205 | Time Span 207 | Audience 209 | Demography 211 | ... |

| Stimulus Purpose Data Model 213 | | | |
|---|---|---|---|
| Intent 215 | Objectives 217 | Candidate Location Information 219 | ... |

| Stimulus Attributes Data Model 221 | | | | |
|---|---|---|---|---|
| Creation Attributes 223 | Ownership Attributes 225 | Broadcast Attributes 227 | Statistical, Demographic, And Survey Based Identifiers 229 | ... |

Figure 2

| Dataset Data Model 301 | | | | | |
|---|---|---|---|---|---|
| Experiment Name 303 | Client Attributes 305 | Subject Pool 307 | Logistics Information 309 | Stimulus Material 311 | ... |

| Subject Attributes Data Model 315 | | | |
|---|---|---|---|
| Subject Name 317 | Demographic Attributes 319 | Contact Information 321 | ... |

| Neuro-Feedback Association Data Model 325 | | | |
|---|---|---|---|
| Experiment Protocols 327 | Modalities included 329 | Experiment Design Parameters 333 | ... |

| Data Collection Data Model 337 | | | | |
|---|---|---|---|---|
| Recording Attributes 339 | Equipment Attributes 341 | Modalities Recorded 343 | Data Storage Attributes 345 | ... |

| Preset Query Data Model 349 | | | | |
|---|---|---|---|---|
| Query Name 351 | Accessed Data Collection 353 | Access Security Attributes 355 | Refresh Attributes 357 | ... |

Figure 3

| Subject Attributes Queries 415 | | | |
|---|---|---|---|
| Location 417 | Demographic Attributes 419 | Session Information 421 | ... |

| Experimental Design Queries 425 | | | | |
|---|---|---|---|---|
| Experiment Protocols 427 | Product Category 429 | Surveys Included 431 | Stimulus Used 433 | ... |

| Response Assessment Queries 437 | | | | |
|---|---|---|---|---|
| Attention Score 439 | Emotion Score 441 | Retention Score 443 | Effectiveness Score 445 | ... |

Figure 4

| Client Assessment Summary Reports 501 | | | |
|---|---|---|---|
| Effectiveness 503 | Component Assessment 505 | Stimulus Location Effectiveness Measures 507 | ... |

| Client Cumulative Reports 511 | | | |
|---|---|---|---|
| Media Grouped 513 | Campaign Grouped 515 | Time/Location Grouped 517 | ... |

| Industry Cumulative And Syndicated Reports 521 | | | | | |
|---|---|---|---|---|---|
| Aggregate Assessment 523 | Top Performers 525 | Bottom Performers 527 | Outliers 529 | Trend 531 | ... |

Figure 5

ANALYSIS OF CONTROLLED AND AUTOMATIC ATTENTION FOR INTRODUCTION OF STIMULUS MATERIAL

RELATED APPLICATIONS

This patent arises from a continuation of U.S. application Ser. No. 16/360,282 (now U.S. Pat. No. 11,170,400), titled "Analysis of Controlled and Automatic Attention for Introduction of Stimulus Material," and filed on Mar. 21, 2019. U.S. application Ser. No. 16/360,282 is a continuation of U.S. application Ser. No. 16/037,666 (now U.S. Pat. No. 10,269,036), titled "Analysis of Controlled and Automatic Attention for Introduction of Stimulus Material," and filed on Jul. 17, 2018. U.S. application Ser. No. 16/037,666 is a continuation of U.S. application Ser. No. 15/299,752 (now U.S. Pat. No. 10,068,248), titled "Analysis of Controlled and Automatic Attention for Introduction of Stimulus Material," and filed on Oct. 21, 2016. U.S. application Ser. No. 15/299,752 is a continuation of U.S. application Ser. No. 12/608,660 (now U.S. Pat. No. 9,560,984), titled "Analysis of Controlled and Automatic Attention for Introduction of Stimulus Material," and filed on Oct. 29, 2009. U.S. application Ser. No. 16/360,282, U.S. application Ser. No. 16/037,666, U.S. application Ser. No. 15/299,752, and U.S. application Ser. No. 12/608,660 are incorporated herein by this reference in their entireties.

This patent is related to U.S. patent application Ser. No. 12/056,190; U.S. patent application Ser. No. 12/056,211; U.S. patent application Ser. No. 12/056,221; U.S. patent application Ser. No. 12/056,225; U.S. patent application Ser. No. 12/113,863; U.S. patent application Ser. No. 12/113,870; U.S. patent application Ser. No. 12/122,240; U.S. patent application Ser. No. 12/122,253; U.S. patent application Ser. No. 12/122,262; U.S. patent application Ser. No. 12/135,066; U.S. patent application Ser. No. 12/135,074; U.S. patent application Ser. No. 12/182,851; U.S. patent application Ser. No. 12/182,874; U.S. patent application Ser. No. 12/199,557; U.S. patent application Ser. No. 12/199,583; U.S. patent application Ser. No. 12/199,596; U.S. patent application Ser. No. 12/200,813; U.S. patent application Ser. No. 12/234,372; U.S. patent application Ser. No. 12/135,069; U.S. patent application Ser. No. 12/234,388; U.S. patent application Ser. No. 12/544,921; U.S. patent application Ser. No. 12/544,958; U.S. patent application Ser. No. 12/546,586; U.S. patent application Ser. No. 12/410,380; U.S. patent application Ser. No. 12/410,372; U.S. patent application Ser. No. 12/413,297; U.S. patent application Ser. No. 12/545,455; U.S. patent application Ser. No. 12/544,934; U.S. patent application Ser. No. 12/608,685; U.S. patent application Ser. No. 13/444,149; U.S. patent application Ser. No. 12/608,696; U.S. patent application Ser. No. 12/731,868; U.S. patent application Ser. No. 13/045,457; U.S. patent application Ser. No. 12/778,810; U.S. patent application Ser. No. 12/778,828; U.S. patent application Ser. No. 13/104,821; U.S. patent application Ser. No. 13/104,840; U.S. patent application Ser. No. 12/846,242; U.S. patent application Ser. No. 12/853,197; U.S. patent application Ser. No. 12/884,034; U.S. patent application Ser. No. 12/868,531; U.S. patent application Ser. No. 12/913,102; U.S. patent application Ser. No. 12/853,213; U.S. patent application Ser. No. 13/105,774; U.S. patent application Ser. No. 13/569,711; U.S. patent application Ser. No. 13/708,525; U.S. patent application Ser. No. 13/708,344; U.S. patent application Ser. No. 13/730,511; U.S. patent application Ser. No. 13/730,550; U.S. patent application Ser. No. 13/730,541; U.S. patent application Ser. No. 13/730,564; U.S. patent application Ser. No. 13/965,805; U.S. patent application Ser. No. 13/945,357; and U.S. patent application Ser. No. 14/177,698.

FIELD OF THE DISCLOSURE

The present disclosure relates to analysis of controlled and automatic attention.

BACKGROUND

Conventional systems for placing stimulus material such as a media clip, product, brand image, message, purchase offer, product offer, etc., are limited. Some placement systems are based on demographic information, statistical data, and survey based response collection. However, conventional systems are subject to semantic, syntactic, metaphorical, cultural, and interpretive errors.

Consequently, it is desirable to provide improved methods and apparatus for introducing stimulus material.

BRIEF DESCRIPTION OF THE DRAWINGS

The disclosure may best be understood by reference to the following description taken in conjunction with the accompanying drawings, which illustrate particular examples.

FIG. 2 illustrates examples of stimulus attributes that can be included in a stimulus attributes repository.

FIG. 3 illustrates examples of data models that can be used with a stimulus and response repository.

FIG. 4 illustrates one example of a query that can be used with a stimulus location selection system.

FIG. 5 illustrates one example of a report generated using the automatic and controlled attention analysis system.

DETAILED DESCRIPTION

Figure 1:
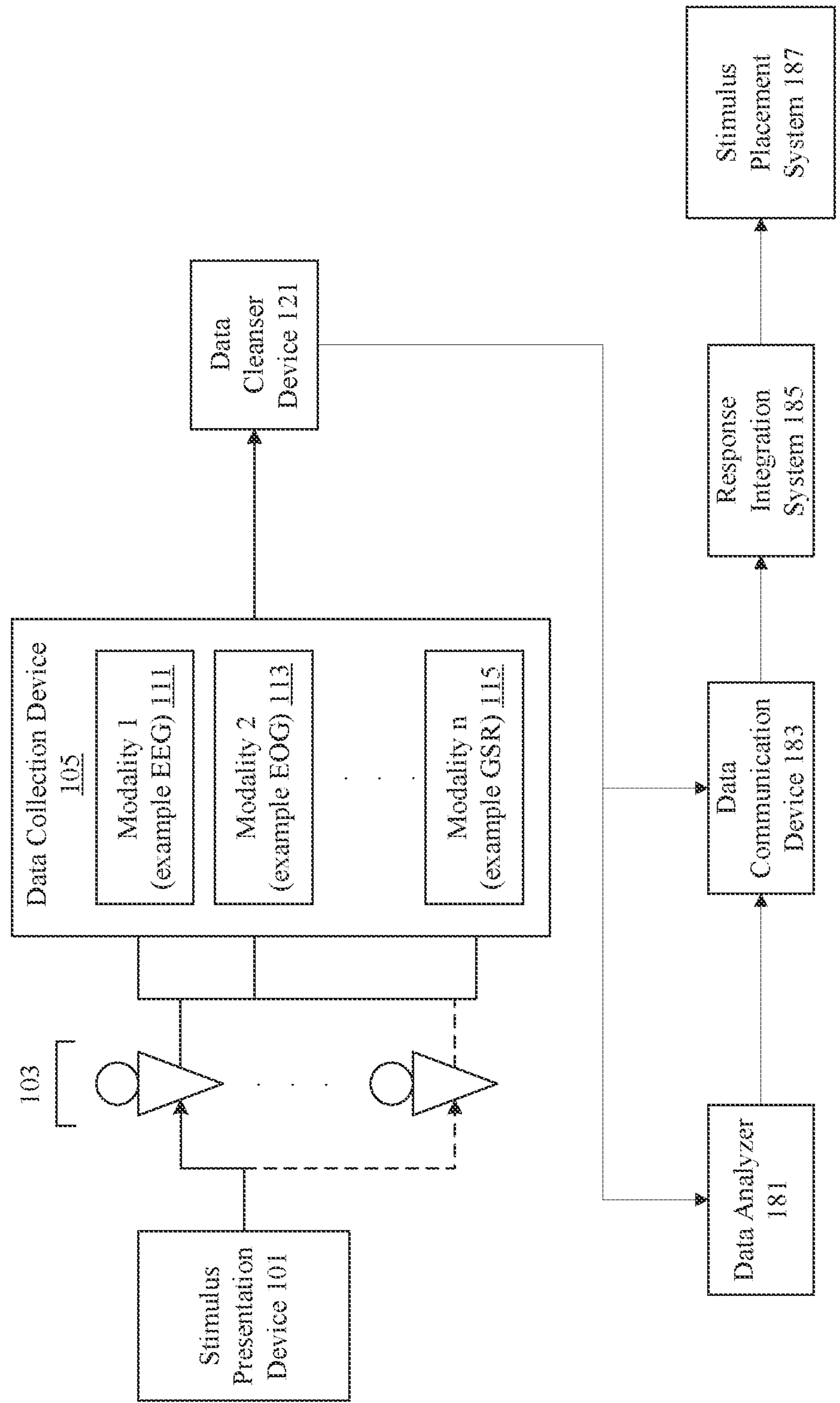
FIG. 1 illustrates one example of a system for neuro-response analysis.

Reference will now be made in detail to some specific examples of the disclosure including the best modes contemplated by the inventors for carrying out the disclosure. Examples are illustrated in the accompanying drawings. While the disclosure is described in conjunction with these specific examples, it will be understood that it is not intended to limit the disclosure to the described examples. On the contrary, it is intended to cover alternatives, modifications, and equivalents as may be included within the spirit and scope of the disclosure as defined by the appended claims.

For example, the techniques and mechanisms of the present disclosure will be described in the context of particular types of data such as central nervous system, autonomic nervous system, and effector data. However, it should be noted that the techniques and mechanisms of the present disclosure apply to a variety of different types of data. It should be noted that various mechanisms and techniques can be applied to any type of stimuli. In the following description, numerous specific details are set forth in order to provide a thorough understanding of the present disclosure. Particular examples may be implemented without some or all of these specific details. In other instances, well known process operations have not been described in detail in order not to unnecessarily obscure the present disclosure.

Various techniques and mechanisms of the present disclosure will sometimes be described in singular form for clarity. However, it should be noted that some examples include multiple iterations of a technique or multiple instantiations of a mechanism unless noted otherwise. For example, a system uses a processor in a variety of contexts. However, it will be appreciated that a system can use multiple processors while remaining within the scope of the present disclosure unless otherwise noted. Furthermore, the techniques and mechanisms of the present disclosure will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

OVERVIEW

A system analyzes neuro-response measurements including regional electroencephalography (EEG) measurements from subjects exposed to stimulus materials to determine locations in stimulus materials eliciting controlled attention and automatic attention. Additional stimulus materials are inserted into locations having salient attention attributes. In some examples, a challenging task is used to direct controlled attention onto a location and additional stimulus material is subtly presented in the location to benefit from automatic attention and salient attention measurements.

EXAMPLES

Conventional placement systems such as product placement systems often rely on demographic information, statistical information, and survey based response collection to determine optimal locations to place stimulus material, such as a new product, a brand image, a video clip, sound files, etc. One problem with conventional stimulus placement systems is that conventional stimulus placement systems do not accurately measure the responses to components of the experience. They are also prone to semantic, syntactic, metaphorical, cultural, and interpretive errors thereby preventing the accurate and repeatable selection of stimulus placement locations.

Conventional systems do not use neuro-response measurements in evaluating spatial and temporal locations for personalized stimulus placement. The techniques and mechanisms of the present disclosure use neuro-response measurements such as central nervous system, autonomic nervous system, and effector measurements to improve stimulus location selection and stimulus personalization in video games. Some examples of central nervous system measurement mechanisms include Functional Magnetic Resonance Imaging (fMRI), Electroencephalography (EEG), and optical imaging. fMRI measures blood oxygenation in the brain that correlates with increased neural activity. However, current implementations of fMRI have poor temporal resolution of few seconds. EEG measures electrical activity associated with post synaptic currents occurring in the milliseconds range. Subcranial EEG can measure electrical activity with the most accuracy, as the bone and dermal layers weaken transmission of a wide range of frequencies. Nonetheless, surface EEG provides a wealth of electrophysiological information if analyzed properly. Even portable EEG with dry electrodes provides a large amount of neuro-response information.

Autonomic nervous system measurement mechanisms include Galvanic Skin Response (GSR), Electrocardiograms (EKG), pupillary dilation, etc. Effector measurement mechanisms include Electrooculography (EOG), eye tracking, facial emotion encoding, reaction time etc.

Many types of stimulus material may be placed into media. In some examples, brand images or messages are introduced into a movie or game. Text advertisements may be placed onto a prop in a video game scene or audio clips may be added to a music file. In some examples, a button to allow a player to purchase an item is provided in a neurologically salient location. Any type of stimulus material may be added to media materials such as movies, programs, texts, offers, games, etc.

However, stimulus material may often go unnoticed or may be ignored all together. Conventional mechanisms for eliciting user attention for stimulus materials in media materials are limited. According to various examples, a controlled and automatic attention analysis system analyzes media materials such as video games and video game scenes to determine candidate locations for introducing stimulus material. Each candidate location may be tagged with characteristics such as high retention placement, high attention location, good priming characteristics, etc. According to various examples, candidate locations are neurologically salient locations. When personalized stimulus is received, one of the candidate locations can be selected for placing the personalized stimulus material. Attention includes controlled attention and automatic attention. Regional EEG, particularly measurements in the frontal cortex, can be used to identify attention. If a search or task is difficult, the frontal cortex becomes involved. Saliency of attention can also be analyzed using EEG and/or other neuro-response mechanisms.

According to various examples, stimulus material is an advertisement or purchase offer tailored to a particular viewer. A controlled and automatic attention analysis mechanism may incorporate relationship assessments using brain regional coherence measures of segments of the stimuli relevant to the entity/relationship, segment effectiveness measures synthesizing the attention, emotional engagement and memory retention estimates based on the neurophysiological measures including time-frequency analysis of EEG measurements, and differential saccade related neural signatures during segments where coupling/relationship patterns are emerging in comparison to segments with non-coupled interactions. In particular examples, specific event related potential (ERP) analyses and/or event related power spectral perturbations (ERPSPs) are evaluated for different regions of the brain both before a subject is exposed to media materials to evaluate controlled and automatic attention and determine locations for introduction of stimulus materials. In particular examples, a task is used to direct a user's controlled attention toward a particular object and stimulus material is introduced at or near the particular object to elicit automatic attention.

Pre-stimulus and post-stimulus differential as well as target and distracter differential measurements of ERP time domain components at multiple regions of the brain are determined (DERP). Event related time-frequency analysis of the differential response to assess the attention, emotion and memory retention (DERPSPs) across multiple frequency bands including but not limited to theta, alpha, beta, gamma and high gamma is performed. In particular examples, single trial and/or averaged DERP and/or DERPSPs can be used to enhance selection of stimulus locations.

FIG. 1 illustrates one example of a system for performing controlled and automatic attention analysis system using neuro-response data. According to various examples, the stimulus location selection and personalization system includes a stimulus presentation device 101. In particular examples, the stimulus presentation device 101 is merely a display, monitor, screen, etc., that displays scenes of a video game to a user. Video games may include action, strategy, puzzle, simulation, role-playing, and other computer games. The stimulus presentation device 101 may also include one or more controllers used to control and interact with aspects of the video game. Controllers may include keyboards, steering wheels, motion controllers, touchpads, joysticks, control pads, etc.

According to various examples, the subjects 103 are connected to data collection devices 105. The data collection devices 105 may include a variety of neuro-response measurement mechanisms including neurological and neuro-physiological measurements systems such as EEG, EOG, GSR, EKG, pupillary dilation, eye tracking, facial emotion encoding, and reaction time devices, etc. According to various examples, neuro-response data includes central nervous system, autonomic nervous system, and effector data. In particular examples, the data collection devices 105 include EEG 111, EOG 113, and GSR 115. In some instances, only a single data collection device is used. Data collection may proceed with or without human supervision.

The data collection device 105 collects neuro-response data from multiple sources. This includes a combination of devices such as central nervous system sources (EEG), autonomic nervous system sources (GSR, EKG, pupillary dilation), and effector sources (EOG, eye tracking, facial emotion encoding, reaction time). In particular examples, data collected is digitally sampled and stored for later analysis. In particular examples, the data collected could be analyzed in real-time. According to particular examples, the digital sampling rates are adaptively chosen based on the neurophysiological and neurological data being measured.

In one particular examples, the stimulus location selection system includes EEG 111 measurements made using scalp level electrodes, EOG 113 measurements made using shielded electrodes to track eye data, GSR 115 measurements performed using a differential measurement system, a facial muscular measurement through shielded electrodes placed at specific locations on the face, and a facial affect graphic and video analyzer adaptively derived for each individual.

In particular examples, the data collection devices are clock synchronized with a stimulus presentation device 101. In particular examples, the data collection devices 105 also include a condition evaluation subsystem that provides auto triggers, alerts and status monitoring and visualization components that continuously monitor the status of the subject, data being collected, and the data collection instruments. The condition evaluation subsystem may also present visual alerts and automatically trigger remedial actions. According to various examples, the data collection devices include mechanisms for not only monitoring subject neuro-response to stimulus materials, but also include mechanisms for identifying and monitoring the stimulus materials. For example, data collection devices 105 may be synchronized with a set-top box to monitor channel changes. In other examples, data collection devices 105 may be directionally synchronized to monitor when a subject is no longer paying attention to stimulus material. In still other examples, the data collection devices 105 may receive and store stimulus material generally being viewed by the subject, whether the stimulus is a program, a commercial, printed material, an experience, or a scene outside a window. The data collected allows analysis of neuro-response information and correlation of the information to actual stimulus material and not mere subject distractions.

According to various examples, the stimulus location selection system also includes a data cleanser device 121. In particular examples, the data cleanser device 121 filters the collected data to remove noise, artifacts, and other irrelevant data using fixed and adaptive filtering, weighted averaging, advanced component extraction (like PCA, ICA), vector and component separation methods, etc. This device cleanses the data by removing both exogenous noise (where the source is outside the physiology of the subject, e.g. a phone ringing while a subject is viewing a video) and endogenous artifacts (where the source could be neurophysiological, e.g. muscle movements, eye blinks, etc.).

The artifact removal subsystem includes mechanisms to selectively isolate and review the response data and identify epochs with time domain and/or frequency domain attributes that correspond to artifacts such as line frequency, eye blinks, and muscle movements. The artifact removal subsystem then cleanses the artifacts by either omitting these epochs, or by replacing these epoch data with an estimate based on the other clean data (for example, an EEG nearest neighbor weighted averaging approach).

According to various examples, the data cleanser device 121 is implemented using hardware, firmware, and/or software. It should be noted that although a data cleanser device 121 is shown located after a data collection device 105 and before data analyzer 181, the data cleanser device 121 like other components may have a location and functionality that varies based on system implementation. For example, some systems may not use any automated data cleanser device whatsoever while in other systems, data cleanser devices may be integrated into individual data collection devices.

According to various examples, an optional stimulus attributes repository 131 provides information on the stimulus material being presented to the multiple subjects. According to various examples, stimulus attributes include properties of the stimulus materials as well as purposes, presentation attributes, report generation attributes, etc. In particular examples, stimulus attributes include time span, channel, rating, media, type, etc. Stimulus attributes may also include positions of entities in various frames, components, events, object relationships, locations of objects and duration of display. Purpose attributes include aspiration and objects of the stimulus including excitement, memory retention, associations, etc. Presentation attributes include audio, video, imagery, and messages needed for enhancement or avoidance. Other attributes may or may not also be included in the stimulus attributes repository or some other repository.

The data cleanser device 121 and the stimulus attributes repository 131 pass data to the data analyzer 181. The data analyzer 181 uses a variety of mechanisms to analyze underlying data in the system to place stimulus. According to various examples, the data analyzer customizes and extracts the independent neurological and neuro-physiological parameters for each individual in each modality, and blends the estimates within a modality as well as across modalities to elicit an enhanced response to the presented stimulus material. In particular examples, the data analyzer 181 aggregates the response measures across subjects in a dataset.

According to various examples, neurological and neuro-physiological signatures are measured using time domain analyses and frequency domain analyses. Such analyses use parameters that are common across individuals as well as parameters that are unique to each individual. The analyses could also include statistical parameter extraction and fuzzy logic based attribute estimation from both the time and frequency components of the synthesized response.

In some examples, statistical parameters used in a blended effectiveness estimate include evaluations of skew, peaks, first and second moments, population distribution, as well as fuzzy estimates of attention, emotional engagement and memory retention responses.

According to various examples, the data analyzer 181 may include an intra-modality response synthesizer and a cross-modality response synthesizer. In particular examples, the intra-modality response synthesizer is configured to customize and extract the independent neurological and neurophysiological parameters for each individual in each modality and blend the estimates within a modality analytically to elicit an enhanced response to the presented stimuli. In particular embodiments, the intra-modality response synthesizer also aggregates data from different subjects in a dataset.

According to various examples, the cross-modality response synthesizer or fusion device blends different intra-modality responses, including raw signals and signals output. The combination of signals enhances the measures of effectiveness within a modality. The cross-modality response fusion device can also aggregate data from different subjects in a dataset.

According to various examples, the data analyzer 181 also includes a composite enhanced effectiveness estimator (CEEE) that combines the enhanced responses and estimates from each modality to provide a blended estimate of the effectiveness. In particular examples, blended estimates are provided for each exposure of a subject to stimulus materials. The blended estimates are evaluated over time to assess stimulus location characteristics. According to various examples, numerical values are assigned to each blended estimate. The numerical values may correspond to the intensity of neuro-response measurements, the significance of peaks, the change between peaks, etc. Higher numerical values may correspond to higher significance in neuro-response intensity. Lower numerical values may correspond to lower significance or even insignificant neuro-response activity. In other examples, multiple values are assigned to each blended estimate. In still other examples, blended estimates of neuro-response significance are graphically represented to show changes after repeated exposure.

According to various examples, the data analyzer 181 provides analyzed and enhanced response data to a data communication device 183. It should be noted that in particular instances, a data communication device 183 is not necessary. According to various examples, the data communication device 183 provides raw and/or analyzed data and insights. In particular examples, the data communication device 183 may include mechanisms for the compression and encryption of data for secure storage and communication.

According to various examples, the data communication device 183 transmits data using protocols such as the File Transfer Protocol (FTP), Hypertext Transfer Protocol (HTTP) along with a variety of conventional, bus, wired network, wireless network, satellite, and proprietary communication protocols. The data transmitted can include the data in its entirety, excerpts of data, converted data, and/or elicited response measures. According to various examples, the data communication device is a set top box, wireless device, computer system, etc. that transmits data obtained from a data collection device to a response integration system. In particular examples, the data communication device may transmit data even before data cleansing or data analysis. In other examples, the data communication device may transmit data after data cleansing and analysis.

In particular examples, the data communication device 183 sends data to a response integration system 185. According to various examples, the response integration system 185 assesses and extracts controlled and automatic attention characteristics. In particular examples, the response integration system 185 determines entity positions in various stimulus segments and matches position information with eye tracking paths while correlating saccades with neural assessments of attention, memory retention, and emotional engagement. In particular examples, the response integration system 185 also collects and integrates user behavioral and survey responses with the analyzed response data to more effectively select stimulus locations.

A variety of data can be stored for later analysis, management, manipulation, and retrieval. In particular examples, the repository could be used for tracking stimulus attributes and presentation attributes, audience responses and optionally could also be used to integrate audience measurement information.

As with a variety of the components in the system, the response integration system can be co-located with the rest of the system and the user, or could be implemented in a remote location. It could also be optionally separated into an assessment repository system that could be centralized or distributed at the provider or providers of the stimulus material. In other examples, the response integration system is housed at the facilities of a third party service provider accessible by stimulus material providers and/or users. A stimulus placement system 187 identifies temporal and spatial locations along with personalized material for introduction into the stimulus material. The personalized stimulus material introduced into a video game can be reintroduced to check the effectiveness of the placements.

FIG. 2 illustrates examples of data models that may be provided with a stimulus attributes repository. According to various examples, a stimulus attributes data model 201 includes a video game 203, rating 205, time span 207, audience 209, and demographic information 211. A stimulus purpose data model 213 may include intents 215 and objectives 217. According to various examples, stimulus attributes data model 201 also includes candidate location information 219 about various temporal, spatial, activity, and event components in an experience that may hold stimulus material. For example, a video game may show a blank wall included on some scenes that can be used to display an advertisement. The temporal and spatial characteristics of the blank wall may be provided in candidate location information 219.

According to various examples, another stimulus attributes data model 221 includes creation attributes 223, ownership attributes 225, broadcast attributes 227, and statistical, demographic and/or survey based identifiers 229 for automatically integrating the neuro-physiological and neuro-behavioral response with other attributes and meta-information associated with the stimulus.

FIG. 3 illustrates examples of data models that can be used for storage of information associated with selection of locations for the introduction of stimulus material. According to various examples, a dataset data model 301 includes an experiment name 303 and/or identifier, client attributes 305, a subject pool 307, logistics information 309 such as the location, date, and time of testing, and stimulus material 311 including stimulus material attributes.

In particular examples, a subject attribute data model 315 includes a subject name 317 and/or identifier, contact information 321, and demographic attributes 319 that may be useful for review of neurological and neuro-physiological data. Some examples of pertinent demographic attributes include marriage status, employment status, occupation, household income, household size and composition, ethnicity, geographic location, sex, race. Other fields that may be included in data model 315 include shopping preferences, entertainment preferences, and financial preferences. Shopping preferences include favorite stores, shopping frequency, categories shopped, favorite brands. Entertainment preferences include network/cable/satellite access capabilities, favorite shows, favorite genres, and favorite actors. Financial preferences include favorite insurance companies, preferred investment practices, banking preferences, and favorite online financial instruments. A variety of subject attributes may be included in a subject attributes data model 315 and data models may be preset or custom generated to suit particular purposes.

According to various examples, data models for neuro-feedback association 325 identify experimental protocols 327, modalities included 329 such as EEG, EOG, GSR, surveys conducted, and experiment design parameters 333 such as segments and segment attributes. Other fields may include experiment presentation scripts, segment length, segment details like stimulus material used, inter-subject variations, intra-subject variations, instructions, presentation order, survey questions used, etc. Other data models may include a data collection data model 337. According to various examples, the data collection data model 337 includes recording attributes 339 such as station and location identifiers, the data and time of recording, and operator details. In particular examples, equipment attributes 341 include an amplifier identifier and a sensor identifier.

Modalities recorded 343 may include modality specific attributes like EEG cap layout, active channels, sampling frequency, and filters used. EOG specific attributes include the number and type of sensors used, location of sensors applied, etc. Eye tracking specific attributes include the type of tracker used, data recording frequency, data being recorded, recording format, etc. According to various examples, data storage attributes 345 include file storage conventions (format, naming convention, dating convention), storage location, archival attributes, expiry attributes, etc.

A preset query data model 349 includes a query name 351 and/or identifier, an accessed data collection 353 such as data segments involved (models, databases/cubes, tables, etc.), access security attributes 355 included who has what type of access, and refresh attributes 357 such as the expiry of the query, refresh frequency, etc. Other fields such as push-pull preferences can also be included to identify an auto push reporting driver or a user driven report retrieval system.

FIG. 4 illustrates examples of queries that can be performed to obtain data associated with stimulus location selection and analysis of controlled and automatic attention. For example, users may query to determine what types of consumers respond most to a particular experience or component of an experience. According to various examples, queries are defined from general or customized scripting languages and constructs, visual mechanisms, a library of preset queries, diagnostic querying including drill-down diagnostics, and eliciting what if scenarios. According to various examples, subject attributes queries 415 may be configured to obtain data from a neuro-informatics repository using a location 417 or geographic information, session information 421 such as testing times and dates, and demographic attributes 419. Demographics attributes include household income, household size and status, education level, age of kids, etc.

Other queries may retrieve stimulus material based on shopping preferences of subject participants, countenance, physiological assessment, completion status. For example, a user may query for data associated with product categories, products shopped, shops frequented, subject eye correction status, color blindness, subject state, signal strength of measured responses, alpha frequency band ringers, muscle movement assessments, segments completed, etc. Experimental design based queries 425 may obtain data from a neuro-informatics repository based on experiment protocols 427, product category 429, surveys included 431, and stimulus provided 433. Other fields that may be used include the number of protocol repetitions used, combination of protocols used, and usage configuration of surveys.

Client and industry based queries may obtain data based on the types of industries included in testing, specific categories tested, client companies involved, and brands being tested. Response assessment based queries 437 may include attention scores 439, emotion scores, 441, retention scores 443, and effectiveness scores 445. Such queries may obtain materials that elicited particular scores.

Response measure profile based queries may use mean measure thresholds, variance measures, number of peaks detected, etc. Group response queries may include group statistics like mean, variance, kurtosis, p-value, etc., group size, and outlier assessment measures. Still other queries may involve testing attributes like test location, time period, test repetition count, test station, and test operator fields. A variety of types and combinations of types of queries can be used to efficiently extract data.

FIG. 5 illustrates examples of reports that can be generated. According to various examples, client assessment summary reports 501 include effectiveness measures 503, component assessment measures 505, and stimulus location effectiveness measures 507. Effectiveness assessment measures include composite assessment measure(s), industry/category/client specific placement (percentile, ranking, etc.), actionable grouping assessment such as removing material, modifying segments, or fine tuning specific elements, etc., and the evolution of the effectiveness profile over time. In particular examples, component assessment reports include component assessment measures like attention, emotional engagement scores, percentile placement, ranking, etc. Component profile measures include time based evolution of the component measures and profile statistical assessments. According to various examples, reports include the number of times material is assessed, attributes of the multiple presentations used, evolution of the response assessment measures over the multiple presentations, and usage recommendations.

According to various examples, client cumulative reports 511 include media grouped reporting 513 of all stimulus assessed, campaign grouped reporting 515 of stimulus assessed, and time/location grouped reporting 517 of stimulus assessed. According to various examples, industry cumulative and syndicated reports 521 include aggregate assessment responses measures 523, top performer lists 525, bottom performer lists 527, outliers 529, and trend reporting 531. In particular examples, tracking and reporting includes specific products, categories, companies, brands.

Figure 6:
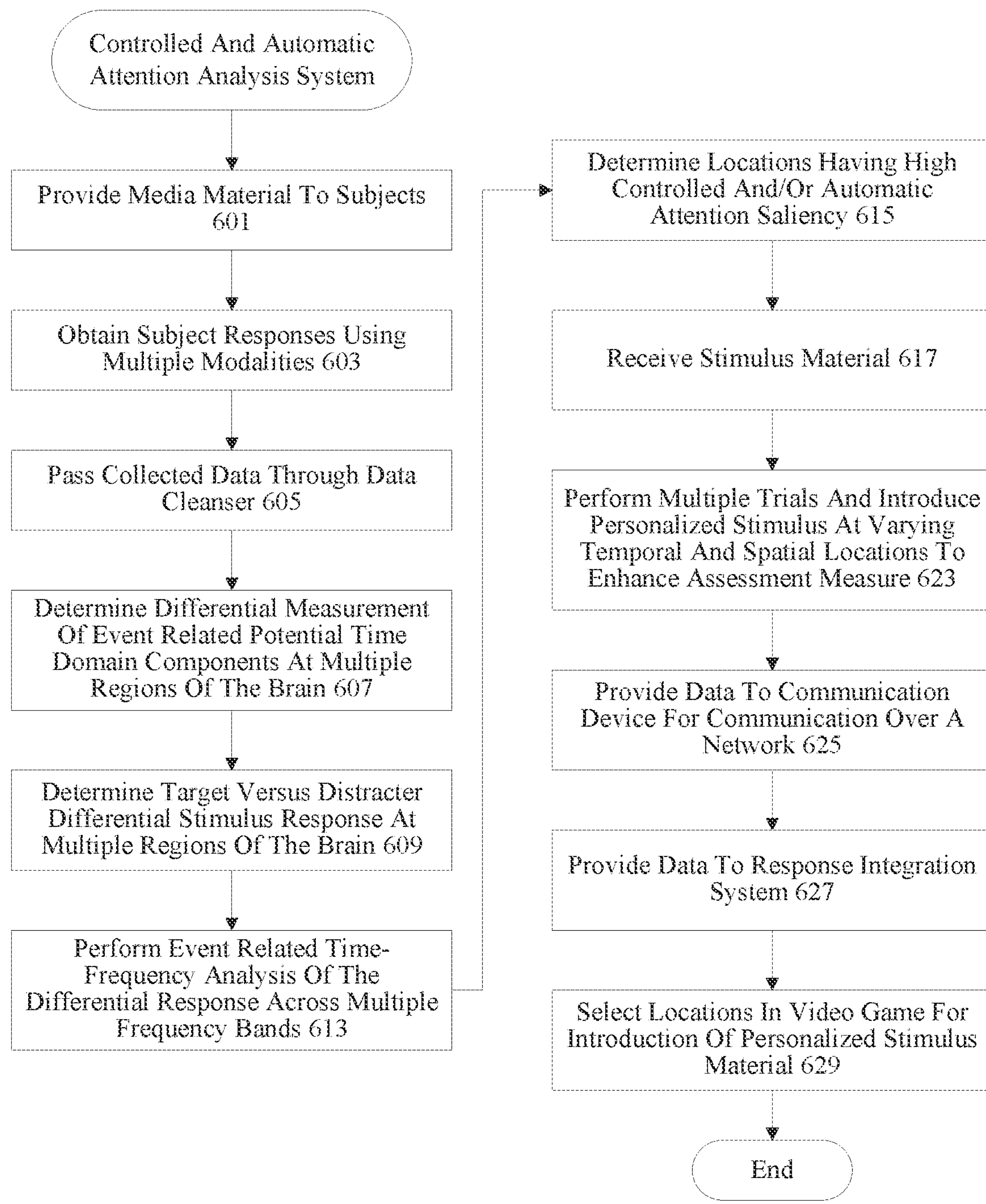
FIG. 6 illustrates one example of a technique for performing automatic and controlled attention location assessment.

FIG. 6 illustrates one example of stimulus location selection using analysis of controlled and automatic attention. At 601, stimulus material is provided to multiple subjects in multiple geographic markets. According to various examples, stimulus is a video game. At 603, subject responses are collected using a variety of modalities, such as EEG, ERP, EOG, GSR, etc. In some examples, verbal and written responses can also be collected and correlated with neurological and neurophysiological responses. In other examples, data is collected using a single modality. At 605, data is passed through a data cleanser to remove noise and artifacts that may make data more difficult to interpret. According to various examples, the data cleanser removes EEG electrical activity associated with blinking and other endogenous/exogenous artifacts.

According to various examples, data analysis is performed. Data analysis may include intra-modality response synthesis and cross-modality response synthesis to enhance effectiveness measures. It should be noted that in some particular instances, one type of synthesis may be performed without performing other types of synthesis. For example, cross-modality response synthesis may be performed with or without intra-modality synthesis.

A variety of mechanisms can be used to perform data analysis. In particular examples, a stimulus attributes repository is accessed to obtain attributes and characteristics of the stimulus materials, along with purposes, intents, objectives, etc. In particular examples, EEG response data is synthesized to provide an enhanced assessment of effectiveness. According to various examples, EEG measures electrical activity resulting from thousands of simultaneous neural processes associated with different portions of the brain. EEG data can be classified in various bands. According to various examples, brainwave frequencies include delta, theta, alpha, beta, and gamma frequency ranges. Delta waves are classified as those less than 4 Hz and are prominent during deep sleep. Theta waves have frequencies between 3.5 to 7.5 Hz and are associated with memories, attention, emotions, and sensations. Theta waves are typically prominent during states of internal focus.

Alpha frequencies reside between 7.5 and 13 Hz and typically peak around 10 Hz. Alpha waves are prominent during states of relaxation. Beta waves have a frequency range between 14 and 30 Hz. Beta waves are prominent during states of motor control, long range synchronization between brain areas, analytical problem solving, judgment, and decision making. Gamma waves occur between 30 and 60 Hz and are involved in binding of different populations of neurons together into a network for the purpose of carrying out a certain cognitive or motor function, as well as in attention and memory. Because the skull and dermal layers attenuate waves in this frequency range, brain waves above 75-80 Hz are difficult to detect and are often not used for stimuli response assessment.

However, the techniques and mechanisms of the present disclosure recognize that analyzing high gamma band (kappa-band: Above 60 Hz) measurements, in addition to theta, alpha, beta, and low gamma band measurements, enhances neurological attention, emotional engagement and retention component estimates. In particular examples, EEG measurements including difficult to detect high gamma or kappa band measurements are obtained, enhanced, and evaluated. Subject and task specific signature sub-bands in the theta, alpha, beta, gamma and kappa bands are identified to provide enhanced response estimates. According to various examples, high gamma waves (kappa-band) above 80 Hz (typically detectable with sub-cranial EEG and/or magnetoencephalograophy) can be used in inverse model-based enhancement of the frequency responses to the stimuli.

Various examples of the present disclosure recognize that particular sub-bands within each frequency range have particular prominence during certain activities. A subset of the frequencies in a particular band is referred to herein as a sub-band. For example, a sub-band may include the 40-45 Hz range within the gamma band. In particular examples, multiple sub-bands within the different bands are selected while remaining frequencies are band pass filtered. In particular examples, multiple sub-band responses may be enhanced, while the remaining frequency responses may be attenuated.

An information theory based band-weighting model is used for adaptive extraction of selective dataset specific, subject specific, task specific bands to enhance the effectiveness measure. Adaptive extraction may be performed using fuzzy scaling. Stimuli can be presented and enhanced measurements determined multiple times to determine the variation profiles across multiple presentations. Determining various profiles provides an enhanced assessment of the primary responses as well as the longevity (wear-out) of the marketing and entertainment stimuli. The synchronous response of multiple individuals to stimuli presented in concert is measured to determine an enhanced across subject synchrony measure of effectiveness. According to various examples, the synchronous response may be determined for multiple subjects residing in separate locations or for multiple subjects residing in the same location.

Although a variety of synthesis mechanisms are described, it should be recognized that any number of mechanisms can be applied—in sequence or in parallel with or without interaction between the mechanisms.

Although intra-modality synthesis mechanisms provide enhanced significance data, additional cross-modality synthesis mechanisms can also be applied. A variety of mechanisms such as EEG, Eye Tracking, GSR, EOG, and facial emotion encoding are connected to a cross-modality synthesis mechanism. Other mechanisms as well as variations and enhancements on existing mechanisms may also be included. According to various examples, data from a specific modality can be enhanced using data from one or more other modalities. In particular examples, EEG typically makes frequency measurements in different bands like alpha, beta and gamma to provide estimates of significance. However, the techniques of the present disclosure recognize that significance measures can be enhanced further using information from other modalities.

For example, facial emotion encoding measures can be used to enhance the valence of the EEG emotional engagement measure. EOG and eye tracking saccadic measures of object entities can be used to enhance the EEG estimates of significance including but not limited to attention, emotional engagement, and memory retention. According to various examples, a cross-modality synthesis mechanism performs time and phase shifting of data to allow data from different modalities to align. In some examples, it is recognized that an EEG response will often occur hundreds of milliseconds before a facial emotion measurement changes. Correlations can be drawn and time and phase shifts made on an individual as well as a group basis. In other examples, saccadic eye movements may be determined as occurring before and after particular EEG responses. According to various examples, time corrected GSR measures are used to scale and enhance the EEG estimates of significance including attention, emotional engagement and memory retention measures.

Evidence of the occurrence or non-occurrence of specific time domain difference event-related potential components (like the DERP) in specific regions correlates with subject responsiveness to specific stimulus. According to various examples, ERP measures are enhanced using EEG time-frequency measures (ERPSP) in response to the presentation of the marketing and entertainment stimuli. Specific portions are extracted and isolated to identify ERP, DERP and ERPSP analyses to perform. In particular examples, an EEG frequency estimation of attention, emotion and memory retention (ERPSP) is used as a co-factor in enhancing the ERP, DERP and time-domain response analysis.

EOG measures saccades to determine the presence of attention to specific objects of stimulus. Eye tracking measures the subject's gaze path, location and dwell on specific objects of stimulus. According to various examples, EOG and eye tracking is enhanced by measuring the presence of lambda waves (a neurophysiological index of saccade effectiveness) in the ongoing EEG in the occipital and extra striate regions, triggered by the slope of saccade-onset to estimate the significance of the EOG and eye tracking measures. In particular examples, specific EEG signatures of activity such as slow potential shifts and measures of coherence in time-frequency responses at the Frontal Eye Field (FEF) regions that preceded saccade-onset are measured to enhance the effectiveness of the saccadic activity data.

GSR typically measures the change in general arousal in response to stimulus presented. According to various examples, GSR is enhanced by correlating EEG/ERP responses and the GSR measurement to get an enhanced estimate of subject engagement. The GSR latency baselines are used in constructing a time-corrected GSR response to the stimulus. The time-corrected GSR response is co-factored with the EEG measures to enhance GSR significance measures.

According to various examples, facial emotion encoding uses templates generated by measuring facial muscle positions and movements of individuals expressing various emotions prior to the testing session. These individual specific facial emotion encoding templates are matched with the individual responses to identify subject emotional response. In particular examples, these facial emotion encoding measurements are enhanced by evaluating inter-hemispherical asymmetries in EEG responses in specific frequency bands and measuring frequency band interactions. The techniques of the present disclosure recognize that not only are particular frequency bands significant in EEG responses, but particular frequency bands used for communication between particular areas of the brain are significant. Consequently, these EEG responses enhance the EMG, graphic and video based facial emotion identification.

According to various examples, post-stimulus versus pre-stimulus differential measurements of ERP time domain components in multiple regions of the brain (DERP) are measured at 607. The differential measures give a mechanism for eliciting responses attributable to the stimulus. For example the messaging response attributable to an ad or the brand response attributable to multiple brands is determined using pre-experience and post-experience estimates At 609, target versus distracter stimulus differential responses are determined for different regions of the brain (DERP). At 613, event related time-frequency analysis of the differential response (DERPSPs) are used to assess the attention, emotion and memory retention measures across multiple frequency bands. According to various examples, the multiple frequency bands include theta, alpha, beta, gamma and high gamma or kappa.

At 615, locations having high controlled and/or automatic attention saliency are identified. According to various examples, candidate locations may include areas immediately following a sequence of salient controlled attention. Candidate locations may include locations where a user has high anticipation or is in a state of high awareness. Alternatively, locations where a user is sufficiently primed may be selected for particular messages and placements. In other examples, neuro-response lulls in source material are identified.

Locations having little change in relation to neighboring locations may also be selected. In still other examples, locations are manually selected. At 617, stimulus material is received. According to various examples, stimulus material may include presentations, messages, banners, videos, audio, etc. In particular examples, a controlled and automatic attention analysis system determines neurologically effective locations to place the message.

For example, the message may be placed where a user will be directing maximum attention. In one example, the message may be shown when a hero is about to enter a room for a final confrontation. At 623, multiple trials are performed with stimulus material introduced in different spatial and temporal locations to assess the impact of introduction at each of the different spatial and temporal locations.

For example, introduction of new products at location A on a billboard in a video game scene may lead to more significant neuro-response activity for the billboard in general. Introduction of an image onto a video stream may lead to greater emotional engagement and memory retention. In other examples, increased neuro-response activity for introduced material may detract from neuro-response activity for other portions of source material. For examples, a salient image on one part of a billboard may lead to reduced dwell times for other portions of a billboard. According to various examples, aggregated neuro-response measurements are identified to determine optimal locations for introduction of stimulus material.

At 625, processed data is provided to a data communication device for transmission over a network such as a wireless, wireline, satellite, or other type of communication network capable of transmitting data. Data is provided to response integration system at 627. According to various examples, the data communication device transmits data using protocols such as the File Transfer Protocol (FTP), Hypertext Transfer Protocol (HTTP) along with a variety of conventional, bus, wired network, wireless network, satellite, and proprietary communication protocols. The data transmitted can include the data in its entirety, excerpts of data, converted data, and/or elicited response measures. According to various examples, data is sent using a telecommunications, wireless, Internet, satellite, or any other communication mechanisms that is capable of conveying information from multiple subject locations for data integration and analysis. The mechanism may be integrated in a set top box, computer system, receiver, mobile device, etc.

In particular examples, the data communication device sends data to the response integration system 627. According to various examples, the response integration system 627 combines the analyzed responses to the experience/stimuli, with information on the available stimuli and its attributes. A variety of responses including user behavioral and survey responses are also collected an integrated. At 629, one or more locations in the video game are selected for the introduction of personalized stimulus material.

According to various examples, the response integration system combines analyzed and enhanced responses to the stimulus material while using information about stimulus material attributes such as the location, movement, acceleration, and spatial relationships of various entities and objects. In particular examples, the response integration system also collects and integrates user behavioral and survey responses with the analyzed and enhanced response data to more effectively assess stimulus location characteristics.

According to various examples, the stimulus location selection system provides data to a repository for the collection and storage of demographic, statistical and/or survey based responses to different entertainment, marketing, advertising and other audio/visual/tactile/olfactory material. If this information is stored externally, this system could include a mechanism for the push and/or pull integration of the data—including but not limited to querying, extracting, recording, modifying, and/or updating. This system integrates the requirements for the presented material, the assessed neuro-physiological and neuro-behavioral response measures, and the additional stimulus attributes such as demography/statistical/survey based responses into a synthesized measure for the selection of stimulus locations.

According to various examples, the repository stores information for temporal, spatial, activity, and event based components of stimulus material. For example, neuro-response data, statistical data, survey based response data, and demographic data may be aggregated and stored and associated with a particular component in a video stream.

Figure 7:
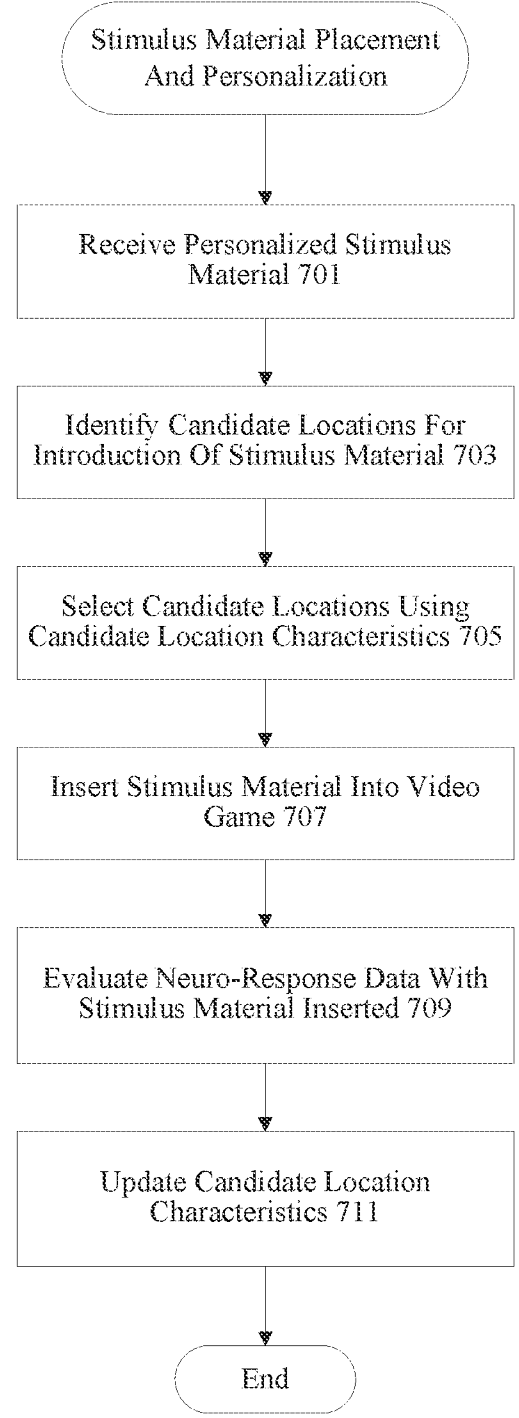
FIG. 7 illustrates one example of technique for introducing additional stimulus materials.

FIG. 7 illustrates an example of a technique for controlled and automatic attention analysis. According to various examples, additional stimulus material is received at 701. In particular examples, stimulus material may be video, audio, text, banners, messages, product offers, purchase offers, etc. At 703, candidate locations for introduction of stimulus material are identified. Candidate locations may be predetermined and provided with the media material such as the movie or video game itself. In particular examples, candidate locations are selected using neuro-response data to determine effective candidate locations for insertion of stimulus material. According to particular examples, candidate locations are locations having high controlled and/or automatic attention metrics. In other examples, candidate locations are neurologically salient locations for the introduction of advertisements, messages, purchase icons, media, offers, etc. In some examples, both personalized and non-personalized stimulus material may be inserted.

According to various examples, candidate locations are selected based on candidate location characteristics 705. For example, candidate location characteristics may indicate that some locations have particularly good memory and retention characteristics. In other examples, candidate location characteristics may indicate that a particular sport has good attention attributes. According to various examples, particular locations may indicate good priming for particular types of material, such as a category of ads or a type of message. According to various examples, particular events may also trigger stimulus material insertion. For example, if a player moves into first place into a racing game, a message or other stimulus material may be shown to the user. Stimulus material placement in video games may be spatial and temporal location driven or event driven. At 707, stimulus material is inserted into the video game. At 709, neuro-response data is evaluated with stimulus material inserted. In some examples, EEG data may be available. However, in other examples, little or no neuro-response data may be available. Only user activity or user facial expressions or user feedback may be available.

At 711, characteristics associated with candidate locations are updated based on user feedback. The location and placement assessment system can further include an adaptive learning component that refines profiles and tracks variations responses to particular stimuli or series of stimuli over time.

Figure 8:
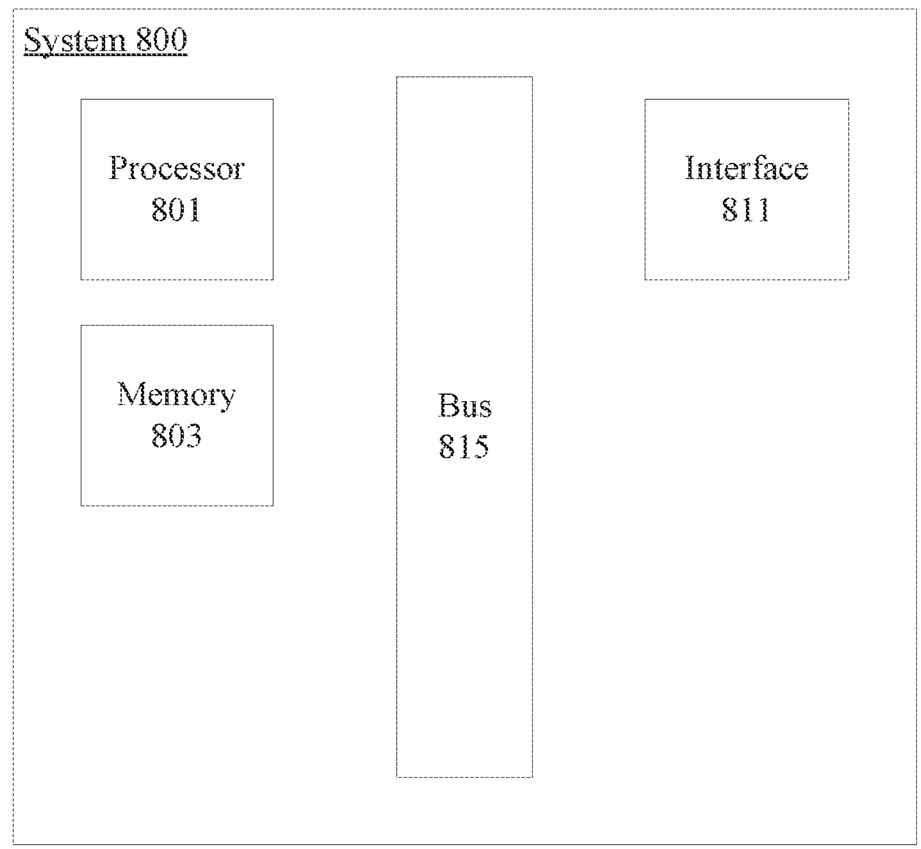
FIG. 8 provides one example of a system that can be used to implement one or more mechanisms.

According to various examples, various mechanisms such as the data collection mechanisms, the intra-modality synthesis mechanisms, cross-modality synthesis mechanisms, etc. are implemented on multiple devices. However, it is also possible that the various mechanisms be implemented in hardware, firmware, and/or software in a single system. FIG. 8 provides one example of a system that can be used to implement one or more mechanisms. For example, the system shown in FIG. 8 may be used to implement a stimulus location selection system.

According to particular examples, a system 800 suitable for implementing particular examples of the present disclosure includes a processor 801, a memory 803, an interface 811, and a bus 815 (e.g., a PCI bus). When acting under the control of appropriate software or firmware, the processor 801 is responsible for such tasks such as pattern generation. Various specially configured devices can also be used in place of a processor 801 or in addition to processor 801. The complete implementation can also be done in custom hardware. The interface 811 is typically configured to send and receive data packets or data segments over a network. Particular examples of interfaces the device supports include host bus adapter (HBA) interfaces, Ethernet interfaces, frame relay interfaces, cable interfaces, DSL interfaces, token ring interfaces, and the like.

In addition, various high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as data synthesis.

According to particular examples, the system 800 uses memory 803 to store data, algorithms and program instructions. The program instructions may control the operation of an operating system and/or one or more applications, for example. The memory or memories may also be configured to store received data and process received data.

Because such information and program instructions may be employed to implement the systems/methods described herein, the present disclosure relates to tangible, machine readable media that include program instructions, state information, etc. for performing various operations described herein. Examples of machine-readable media include, but are not limited to, magnetic media such as hard disks, floppy disks, and magnetic tape; optical media such as CD-ROM disks and DVDs; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Although the foregoing disclosure has been described in some detail for purposes of clarity of understanding, it will be apparent that certain changes and modifications may be practiced within the scope of the appended claims. Therefore, the present embodiments are to be considered as illustrative and not restrictive and the disclosure is not to be limited to the details given herein, but may be modified within the scope and equivalents of the appended claims.

What is claimed is:

1. An apparatus comprising:

memory;

instructions; and a processor to execute the instructions to:

determine a first attention level of a user exposed to source material based on first neuro-response data, the first neuro-response data gathered from the user while the user is exposed to the source material at a first time;

determine a second attention level of the user exposed to a first stimulus at a first location in the source material based on second neuro-response data, the second neuro-response data gathered from the user while the user is exposed to the first stimulus at the first location at a second time;

determine a third attention level of the user exposed to a second stimulus at a second location in the source material based on third neuro-response data, the third neuro-response data gathered from the user while the user is exposed to the second stimulus at the second location at a third time, the second location different from the first location;

determine a first change between the first attention level and the second attention level;

determine a second change between the first attention level and the third attention level; and select at least one of the first location or the second location as a candidate location for introduction of advertising material based on the first change and the second change, the processor to select the first location when the first change indicates increased attention to the first stimulus relative to the source material and the processor to select the second location when the second change indicates increased attention to the second stimulus relative to the source material.

2. The apparatus of claim 1, wherein the first attention level is a controlled attention level of the user for the source material at the first time and the second attention level is a controlled attention level of the user at the first location in the source material.

3. The apparatus of claim 1, wherein the third attention level is an automatic attention level of the user at the second location in the source material.

4. The apparatus of claim 1, wherein the processor is to determine the first change based on first event-related potential data in the first neuro-response data and second event-related potential data in the second neuro-response data.

5. The apparatus of claim 1, wherein the first location is a first spatial location in the source material and the second location is a second spatial location in the source material, the second spatial location proximate to the first spatial location.

6. The apparatus of claim 1, wherein the first location is a first temporal location in the source material and the second location is a second temporal location in the source material, the second temporal location proximate to the first temporal location in time.

7. The apparatus of claim 1, wherein the processor is to:

select the second location as the candidate location;

determine a fourth attention level of the user exposed to a third stimulus at a third location in the source material based on fourth neuro-response data, the fourth neuro-response data gathered from the user while the user is exposed to the third stimulus at the third location at a fourth time, the third location different from the first location;

determine a third change between the second attention level and the fourth attention level; and one of maintain or modify the selection of the second location as the candidate location based on the third change.

8. An apparatus comprising:

memory;

instructions; and a processor to execute the instructions to:

correlate a first location in media with first neuro-response data gathered from a user while the user is exposed to the media at a first time and a second location in the media with a second neuro-response data gathered from the user while the user is exposed to the media at a second time;

determine a first priming characteristic of the media at the first location based on the first neuro-response data;

determine a second priming characteristic of the media at the second location based on the second neuro-response data; and select a third location in the media after the first location or a fourth location in the media after the second location as a candidate location for introduction of advertising material based on the first priming characteristic and the second priming characteristic, the processor to select the third location when the first priming characteristic indicates increased receptivity to the advertising material at the first location relative to the second priming characteristic and select the fourth location when the second priming characteristic indicates increased receptivity to the advertising material at the second location relative to the first priming characteristic.

9. The apparatus of claim 8, wherein the processor is to determine the first priming characteristic based on one or more of a controlled attention level of the user at the first location, a memory retention level of the user at the first location, or a resonance level of the user at the first location.

10. The apparatus of claim 8, wherein the third location and the fourth location are one of a temporal location in the media or a spatial location in the media.

11. The apparatus of claim 8, wherein the processor is to identify one of a category or a content of the advertising material to be introduced based on the first priming characteristic or the second priming characteristic.

12. The apparatus of claim 8, wherein the processor is to:

analyze third neuro-response data gathered from the user while the user is exposed to the advertising material in the third location;

determine a third priming characteristic of the media at the third location based on the third neuro-response data; and perform a comparison of the second priming characteristic and the third priming characteristic, the processor to one of maintain the selection of the third location as the candidate location or modify the selection of the candidate location to the fourth location based on the comparison.

13. The apparatus of claim 8, wherein the processor is to correlate the first location in the media with the first neuro-response data based on a change in amplitude in the first neuro-response data.

14. The apparatus of claim 8, wherein the processor is to:

determine an automatic attention level of the user based on third neuro-response data gathered from the user while the user is exposed to the advertising material in the candidate location; and determine an effectiveness of the advertising material in the candidate location based on the automatic attention level.

15. An apparatus comprising:

memory;

instructions; and a processor to execute the instruction to:

identify a first event and a second event in first neuro-response data, the first neuro-response data gathered from a user while the user is exposed to media;

correlate a first location in the media with the first event and a second location in the media with the second event;

determine a first user resonance of the user at the first location based on the first event;

determine a second user resonance of the user at the second location based on the second event; and select a third location in the media after the first location or a fourth location in the media after the second location as a candidate location for introduction of advertising material based on the first user resonance and the second user resonance, the processor to select the candidate location by selecting the third location when the first user resonance is increased relative to the second user resonance or by selecting the fourth location when the second user resonance is increased relative to the first user resonance.

16. The apparatus of claim 15, wherein the third location and the fourth location are one of a temporal location in the media or a spatial location in the media.

17. The apparatus of claim 15, wherein the first event is a change in amplitude in the first neuro-response data.

18. The apparatus of claim 15, wherein the processor is to determine a first controlled attention level of the user at the first location based on the first neuro-response data and determine a second controlled attention level of the user at the second location based on the first neuro-response data, and wherein the processor is to select the third location or the fourth location as the candidate location based on the first controlled attention level and the second controlled attention level.

19. The apparatus of claim 15, wherein the processor is to:

determine a first controlled attention level of the user based on second neuro-response data gathered from the user while the user is exposed to the advertising material in the candidate location;

determine a second controlled attention level of the user based on third neuro-response data gathered from the user while the user is exposed to media at a fifth location in the media; and perform a comparison of the first controlled attention level and the second controlled attention level, the processor to one of maintain the selection of the candidate location or modify the selection of the candidate location based on the comparison.

20. The apparatus of claim 15, wherein the processor is to:

analyze second neuro-response data gathered from the user while the user is exposed to media in the third location and third neuro-response data gathered from the user while the user is exposed media in the fourth location; and perform a comparison of (1) the first neuro-response data and the second neuro-response data and (2) the first neuro-response data and the third neuro-response data, the processor to further select the one of the third location or the fourth location as the candidate location based on the comparison.

* * * * *